United States Patent
Leach et al.

(10) Patent No.: US 9,623,051 B2
(45) Date of Patent: Apr. 18, 2017

(54) DECELLULARIZED EXTRACELLULAR MATRIX

(75) Inventors: J. Kent Leach, Davis, CA (US);
Martin Decaris, Vacaville, CA (US);
Archana Bhat, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 534 days.

(21) Appl. No.: 14/111,383

(22) PCT Filed: Apr. 16, 2012

(86) PCT No.: PCT/US2012/033766
§ 371 (c)(1),
(2), (4) Date: Oct. 11, 2013

(87) PCT Pub. No.: WO2012/142569
PCT Pub. Date: Oct. 18, 2012

(65) Prior Publication Data
US 2014/0023723 A1  Jan. 23, 2014

Related U.S. Application Data

(60) Provisional application No. 61/475,942, filed on Apr. 15, 2011.

(51) Int. Cl.
| | |
|---|---|
| *C12N 5/00* | (2006.01) |
| *C12N 5/02* | (2006.01) |
| *A61K 35/26* | (2015.01) |
| *A61K 35/28* | (2015.01) |
| *C12P 1/00* | (2006.01) |
| *A61L 27/36* | (2006.01) |
| *A61L 27/38* | (2006.01) |
| *A61L 27/54* | (2006.01) |
| *C12N 5/0775* | (2010.01) |

(52) U.S. Cl.
CPC .......... *A61K 35/28* (2013.01); *A61L 27/3633* (2013.01); *A61L 27/3834* (2013.01); *A61L 27/3895* (2013.01); *A61L 27/54* (2013.01); *C12N 5/0068* (2013.01); *C12N 5/0662* (2013.01); *C12N 5/0663* (2013.01); *C12N 5/0664* (2013.01); *C12N 5/0665* (2013.01); *C12N 5/0666* (2013.01); *C12N 5/0667* (2013.01); *C12N 5/0668* (2013.01); *C12N 2531/00* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | |
|---|---|---|
| 5,969,052 A | 10/1999 | Mumick et al. |
| 6,277,768 B1 | 8/2001 | Mumick et al. |
| 6,410,155 B2 | 6/2002 | Mumick et al. |
| 6,410,644 B2 | 6/2002 | Mumick et al. |
| 6,451,429 B2 | 9/2002 | Mumick et al. |
| 7,326,571 B2 | 2/2008 | Freyman |
| 2001/0044654 A1* | 11/2001 | Chen .................. A61L 27/3625 623/1.41 |
| 2005/0013870 A1* | 1/2005 | Freyman ............. A61L 27/3633 424/520 |
| 2005/0260612 A1* | 11/2005 | Padmini ................... A61F 2/08 435/6.14 |
| 2008/0181935 A1* | 7/2008 | Bhatia .................... A61K 38/39 424/443 |

FOREIGN PATENT DOCUMENTS

WO   WO 97/18842 A1   5/1997

OTHER PUBLICATIONS

Allori, A.C. et al., "Biological Basis of Bone Formation, Remodeling, and Repair—Part II: Extracellular Matrix," Tissue Engineering Part B Rev, 2008, pp. 275-283, vol. 14, No. 3.
Alsberg, E. et al., "Cell-interactive Alginate Hydrogels for Bone Tissue Engineering," Journal of Dental Research, 2001, pp. 2025-2029, vol. 80.
Alsberg, E., et al., "Engineering Growing Tissues," PNAS, Sep. 17, 2002, pp. 12025-12030, vol. 99, No. 19.
Anitua, E. et al., "Autologous Platelets as a Source of Proteins for Healing and Tissue Regeneration," Thromb Haemostasis, 2004, pp. 4-15, vol. 91.
Aulin, C. et al., "Extracellular Matrix-polymer Hybrid Materials Produced in a Pulsed-Flow Bioreactor System," Journal of Tissue Engineering Regenerative Medicine, 2009, pp. 188-195, vol. 3.
Badylak, S. F. et al., "Extracellular Matrix as a Biological Scaffold Material: Structure and Function," Acta Biomaterialia, 2009, pp. 1-13, vol. 5.
Badylak, S. F. et al., "The Extracellular Matrix as a Scaffold for Tissue Reconstruction," Cell & Developmental Biology, 2002, pp. 377-383, vol. 13.
Badylak, S. F. et al., "Immune Response to Biologic Scaffold Materials," Seminars in Immunology, 2008, pp. 109-116, vol. 20.
Bancroft, G. N. et al., "Fluid Flow Increases Mineralized Matrix Deposition in 3D Perfusion Culture of Marrow Stromal Osteoblasts in a Dose-Dependent Manner," Proc Natl Acad Sci USA, Oct. 1, 2002, pp. 12600-12605, vol. 99.
Bennett, K. P. et al., "Proteomics Reveals Multiple Routes to the Osteogenic Phenotype in Mesenchymal Stem Cells," BMC Genomics, 2007, pp. 380-390, vol. 8.
Bhat, A. et al., "Differential Growth Factor Adsorption to Calvarial Osteoblast-Secreted Extracellular Matrices Instructs Osteoblastic Behavior," PLoS One, Oct. 2011, pp. 1-10, vol. 6, Issue 10.
Bhat, A. et al., "Evaluation of Cross-Linked Chitosan Microparticles for Bone Regeneration," Journal of Tissue Engineering and Regenerative Medicine, 2010, pp. 532-542, vol. 4.

(Continued)

*Primary Examiner* — Chris R Tate
*Assistant Examiner* — Douglas F White
(74) *Attorney, Agent, or Firm* — Fenwick & West LLP

(57) ABSTRACT

Methods for producing compositions of decellularized extracellular matrix (DM) tissue culture are described. The compositions can be used for coating supports such as tissue culture substrates, osteogenic gels, and medical devices.

16 Claims, 33 Drawing Sheets

(56) References Cited

OTHER PUBLICATIONS

Caplan, A. I. et al., "Mesenchymal Stem Cells as Trophic Mediators," Journal of Cellular Biochemistry, 2006, pp. 1076-1084, vol. 98.

Castano-Izquierdo, H. et al., "Pre-Culture Period of Mesenchymal Stem Cells in Osteogenic Media Influences Their In Vivo Bone Forming Potential," Journal of Biomedical Materials Research Part A, 2007, pp. 129-138, vol. 82.

Chang, S.C. et al., "Repair of Large Cranial Defects by hBMP-2 Expressing Bone Marrow Stromal Cells: Comparison Between Alginate and Collagen Type I Systems," Journal of Biomedical Mater Research, 2010, p. 433-441, vol. 94.

Chen, W. L. et al., "Integration of Statistical Modeling and High-Content Microscopy to Systematically Investigate Cell-substrate Interactions," Biomaterials, 2010, pp. 2489-2497, vol. 31.

Chen, X. D., "Extracellular Matrix Provides an Optimal Niche for the Maintenance and Propagation of Mesenchymal Stem Cells," Birth Defects Res C Embryo Today, 2010, pp. 45-54, vol. 90.

Chen, X. D. et al., "Extracellular Matrix Made by Bone Marrow Cells Facilitates Expansion of Marrow-Derived Mesenchymal Progenitor Cells and Prevents Their Differentiation into Osteoblasts," Journal of Bone and Mineral Research, 2007, pp. 1943-1956, vol. 22, No. 12.

Choi, K. M. et al., "Effect of Ascorbic Acid on Bone Marrow-Derived Mesenchymal Stem Cell Proliferation and Differentiation," Journal of Bioscience and Bioengineering, 2008, pp. 586-594, vol. 105.

Cool, S. M. et al., "Substrate Induction of Osteogenesis from Marrow-Derived Mesenchymal Precursors," Stem Cells and Development, 2005, pp. 632-642, vol. 14.

Dahl, S. L. et al., "Decellularized Native and Engineered Arterial Scaffolds for Transplantation," Cell Transplantation, 2003, pp. 659-666, vol. 12.

Datta, N. et al., "Effect of Bone Extracellular Matrix Synthesized in Vitro on the Osteoblastic Differentiation of Marrow Stromal Cells," Biomaterials, 2005, pp. 971-977, vol. 26.

Datta, N. et al., "In Vitro Generated Extracellular Matrix and Fluid Shear Stress Synergistically Enhance 3D Osteoblastic Differentiation," Proc Natl Acad Sci USA, Feb. 21, 2006, pp. 2488-2493, vol. 103, No. 8.

Davis, H.E. et al., Supplementation of Fibrin Gels with Sodium Chloride Enhances Physical Properties and Ensuing Osteogenic Response, Acta Biomaterialia, 2011, pp. 691-699, vol. 7.

Davis, H. E. et al., "Biomimetic Scaffolds Fabricated from Apatite-Coated Polymer Microspheres," Journal of Biomedical Materials Research, 2009, pp. 1021-1031, vol. 90.

Davis H.E. et al., "Designing Bioactive Delivery Systems for Tissue Regeneration," Annals of Biomedical Engineering, Jan. 2011, pp. 1-13, vol. 39, No. 1.

Davis, H.E. et al., "Osteogenic Response to BMP-2 of hMSCs Grown on Apatite-Coated Scaffolds," Biotechnology and Bioengineering, Nov. 2011, pp. 2727-2735, vol. 108, No. 11.

Decaris, M. L. et al., "Influence of the Oxygen Microenvironment on the Proangiogenic Potential of Human Endothelial Colony Forming Cells," Angiogenesis, 2009, pp. 303-311, vol. 12.

Decaris, M.L. et al., "Design of Experiments Approach to Engineer Cell-Secreted Matrices for Directing Osteogenic Differentiation," Annals of Biomedical Engineering, Apr. 2011, pp. 1174-1185, vol. 39, No. 4.

Decaris, M.L. et al., "Transferable Cell-Secreted Extracellular Matrices Enhance Osteogenic Differentiation," Acta Biomaterialia, 2012, pp. 744-752, vol. 8.

Dennis, J.E. et al., "Osteogenesis in Marrow-Derived Mesenchymal Cell Porous Ceramic Composites Transplanted Subcutaneously: Effect of Fibronectin and Laminin on Cell Retention and Rate of Osteogenic Expression," Cell Transplantation, 1992, pp. 23-32, vol. 1.

Diduch, D.R. et al., "Marrow Stromal Cells Embedded in Alginate for Repair of Osteochondral Defects," Arthroscopy, Sep. 2000, pp. 571-577, vol. 16, No. 6.

Even-Ram, S. et al., "Matrix Control of Stem Cell Fate," Cell, Aug. 25, 2006, pp. 645-647, vol. 126.

Frondoza, C. et al., "Human Chondrocytes Proliferate and Produce Matrix Components in Microcarrier Suspension Culture," Biomaterials, 1996, pp. 879-888, vol. 17.

Gentili, C. et al., "Cartilage and Bone Extracellular Matrix," Current Pharmaceutical Design, 2009, p. 1334, vol. 15.

Gilbert, T.W. et al., "Decellularization of Tissues and Organs," Biomaterials, 2006, pp. 3675-3683, vol. 27.

Gkioni, K. et al., "Mineralization of Hydrogels for Bone Regeneration," Tissue Engineering: Part B Rev, 2010, pp. 577-585, vol. 16, No. 6.

Gordon, J. A. et al., "Bone Sialoprotein Expression Enhances Osteoblast Differentiation and Matrix Mineralization In Vitro," Bone, 2007, pp. 462-473, vol. 41.

Grayson, W. L. et al., "Effects of Initial Seeding Density and Fluid Perfusion Rate on Formation of Tissue-Engineered Bone," Tissue Engineering, 2008, pp. 1809-1820, vol. 14, No. 11.

Grayson, W. L. et al., "Hypoxia Enhances Proliferation and Tissue Formation of Human Mesenchymal Stem Cells," Biochemical and Biophysical Research Communications, 2007, pp. 948-953, vol. 358.

Griffiths, L. G. et al., "Immunoproteomic Identification of Bovine Pericardium Xenoantigens," Biomaterials, 2008, pp. 3514-3520, vol. 29.

Grigoriou, V. et al., "Apoptosis and Survival of Osteoblast-Like Cells are Regulated by Surface Attachment," J Biol Chem, 2005, pp. 1733-1739, vol. 280.

Grunert, M. et al., "Isolation of a Native Osteoblast Matrix with a Specific Affinity for BMP2," J Mol Histol, 2007, pp. 393-404, vol. 38.

Guilak, F. et al., "Control of Stem Cell Fate by Physical Interactions with the Extracellular Matrix," Cell Stem Cell, Jul. 2, 2009, pp. 17-26, vol. 5.

He, J. et al., "Oxygen Tension Differentially Influences Osteogenic Differentiation of Human Adipose Stem Cells in 2D and 3D Cultures," Journal of Cellular Biochemistry, 2010, pp. 87-96, vol. 110.

He, J. et al., "Osteogenesis and Trophic Factor Secretion are Influenced by the Composition of Hydroxyapatite/ Poly(Lactide-Co-Glycolide) Composite Scaffolds," Tissue Engineering, 2010, p. 127-137, vol. 16, Part A.

Hern, D.L. et al., "Incorporation of Adhesion Peptides into Nonadhesive Hydrogels Useful for Tissue Resurfacing," J BioMed Mater Res, 1998, pp. 266-276, vol. 39.

Hidalgo-Bastida, L.A. et al., "Mesenchymal Stem Cells, Osteoblasts and Extracellular Matrix Proteins: Enhancing Cell Adhesion and Differentiation for Bone Tissue Engineering," Tissue Engineering: Part B Rev, 2010, pp. 405-412, vol. 16, No. 4.

Hoshiba, T. et al., "Development of Stepwise Osteogenesis-Mimicking Matrices for the Regulation of Mesenchymal Stem Cell Functions," The Journal of Biological Chemistry, 2009, pp. 31164-31173, vol. 284.

Hoshiba, T. et al., "Decellularized Matrices for Tissue Engineering," Expert Opinion on Biological Therapy, Dec. 2010, pp. 1717-1728, vol. 10, No. 12.

Hynes, R.O., "The Extracellular Matrix: Not Just Pretty Fibrils," Science, 2009 pp. 1216-1219, vol. 27, No. 326.

Im, D.D. et al., "Extracellular-Signal-Related Kinase 1/2 is Responsible for Inhibition of Osteogenesis in Three Dimensional Cultured MC3T3-E1 Cells," Tissue Engineering: Part A, 2010, pp. 3485-3494, vol. 16, No. 11.

Jaiswal, N. et al., "Osteogenic Differentiation of Purified, Culture-Expanded Human Mesenchymal Stem Cells in Vitro," Journal of Cellular Biochemistry, 1997, pp. 295-312, vol. 64.

Jaiswal, R.K. et al., "Adult Human Mesenchymal Stem Cell Differentiation to the Osteogenic or Adipogenic Lineage is Regulated by Mitogen-Activated Protein Kinase," J Biol Chem, 2000, pp. 9645-9652, vol. 275.

Jones, E. et al., "Mesenchymal Stem Cells and Bone Regeneration: Current Status," Injury, 2011, p. 562-568, vol. 42.

(56) References Cited

OTHER PUBLICATIONS

Kang, Y. et al., "Creation of Bony Microenvironment with CaP and Cell-Derived ECM to Enhance Human Bone-Marrow MSC Behavior and Delivery of BMP-2," Biomaterials, 2011, p. 6119-6130, vol. 32.
Kempen, D.H. et al., "Effect of Local Sequential VEGF and BMP-2 Delivery on Ectopic and Orthotopic Bone Regeneration," Biomaterials, 2009, pp. 2816-2825, vol. 30.
Kim, S. H. et al., "Development of Serum-Free Medium Supplemented with Hydrolysates for the Production of Therapeutic Antibodies in CHO Cell Cultures Using Design of Experiments," Applied Microbiology and Biotechnology, 2009, pp. 639-648, vol. 83.
Kozawa, O. et al., "Involvement of p70 S6 Kinase in Bone Morphogenetic Protein Signaling: Vascular Endothelial Growth Factor Synthesis by Bone Morphogenetic Protein-4 in Osteoblasts," Journal of Cellular Biochemistry, 2001, pp. 430-436, vol. 81.
Kundu, A. K. et al., "Vitronectin and Collagen I Differentially Regulate Osteogenesis in Mesenchymal Stem Cells," Biochemical and Biophysical Research Communications, 2006, pp. 347-357, vol. 347.
Kundu, A.K. et al., "Extracellular Matrix Remodeling, Integrin Expression, and Downstream Signaling Pathways Influence the Osteogenic Differentiation of Mesenchymal Stem Cells on Poly(Lactide-Co-Glycolide) Substrates," Tissue Engineering: Part A, 2009, pp. 273-283, vol. 15, No. 2.
Lao, L.H. et al., "Chitosan Modified Poly(L-lactide) Microspheres as Cell Microcarriers for Cartilage Tissue Engineering," Colloid Surface B, 2008, pp. 218-225, vol. 66.
Lebaron, R.G. et al., "Extracellular Matrix Cell Adhesion Peptides: Functional Applications in Orthopedic Materials," Tissue Engineering, 2000, pp. 85-103, vol. 6, No. 2.
Lecanda, F. et al., "Regulation of Bone Matrix Protein Expression and Induction of Differentiation of Human Osteoblasts and Human Bone Marrow Stromal Cells by Bone Morphogenetic Protein-2," Journal of Cellular Biochemistry, 1997, pp. 386-396, vol. 67.
Lee, K.Y. et al., "Hydrogels for Tissue Engineering," Chemical Reviews, Jul. 2001, pp. 1869-1879, vol. 101, No. 7.
Lian, J. B. et al., "Regulatory Controls for Osteoblast Growth and Differentiation: Role of Runx/Cbfa/ AML Factors," Critical Reviews in Eukaryotic Gene Expression, 2004, pp. 1-41, vol. 14, Issues 1&2.
Liao, J. et al., "Modulation of Osteogenic Properties of Biodegradable Polymer/Extracellular Matrix Scaffolds Generated with a Flow Perfusion Bioreactor," Acta Biomaterialia, 2010, pp. 2386-2393, vol. 6.
Liao, J. et al., "Bioactive Polymer/Extracellular Matrix Scaffolds Fabricated with a Flow Perfusion Bioreactor for Cartilage Tissue Engineering," Biomaterials, 2010, pp. 8911-8920, vol. 31.
Lund, A.W. et al., "Inhibition of ERK Promotes Collagen Gel Compaction and Fibrillogenesis to Amplify the Osteogenesis of Human Mesenchymal Stem Cells in Three-Dimensional Collagen I Culture," Stem Cells and Development, 2009, pp. 331-341, vol. 18, No. 2.
Lutolf, M.P. et al., Synthetic Biomaterials as Instructive Extracellular Microenvironments for Morphogenesis in Tissue Engineering. Nature Biotechnology, Jan. 2005, pp. 47-55, vol. 23, No. 1.
Malda, J. et al., "Microcarriers in the Engineering of Cartilage and Bone," Trends in Biotechnology, Jul. 2006, pp. 299-304, vol. 24, No. 7.
Manton, K.J. et al., "Disruption of Heparan and Chondroitin Sulfate Signaling Enhances Mesenchymal Stem Cell-Derived Osteogenic Differentiation Via Bone Morphogenetic Protein Signaling Pathways," Stem Cells, 2007, pp. 2845-2854, vol. 25.
Mauney, J. R. et al., "Matrix-Mediated Retention of Osteogenic Differentiation Potential by Human Adult Bone Marrow Stromal Cells During Ex Vivo Expansion," Biomaterials, 2004, pp. 3233-3243, vol. 25.
Mauney, J. R. et al., "Matrix-Mediated Retention of In Vitro Osteogenic Differentiation Potential and in Vivo Bone-Forming Capacity by Human Adult Bone Marrow-Derived Mesenchymal Stem Cells During Ex Vivo Expansion," Journal of Biomedical Materials Research, 2006, pp. 464-475, vol. 79.
McKay, W.F. et al., "A Comprehensive Clinical Review of Recombinant Human Bone Morphogenetic Protein-2 (Infuse Bone Graft)," International Orthopaedics, 2007, pp. 729-734, vol. 31.
Mi, Z. et al., "Osteopontin Promotes CCL5-Mesenchymal Stromal Cell-Mediated Breast Cancer Metastasis," Carcinogenesis, 2011, pp. 477-487, vol. 32, No. 4.
Mochida, Y. et al., Decorin Modulates Collagen Matrix Assembly and Mineralization, Matrix Biology, 2009, pp. 44-52, vol. 28.
Naito, H. et al., "The Effect of Mesenchymal Stem Cell Osteoblastic Differentiation on the Mechanical Properties of Engineered Bone-Like Tissue," Tissue Engineering: Part A, 2011, pp. 2321-2329, vol. 17.
Nakashima, K. et al., "The Novel Zinc Finger-Containing Transcription Factor Osterix is Required for Osteoblast Differentiation and Bone Formation," Cell, Jan. 11, 2002, pp. 17-29, vol. 108.
Nguyen, L.H. et al., "Unique Biomaterial Compositions Direct Bone Marrow Stem Cells into Specific Chondrocytic Phenotypes Corresponding to the Various Zones of Articular Cartilage," Biomaterials, 2011, pp. 1327-1338, vol. 32.
Nguyen, M.K. et al., "Injectable Biodegradable Hydrogels," Macromolecular Bioscience, 2010, pp. 563-579, vol. 10.
Ogura, N. et al., "Differentiation of the Human Mesenchymal Stem Cells Derived from Bone Marrow and Enhancement of Cell Attachment by Fibronectin," Journal of Oral Science, 2004, pp. 207-213, vol. 46, No. 4.
Ohgushi, H. et al., "Mesenchymal Stem Cells and Bioceramics: Strategies to Regenerate the Skeleton," Novartis Foundation Symposium, 2003, pp. 118-127, discussion 27-32, 70-4, 239-41, vol. 249.
Panetta, N.J. et al., Mesenchymal Cells for Skeletal Tissue Engineering. Panminerva Med, 2009, pp. 25-41, vol. 51.
Parisuthiman, D. et al., "Biglycan Modulates Osteoblast Differentiation and Matrix Mineralization," Journal of Bone and Mineral Research, 2005, pp. 1878-1886, vol. 20, No. 10.
Petrie, T. A. et al., "Multivalent Integrin-Specific Ligands Enhance Tissue Healing and Biomaterial Integration," Science Translational Medicine, 2010, pp. 1-6, vol. 2, Issue 45, 45ra60.
Pham, Q. P. et al., "The Influence of an In Vitro Generated Bone-Like Extracellular Matrix on Osteoblastic Gene Expression of Marrow Stromal Cells," Biomaterials, 2008, pp. 2729-2739, vol. 29.
Pierschbacher, M.D. et al., "Cell Attachment Activity of Fibronectin can be Duplicated by Small Synthetic Fragments of the Molecule," Nature, May 1984, pp. 30-33, vol. 309.
Pittenger, M.F. et al., "Multilineage Potential of Adult Human Mesenchymal Stem Cells," Science, 1999, pp. 143-147, vol. 284.
Porter, B. et al., "3-D Computational modeling of Media Flow Through Scaffolds in a Perfusion Bioreactor," Journal of Biomechanics, 2005, pp. 543-549, vol. 38.
Prockop, D.J. et al., "Evolving Paradigms for Repair of Tissues by Adult Stem/Progenitor Cells (MSCs)," J Cell Mol Med, 2010, pp. 2190-2199, vol. 14, No. 9.
Rahman, S. et al., Modulation of RGD Sequence Motifs Regulates Disintegrin Recognition of $\alpha_{IIb} \beta_3$ and $\alpha_5\beta_1$ Integrin Complexes. Replacement of Elegantin Alanine-50 with Proline, N-Terminal to the RGD Sequence, Diminishes Recognition of the $\alpha_5 \beta_1$ Complex with Restoration Induced by $Mn^{2+}$cation, Biochem J, 1998, pp. 247-257, vol. 335.
Rao, R.R. et al., "Biomineralized Composite Substrates Increase Gene Expression with Nonviral Delivery," Journal of Biomedical Materials Research, 2010, pp. 344-354, vol. 94.
Rezania, A. et al., "Biomimetic Peptide Surfaces That Regulate Adhesion, Spreading, Cytoskeletal Organization, and Mineralization of the Matrix Deposited by Osteoblast-Like Cells," Biotechnol Progr., 1999, pp. 19-32, vol. 15.
Rowlands, A.S. et al., "Directing Osteogenic and Myogenic Differentiation of MSCs: Interplay of Stiffness and Adhesive Ligand Presentation," Am J Physiol Cell Physiol, 2008, pp. C1037-C1044, vol. 295.
Rowley, J.A. et al., "Alginate Hydrogels as Synthetic Extracellular Matrix Materials," Biomaterials, 1999, pp. 45-53, vol. 20.

(56) References Cited

OTHER PUBLICATIONS

Ruoslahti, E. et al., "Anchorage Dependence, Integrins, and Apoptosis," Cell, May 20, 1994, pp. 477-478, vol. 77.

Ruoslahti, E. et al., "New Perspectives in Cell Adhesion: RGD and Integrins," Science, Oct. 23, 1987, pp. 491-497, vol. 238, No. 4826.

Schmittgen, T.D. et al., "Analyzing Real-Time PCR Data by the Comparative $C_T$ Method," Nature Protocols, 2008, pp. 1101-1108, vol. 3, No. 6.

Schultz, G.S. et al., "Interactions Between Extracellular Matrix and Growth Factors in Wound Healing," Wound Repair and Regeneration, 2009, pp. 153-162, vol. 17.

Shah, M. et al., "Development and Statistical Optimization of Solid Lipid Nanoparticles of Simvastatin by Using $2^3$ Full-Factorial Design," AAPS PharmSciTech, Jun. 2010, pp. 489-496, vol. 11, No. 2.

Sheffield J.B. et al., "A Solid-Phase Method for the Quantitation of Protein in the Presence of Sodium Dodecyl Sulfate and Other Interfering Substances," Analytical Biochemistry, 1987, pp. 49-54, vol. 166.

Shekaran, A. et al., "Extracellular Matrix-Mimetic Adhesive Biomaterials for Bone Repair," J Biomed Mater Res A, 2011, pp. 261-272, vol. 96.

Simmons, C.A. et al., "Dual Growth Factor Delivery and Controlled Scaffold Degradation Enhance In Vivo Bone Formation by Transplanted Bone Marrow Stromal Cell," Bone, 2004, pp. 562-569, vol. 35.

Singelyn, J.M. et al., "Naturally Derived Myocardial Matrix as an Injectable Scaffold for Cardiac Tissue Engineering," Biomaterials, 2009, pp. 5409-5416, vol. 30.

Sofia, S. et al., "Functionalized Silk-Based Biomaterials for Bone Formation," Journal of Biomedical Materials Research, 2001, pp. 139-148, vol. 54.

Sreejalekshmi, K.G. et al., "Biomimeticity in Tissue Engineering Scaffolds Through Synthetic Peptide Modifications—Altering Chemistry for Enhanced Biological Response," J Biomed Mater Res, 2011, pp. 477-491, vol. 96.

Sun, Y. et al., "Rescuing Replication and Osteogenesis of Aged Mesenchymal Stem Cells by Exposure to a Young Extracellular Matrix," FASEB Journal, 2011, pp. 1474-1485, vol. 25.

Thibault, R.A. et al., "Osteogenic Differentiation of Mesenchymal Stem Cells on Pregenerated Extracellular Matrix Scaffolds in the Absence of Osteogenic Cell Culture Supplements," Tissue Engineering: Part A, 2010, pp. 431-440, vol. 16, No. 2.

Weltermann, A. et al., "Large Amounts of Vascular Endothelial Growth Factor at the Site of Hemostatic Plug Formation In Vivo," Arteriosclerosis, Thrombosis, and Vascular Biology, 1999, pp. 1757-1760, vol. 19.

Wu, Y.N. et al., "Cartilaginous ECM Component-Modification of the Micro-Bead Culture System for Chondrogenic Differentiation of Mesenchymal Stem Cells," Biomaterials, 2007, pp. 4056-4067, vol. 28.

Yan, M.N. et al., "Reconstruction of Peri-Implant Bone Defects Using Impacted Bone Allograft and BMP-2 Gene-Modified Bone Marrow Stromal Cells," J Biomed Mater Res, 2010, pp. 304-313, vol. 93.

Zahed, M.A. et al., "Optimal Conditions for Bioremediation of Oily Seawater," Bioresource Technology, 2010, pp. 9455-9460, vol. 101.

Zambonin, G. et al., "Biomaterials in Orthopaedic Surgery: Effects of Different Hydroxyapatites and Demineralized Bone Matrix on Proliferation Rate and Bone Matrix Synthesis by Human Osteoblasts," Biomaterials, 1995, pp. 397-402, vol. 16.

Zhang, Y. et al., "Tissue-Specific Extracellular Matrix Coatings for the Promotion of Cell Proliferation and Maintenance of Cell Phenotype," Biomaterials, 2009, pp. 4021-4028, vol. 30.

\* cited by examiner

DECELLULARIZED EXTRACELLULAR MATRIX

CROSS REFERENCE TO RELATED APPLICATIONS

This application claims the benefit of U.S. Provisional Application No. 61/475,942, filed Apr. 15, 2011, the entire disclosure of which is hereby incorporated by reference in its entirety for all purposes.

BACKGROUND AND SUMMARY

Briefly, and as described in more detail below, described herein is a method of depositing a decellularized extracellular matrix, e.g., a mesenchymal stem cell-secreted extracellular matrix, on biomaterials, e.g., polymeric implants of any size and geometry. This matrix is produced by cells, for example, MSCs derived from any tissue compartment (e.g., bone marrow, adipose tissue, muscle, dental pulp, etc.) on, e.g., tissue culture plastic (TCP) under controlled conditions. The result is then decellularized and removed from the TCP, resulting in a composition of the cell-secreted components without the antigenic cellular structures or contaminating DNA. The application and implantation of this decellularized extracellular matrix to supports accelerates tissue formation in a natural manner and has the opportunity to make implantable materials more patient-friendly and enhance integration into the patient by presenting a cell-derived surface coating.

Several features of the current approach should be noted. Unlike the coating of implants with homogeneous proteins (e.g., collagen I, fibronectin, vitronectin) that have previously demonstrated increased bone formation, the deposition of the complex array of proteins and polysaccharides included in the endogeneous cell-secreted ECM provides cells with a natural substrate for interaction, thereby enhancing cellular adhesion, viability, survival, and tissue formation. Moreover, the matrix can be generated from patients or an unrelated donor without concerns of immunogenicity due to the nature of MSCs and DNase treatment of these matrices, thereby addressing the concerns of immune response for ~4% of the population with allergies to collagen.

Disclosed herein are methods for producing compositions of decellularized extracellular matrix via tissue culture and use of the compositions for coating biomaterials such as tissue culture substrates, osteogenic gels, and medical devices.

Disclosed herein is a method for producing a composition comprising a decellularized extracellular matrix (DM), comprising a) obtaining a population of cells grown on a tissue culture substrate under conditions sufficient to form an extracellular matrix (ECM); b) removing the cells from the tissue culture substrate to form a tissue culture substrate coated with DM; c) separating the DM from the tissue culture substrate into a solvent to form a solution comprising the DM; and d) dissociating the DM in the solution, thereby producing the composition comprising the DM.

In some aspects, step a) comprises growing a population of human mesenchymal stem cells (MSCs) derived from bone marrow on a tissue culture substrate comprising tissue culture plastic (TCP) by seeding MSCs at 50,000 cells/cm$^2$ and maintaining the MSCs in ambient oxygen at 21% $O_2$ in alpha modified Eagle's medium (MEM) supplemented with 50 µg/ml ascorbate-2-phosphate for 15 days to form an ECM; wherein step b) comprises removing the cells from the tissue culture substrate by treatment with 0.5% Triton X-100 in 20 mM ammonium hydroxide ($NH_4OH$) in phosphate buffered saline (PBS) for 5 minutes at 37 degrees C. to form a tissue culture substrate coated with DM; wherein step c) comprises separating the DM from the tissue culture substrate by treatment with 0.02 N acetic acid and scraping the DM from the tissue culture substrate into the 0.02 N acetic acid to form a solution comprising the DM; and wherein step d) comprises dissociating the DM in the solution by sonication, thereby producing the composition comprising the DM.

In some aspects, the methods further include transferring the dissociated DM to a gelatinous support. In some aspects, the methods further include treating the tissue culture substrate coated with DM with a nuclease. In some aspects, the methods further include treating the tissue culture substrate coated with DM with a DNase. In some aspects, the methods further include drying the tissue culture substrate coated with DM. In some aspects, the methods further include lyophilizing the composition comprising the DM. In some aspects, the methods further include transferring the dissociated DM to a solid support.

In some aspects, the ECM is osteogenic, chondrogenic, myogenic, adipogenic, keratinogenic, keratogenic, neurogenic, tenogenic, angiogenic, urotheliogenic, hepatogenic, or nephrogenic. In some aspects, the ECM is osteogenic. In some aspects, the DM is effective at maintaining stem and progenitor cells in an undifferentiated or minimally differentiated state for the purpose of expansion and cell study.

In some aspects, the cells are mesenchymal stem cells (MSCs). In some aspects, the MSC are derived from bone marrow, adipose tissue, muscle, periodontal tissue, or dental pulp. In some aspects, the MSC are human, mouse, rat, dog, cat, rabbit, horse, pig, or nonhuman primate. In some aspects, the cells are human MSC. In some aspects, the cells are human MSC derived from bone marrow. In some aspects, the cells are obtained in a culture medium. In some aspects, the cells are obtained in Dulbecco's Modified Eagle's Medium.

In some aspects, the tissue culture substrate is tissue culture plastic (TCP) or glass or a bioceramic or natural proteins and polymers such as collagen or fibrin or substrates derived from synthetic polymers such as polycaprolactone or poly(lactide-co-glycolide) and its homopolymers or thermoresponsive materials such as poly(N-isopropylacrylamide). In some aspects, the tissue culture substrate is TCP. In some aspects, the conditions sufficient to form an ECM comprise seeding human MSCs at high density greater than or equal to 50,000 cells/sq. cm and maintaining in ambient oxygen at 21% $O_2$ in alpha modified Eagle's medium supplemented with 50-100 µg/ml ascorbate-2-phosphate for 15 days.

In some aspects, removing the cells from the tissue culture substrate is performed by treatment with detergent or by freeze/thaw cycles. In some aspects, removing the cells from the tissue culture substrate is performed by treatment with 0.5% Triton X-100 in 20 mM $NH_4OH$ in phosphate buffered saline (PBS) for 5 minutes at 37 degrees C.

In some aspects, separating the DM from the tissue culture substrate comprises treatment with an acidic solvent and mechanical removal of the DM from the tissue culture substrate or scraping or lifting the DM from thermoresponsive polymers by reducing the temperature. In some aspects, separating the DM from the tissue culture substrate comprises treatment with an acidic solvent and scraping the DM from the tissue culture substrate. In some aspects, the solvent comprises 0.02 N acetic acid.

In some aspects, dissociating the DM comprises sonication or mechanical homogenization or enzyme treatment. In some aspects, dissociating the DM comprises sonication.

Also described herein is a method for producing a composition comprising a decellularized osteogenic extracellular matrix (oDM) produced in tissue culture, the method comprising a) growing a population of human MSC derived from bone marrow on a tissue culture substrate comprising TCP by seeding human MSCs at high density (greater than or equal to 50,000 cells/sq. cm) and maintaining in ambient oxygen (21% $O_2$) in alpha modified Eagle's medium supplemented with 50 µg/ml ascorbate-2-phosphate for 15 days to form an extracellular matrix (ECM); b) removing the cells from the tissue culture substrate by treatment with 0.5% Triton X-100 in 20 mM $NH_4OH$ in PBS for 5 minutes at 37 degrees C. to form tissue culture substrate coated with oDM; c) separating the oDM from the tissue culture substrate by treatment with 0.02 N acetic acid and scraping the oDM from the tissue culture substrate into the 0.02 N acetic acid to form a solution comprising the oDM; and d) dissociating the oDM in the solution by sonication, thereby producing the composition comprising the osteogenic decellularized ECM.

Also described herein is a method for producing a composition comprising a decellularized extracellular matrix (DM) adsorbed with a biologically active material (BAM), comprising a) obtaining a population of cells grown on a tissue culture substrate under conditions sufficient to form an extracellular matrix (ECM); b) removing the cells from the tissue culture substrate to form a tissue culture substrate coated with DM; c) contacting the DM with the BAM under conditions sufficient for adsorption of the BAM by the DM; d) separating the DM from the tissue culture substrate into a solvent to form a solution comprising the DM adsorbed with BAM; and d) dissociating the DM in the solution, thereby producing the composition comprising the DM adsorbed with BAM. In some aspects, the biologically active material is a therapeutic agent, a small molecule, a nucleic acid, or a protein molecule. In some aspects, the biologically active material is a protein molecule that is differentially expressed in diabetes patients. Also described herein is a support contacted with the BAM contacted DM produced by any of the methods described herein. In some aspects, the support is an alginate gel.

Also described herein is a method of producing a composition comprising a decellularized extracellular matrix (DM) produced in tissue culture, comprising a) obtaining a population of cells on a thermoresponsive polymer at 37° C. under conditions sufficient to form an extracellular matrix (ECM); b) removing the cells with a hypotonic solution to form the composition comprising the DM; and c) reducing the temperature from 37° C. to 20° C. In some aspects, the thermoresponsive polymer is Poly(N-isopropylacrylamide) (PIPAAm). In some aspects, the thermoresponsive polymer is described in U.S. Pat. Nos. 6,451,429; 6,410,644; 6,410,155; 6,277,768; and 5,969,052; each of which is herein incorporated by reference in its entirety for all purposes.

Also described herein is a method for producing a composition comprising a decellularized extracellular matrix (DM) produced in tissue culture, comprising a) obtaining a population of human MSCs on a tissue culture substrate under conditions sufficient to form an extracellular matrix (ECM); and b) removing the cells from the tissue culture substrate with a hypotonic solution to form the composition comprising the DM. In some aspects, step a) comprises growing a population of human MSC derived from bone marrow on a tissue culture substrate comprising tissue culture plastic (TCP) by seeding human MSCs at 50,000 cells/cm² and maintaining the MSCs in ambient oxygen at 21% $O_2$ in alpha modified Eagle's medium (MEM) supplemented with 50 µg/ml ascorbate-2-phosphate for 15 days to form an extracellular matrix (ECM); and wherein step b) comprises removing the cells from the tissue culture substrate by treatment with 0.5% Triton X-100 in 20 mM $NH_4OH$ in PBS for 5 minutes at 37 degrees C. to form the composition comprising the DM.

Also described herein is a method for producing an osteogenic extracellular matrix comprising obtaining a population of human MSC seeded on a tissue culture substrate and maintaining the MSCs in ambient oxygen in a medium supplemented with ascorbate-2-phosphate under conditions sufficient to produce the osteogenic extracellular matrix.

Also described herein is a method for producing a support coated with a DM comprising contacting a support with a composition comprising a decellularized ECM produced by a method described herein.

In some aspects, the support is a second tissue culture substrate comprising TCP. In some aspects, the support comprises a microsphere. In some aspects, the support is a three dimensional polymeric biomaterial. In some aspects, the support is an alginate hydrogel. In some aspects, the support is a medical device. In some aspects, the support comprises metal.

Also described herein is a DM coated support produced by a method described herein.

Also described herein is a method for producing a support coated with a DM comprising contacting a support with a solution comprising a decellularized ECM (DM) derived from human MSCs. In some aspects, the DM is solubilized and homogenous in the solution.

Also described herein is a composition comprising a decellularized ECM produced by a method described herein. In some aspects, the composition further comprises a support, wherein the support is a bioceramic.

Also described herein is a solution comprising a solubilized and homogenously distributed decellularized ECM (DM) derived from human MSCs.

Also described herein is a composition comprising a decellularized ECM (DM) derived from human MSCs, wherein the DM has a protein content of about 10-20 µg/cm², wherein the DM has 99% less DNA as compared to a non-decellularized ECM control sample, and wherein the DM expresses type 1 collagen, fibronectin, biglycan, and, decorin. In some aspects, the composition further comprises a solid or gelatinous support.

Also described herein is a composition comprising human MSCs contacted with a decellularized ECM (DM) derived from human MSCs. In some aspects, the composition further comprises a solid or gelatinous support.

Also described herein is a composition comprising a solubilized, decellularized ECM, wherein the ECM is produced by tissue culture cells. In some aspects, the tissue culture cells are human cells. In some aspects, the composition further comprises a support, wherein the support is a bioceramic.

Also described herein is a support coated with a composition described herein.

Also described herein is a composition comprising a decellularized ECM produced by a method described herein and a crosslinking agent. In some aspects, the crosslinking agent is 1-Ethyl-3-[3-dimethylaminopropyl]carbodiimide hydrochloride (EDC).

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Figure 1:
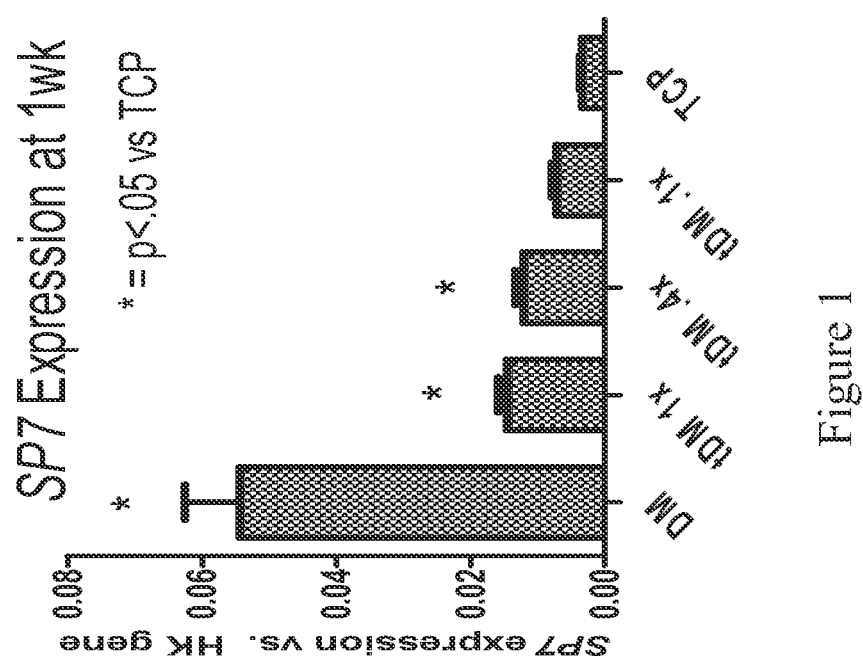
FIG. 1 shows qPCR results for osterix (SP7) expression from hMSCs cultured on tDMs.

As used herein, the terms "extracellular matrix" and "ECM" refer to a natural or artificial scaffolding for cell growth. Natural ECMs (ECMs found in multicellular organisms, such as mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestine submucosa (SIS), urinary bladder matrix (UBM) and liver stroma ECM each differ in their overall structure and composition due to the unique cellular niche needed for each tissue.

As used herein the term "decellularized" refers to the removal of cells and their related debris, for example, from the ECM. Removal of cells and their related debris from ECM produces a decellularized ECM (DM).

As used herein the term "support" refers to a substrate that can be contacted with DM. In some instances DM is introduced into a support. In some instances DM is coated onto a support. In some instances a support is solid and has a surface. In some instances a support is gelatinous. Examples of supports included biomaterials, biocompatible materials, scaffolds, microbeads, gels, pharmaceutical compositions, medical devices, and implants. Another example of a support is a crosslinking agent such as, e.g., 1-Ethyl-3-[3-dimethylaminopropyl]carbodiimide hydrochloride (EDC).

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

As used herein the term "biologically active material' refers to therapeutic agents, such as drugs, and also genetic materials and biological materials. Genetic materials include DNA or RNA, including, without limitation, DNA/RNA encoding a useful protein described below, intended to be inserted into a human body and, e.g., including viral vectors and non-viral vectors. Biological materials include cells, yeasts, bacteria, proteins, peptides, cytokines and hormones. Examples of peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin.

Cell Types, Mesenchymal Stem Cells (MSCs), and Culture Conditions.

Mesenchymal stem cells (MSCs; also known as mesenchymal progenitor cells) are cells capable of expanding in culture and differentiating into mesenchymal tissue cells, including bone, cartilage, tendon, ligament, muscle, adipose, and marrow stroma. MSCs synthesize, secrete, and/or organize extracellular matrix components (ECM; i.e., endogenous extracellular matrix production) under normal culture conditions.

MSCs can be obtained from a number of sources including, but not limited to, bone marrow, umbilical cord, placenta, amnion and other connective tissues (e.g. muscle, adipose, bone, tendon and cartilage). For example, umbilical cord MSC's can be isolated from umbilical cord blood, umbilical vein subendothelium, and the Wharton's Jelly. MCSs can further be isolated from three regions: the perivascular zone (umbilical cord perivascular cells or UCPVCs), the intervascular zone, placenta, amnion, and the subamnion (Troyer and Weiss, 2007). Alternatively, bone marrow-derived MSC's can be harvested from bone marrow and comprise non-hematopoietic, multipotential cells, support hematopoietic stem cell expansion, and can differentiate into various connective tissues.

Any number of different cell types can be used in the methods described herein, and selection depends on the purpose of the DM. Generally the cells chosen will be cells that secrete ECM, e.g., ECM-expressing cells. For example, the method can use mesenchymal stem cells (MSCs). The MSCs can be derived from, e.g., bone marrow, adipose tissue, muscle, periodontal tissue, or dental pulp. In addition, MSCs can be derived from, e.g., from various tissue compartments, osteoblasts, epithelial cells, endothelial cells, and fibroblasts from skin, dental pulp, and other compartments. Any number of mammals can be the source of cells, including but not limited to human, mouse, rat, dog, cat, rabbit, horse, pig, or nonhuman primate. In some embodiments, the cells are human MSCs, e.g., human MSCs derived from bone marrow. Human cells, as well as those from other mammalian species including, but not limited to, equine, canine, porcine, bovine, ovine, or rodent (e.g., mouse or rat) can be used. The cells can be derived as primary cells from relevant tissues or from serially passaged or subcultured from established cell stocks or banks that have been screened against viral and bacterial contamination and tested for purity. In addition, cells that are spontaneously, chemically or virally transfected or recombinant cells or genetically engineered cells can also be used in this invention. Also, the cells can be recombinant or genetically-engineered. The method described herein can be used with human cells and is not limited to non-human cells.

In order to efficiently secrete extracellular matrix, cells synthesizing ECM, e.g., MSCs, can be cultured for a number of days or weeks (e.g., less than 1, 1, 2, 3, 4, 5, 6, 7, 8, 9, 10, 11, 12, 13, 14, 15, 16, 17, 18, 19, 20, 21, 22, 23, 24, 25 or longer days) in an undefined medium or a chemically-defined medium. In a chemically-defined system comprising human-derived cells but no chemically undefined or non-human biological components or cells can be used. The cultures can be maintained in an incubator to ensure sufficient environmental conditions of controlled temperature, oxygen, humidity, and gas mixture for the culture of cells according to well known environmental variables. For example, the incubator can be between about 34 degrees C. to about 38 degrees C. (e.g., 37+/−1 degrees C.) with an atmosphere between about 5-10+/−1% CO2 and a relative humidity (Rh) between about 80-90%. Alternatively, cells can be cultured under hypoxic conditions. The cells can be temporarily exposed to ambient room temperature, air, and humidity during feeding, seeding, or other cell manipulations.

The method includes growing cells under conditions sufficient to form an ECM. One of skill will appreciate the conditions vary depending on the cell type and the intent of use of the ECM. One example of conditions includes seeding human MSCs derived from bone marrow at high density (greater than or equal to 50,000 cells/sq. cm) and maintaining in ambient oxygen (21% $O_2$) in alpha modified Eagle's medium supplemented with 50 µg/ml ascorbate-2-phosphate for 15 days. In some aspects, oxygen levels are ambient oxygen levels. In some aspects, oxygen levels can be less than 10, 10, 11, 12, 13, 14, 15, 16, 17, 18, 19, 20, 21, 22, 23, 24, 25, 26, 27, 28, 29, 30, or greater than 30% $O_2$. In some aspects, the amount of ascorbate-2-phosphate can be less than 10, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100, or greater than 100 µg/ml. In some aspects, cells can be cultured for a number of days or weeks (e.g., 2, 3, 4, 5, 6, 7, 8, 9, 10, 11, 12, 13, 14, 15, 16, 17, 18, 19, 20, 21, 22, 23, 24, 25 or longer days).

Regardless of cell type, culture media can be comprised of a nutrient base usually further supplemented with other components. Nutrient bases, which generally supply such nutrients as glucose, inorganic salts, an energy source, amino acids, and vitamins, are well known in the art of animal cell culture. Examples include, but are not limited to, Dulbecco's Modified Eagle's Medium (DMEM); Minimal Essential Medium (MEM); M199; RPMI 1640; Iscove's Modified Dulbecco's Medium (EDMEM). Minimal Essential Medium (MEM) and M199 require additional supplementation with phospholipid precursors and non-essential amino acids. Commercially available vitamin-rich mixtures that supply additional amino acids, nucleic acids, enzyme cofactors, phospholipid precursors, and inorganic salts include Ham's F-12, Ham's F-10, NCTC 109, and NCTC 135. Mixtures of such media can also be used, such as DMEM and Ham's F-12 between a 3-to-1 ratio to a 1-to-3 ratio, respectively.

Culture media formulations and additional dosing with media supplements for MSCs and additional cell types, such as fibroblasts or epithelial cells, can be selected according to well known cell culture methods in the art (see, for example, U.S. Pat. No. 5,712,163 to Parenteau, PCT Publication No. WO 95/31473, PCT Publication No. WO 00/29553, PCT Publication No. WO 2009/070720, Ham and McKeehan, Methods in Enzymology, 58:44-93 (1979), Bottenstein et al., Meth. Enzym., 58:94-109 (1979); each of which is incorporated herein in its entirety by this reference). For example, MSCs can be cultured in media supplemented with agents that promote matrix synthesis and deposition by the cells. Chemically defined culture media can be used that is free of undefined animal organ or tissue extracts such as serum, pituitary extract, hypothalamic extract, placental extract, or embryonic extract or proteins and factors secreted by feeder cells. Such media can be free of undefined components and biological components derived from non-human animal sources to diminish the risk of adventitious animal or cross-species virus contamination and infection. Synthetic or recombinant functional equivalents can replace the use of such animal organ or tissue extracts.

The methods described herein include growing cells on a tissue culture substrate. In some embodiments, the tissue culture substrate is tissue culture plastic (TCP). In other embodiments, the tissue culture substrate is glass or bioceramics or natural proteins and polymers such as collagen or fibrin or substrates derived from synthetic polymers such as poly(lactide-co-glycolide) and its homopolymers or thermo-responsive materials such as poly(N-isopropylacrylamide). Suitable substrates on which the cells can be grown can be any biologically compatible material, e.g., a tissue culture substrate. Materials such as glass; stainless steel; polymers, including polycarbonate, poly(ether sulfones) (PES), polystyrene, polyvinyl chloride, polyvinylidene, polydimethylsiloxane, fluoropolymers, and fluorinated ethylene propylene; and silicon substrates, including fused silica, polysilicon, or silicon crystals can be used. The material can be chemically treated or modified, electrostatically charged, or coated with biologicals such as poly-1-lysine or peptides. In one aspect, the substrate is a tissue culture plate.

Cells (e.g., MSCs) can be seeded at various levels of confluence. Seeding at superconfluency (i.e., greater than 100% confluency) can increase the rate of extracellular matrix formation by bypassing the cellular growth phase. Thus, cells can be directly seeded at superconfluence from 100% confluence up to about 900% confluence, including in the range of about 300% to about 600% confluence to immediately produce an extracellular matrix.

Alternatively, cells can be seeded at sub-confluence to proliferate prior to stimulating them to produce and organize an extracellular matrix.

Thus, in some aspects, cells can be seeded according to cell seeding densities per culture surface area and can be, for example, less than 10,000, 10,000, 20,000, 30,000, 40,000, 50,000, 60,000, 70,000, 80,000, 90,000, 100,000, or more cells per cm$^2$. Included in the foregoing sentence are any integers that fall between the stated numbers of cells per cm$^2$; thus, e.g., 45,000, 45,001, 45,002, 46,000, 47,000, 48,000, 49,000, 51,000, 52,000, 53,000, 54,000, and 55,000 cells per cm$^2$ are included.

In some aspects, methods described herein are used to produce DM for later coating of supports such as biomaterials for inducing growth of cells. The resulting DM can be osteogenic, chondrogenic, myogenic, adipogenic, keratinogenic, keratogenic, neurogenic, tenogenic, angiogenic, urotheliogenic, hepatogenic, or nephrogenic, depending on the source of cells growth conditions. In some embodiments, the DM is effective at maintaining stem and progenitor cells in an undifferentiated or minimally differentiated state for the purpose of expansion and cell study. In one embodiment, wherein the DM is osteogenic.

Decellularized Extracellular Matrix (DM) and Methods of Preparation.

In some aspects, the cells are removed from ECM. Decellularization is one way to remove cells and generally refers to the removal of all cells, cellular components, and other non-extracellular matrix components (e.g., serum, fat) while leaving intact an extracellular matrix (ECM) component. In some circumstances the process of decellularization can reduce or eliminate immune responses associated with the cells as well as the cellular components. (Schmidt and Baier, 2000, Biomaterials 21:2215-31).

Removal of cells can be by any method useful for decellularization while retaining the ECM. Removal methods include, e.g., treatment with detergent or by freeze/thaw cycles. In some embodiments, removing the cells from the tissue culture substrate can be performed by treatment with a detergent. In other embodiments, removing the cells from the tissue culture substrate can be performed by treatment with a detergent in combination with a buffer. In some embodiments, removing the cells from the tissue culture substrate can be performed by treatment with a hypotonic solution.

In some embodiments, removing the cells from the tissue culture substrate can be performed by treatment with Triton X-100 in NH$_4$OH in PBS. In some aspects, removing the cells from the tissue culture substrate can be performed by treatment with 0.5% Triton X-100 in 20 mM NH$_4$OH in PBS for 5 minutes at 37° C. In some aspects, removing the cells from the tissue culture substrate can be performed by treatment with less than 0.1, 0.1, 0.2, 0.3, 0.4, 0.5, 0.6, 0.7, 0.8, 0.9, 1.0% or greater of Triton X-100. In some aspects, removing the cells from the tissue culture substrate can be performed by treatment with Triton X-100 in less than 10, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100, or greater than 100 mM NH$_4$OH. In some aspects, removing the cells from the tissue culture substrate can be performed by treatment with Triton X-100 in less than 10, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, 100, or greater than 100 mM NH$_4$OH in PBS. In some aspects, removing the cells from the tissue culture substrate can be performed for less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more minutes. In some aspects, removing the cells from the tissue culture substrate can be performed at less than 20, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater ° C.

Several means of reducing the viability of native cells in tissues and organs are known, including physical, chemical, and biological methods (see, e.g. Kaushal et al., 2001, Nature Medicine 7(9):1035; Schmidt et al., supra; and U.S. Pat. No. 5,192,312, which are incorporated herein by reference). Such methods can be employed in accordance with the processes described herein. Decellularization by physical, chemical, and/or biological treatments can be optimized to preserve as much as possible the biological material of interest and the microstructure of the extracellular matrix.

In one embodiment, the formation of intracellular ice is used to decellularize the cells. For example, vapor phase freezing (slow rate of temperature decline) of the body tissue reduces the cellularity of the body tissue as compared to liquid phase freezing (rapid). However, slow freezing processes, in the absence of cryoprotectant, can result in tissue disruption such as cracking Colloid-forming materials can be added during freeze-thaw cycles to alter ice formation patterns in the body tissue. Polyvinylpyrrolidone (10% w/v) and dialyzed hydroxyethyl starch (10% w/v) can be added to standard cryopreservation solutions (DMEM, 10% DMSO, 10% fetal bovine serum) to reduce extracellular ice formation while permitting formation of intracellular ice. This allows a measure of decellularization while affording the collagenase tissue matrix some protection from ice damage.

Alternatively, the cells can be decellularized using a chemical technique. In one embodiment, the cells are treated with a solution effective to lyse native cells. In some aspects, the solution can be an aqueous hypotonic or low ionic strength solution formulated to effectively lyse the native tissue cells. Such an aqueous hypotonic solution can be de-ionized water or an aqueous hypotonic buffer. In some aspects, the aqueous hypotonic buffer can contain additives that provide suboptimal conditions for the activity of selected proteases, e.g., collagenase, which can be released as a result of cellular lysis.

In another embodiment, the cells are treated with a hypotonic lysis solution with or without protease inhibitors. General inhibitor solutions manufactured by Sigma and Genotech can be used. Specifically, 4-(2-aminoethyl)-benzene-sulfonyl fluoride, E-64, bestatin, leopeptin, aprotin, PMSF, Na EDTA, TIMPs, pepstatin A, phosphoramidon, and 1,10-phenanthroline are non-limiting examples of protease inhibitors. The hypotonic lysis solution can include a buffered solution of water, pH 5.5 to 8, preferably pH 7 to 8. In some embodiments, the hypotonic lysis solution is free from calcium and zinc ions. Additionally, control of the temperature and time parameters during the treatment of the body tissue with the hypotonic lysis solution, can also be employed to limit the activity of proteases.

In certain embodiments, the cells are treated with a detergent. In one embodiment, the cells are treated with an anionic detergent, e.g., sodium dodecyl sulfate in buffer. In another embodiment, the cells are treated with a non-ionic detergent, such as Triton X-100 or 1% octyl phenoxyl polyethoxyethanol, to solubilize cell membranes and fat. In one embodiment, the cells are treated with a combination of different classes of detergents, for example, a nonionic detergent, Triton X-100, and an anionic detergent, sodium dodecyl sulfate, to disrupt cell membranes and aid in the removal of cellular debris from tissue.

Steps can be taken to eliminate any residual detergent levels in the extracellular matrix, so as to avoid interference with the latter's ability to repair, regenerate, or strengthen defective, diseased, damaged or ischemic tissues or organs. Selection of detergent type and concentration can be based partly on its preservation of the structure, composition, and biological activity of the extracellular matrix.

In other embodiments, extracellular matrix can be isolated from the cells using a biological technique. Various enzymes can be used to eliminate viable native cells from the body tissue. In some aspects, the enzyme treatment limits the generation of new immunological sites. For instance, extended exposure of the body tissue to proteases such as trypsin result in cell death. However, because at least a portion of the type I collagen molecule is sensitive to a variety of proteases, including trypsin, this cannot be the approach of choice for collagenous grafts intended for implant in high mechanical stress locations.

In some embodiments, the method for producing a DM includes the step of treatment with a nuclease, e.g., a DNase. Generally the nuclease treatment is performed during the decellularization step. In one embodiment, the cells are treated with nucleases to remove DNA and RNA. Nucleases are effective to inhibit cellular metabolism, protein production, and cell division without degrading the underlying collagen matrix. Nucleases that can be used for digestion of native cell DNA and RNA including both exonucleases and endonucleases. A wide variety of which are suitable for use in this step of the process and are commercially available. For example, exonucleases that effectively inhibit cellular activity include DNase I and RNase A (SIGMA Chemical Company, St. Louis, Mo.) and endonucleases that effectively inhibit cellular activity include EcoR I (SIGMA Chemical Company, St. Louis, Mo.) and Hind III (SIGMA Chemical Company, St. Louis, Mo.). In some aspects, the selected nucleases can be applied in a physiological buffer solution which contains ions, such as magnesium and calcium salts, which are optimal for the activity of the nuclease. In some aspects, the ionic concentration of the buffered solution, the treatment temperature, and the length of treatment are selected to assure the desired level of effective nuclease activity. The buffer can be hypotonic to promote access of the nucleases to the cell interiors.

Other enzymatic digestion can be suitable for use herein, for example, enzymes that disrupt the function of native cells in a transplant tissue can be used. For example, phospholipase, e.g. phospholipases A or C, in a buffered solution, can be used to inhibit cellular function by disrupting cellular membranes of endogenous cells. In some aspects, the enzyme employed does not have a detrimental effect on the extracellular matrix protein. The enzymes suitable for use can also be selected with respect to inhibition of cellular integrity, and also include enzymes which can interfere with cellular protein production. The pH of the vehicle, as well as the composition of the vehicle, can also be adjusted with respect to the pH activity profile of the enzyme chosen for use. Moreover, the temperature applied during application of the enzyme to the tissue can be adjusted in order to optimize enzymatic activity.

Subsequent to decellularization protocols, the resultant extracellular matrix can be washed at least once with suitable chemical solutions, such as saline, protease, enzymes, detergents, alcohols, acidic or basic solutions, salt solutions, etc., to assure removal of cell debris which can include cellular protein, cellular lipids, and cellular nucleic acid, as well as any extracellular debris such as lipids and proteoglycans. Optionally, an antibacterial, an antifungal, or a sterilant or a combination thereof, can be included in a wash solution to protect the matrix from contamination with environmental pathogens. In certain embodiments, the DM is sterilized by irradiation, ultraviolet light exposure, ethanol incubation (70-100%), treatment with glutaraldehyde, peracetic acid (0.1-1% in 4% ethanol), chloroform (0.5%), or antimycotic and antibacterial substances.

The DM prepared in accordance with the above can be free or substantially free of its native cells, and additionally, cellular and extra-cellular antigen components have been washed out of the extracellular matrix. In some aspects, the extracellular matrix has been treated in a manner which limits the generation of new immunological sites in the collagen matrix. In one embodiment, the DM is obtained as a slurry of small particles. This slurry can eventually be processed into an implant. In another embodiment, the DM is obtained as an entire or partial structure, such as a sheet, or a tubular member, such as a small intestine. In addition, the decellularized extracellular matrix can contain a significant portion of the original tissue mass retaining physical properties in regard to strength and elasticity and has components which are largely collagens but also comprise glycosaminoglycans and proteins closely associated with collagen such as the basement membrane complex, laminin, fibronectin, growth factors, and cytokines.

One aspect further provides the preservation of the decellularized extracellular matrix for later use. The decellularized extracellular matrix can be freeze-dried for prolonged storage. For example, DM-coated plates can be allowed to dry within a sterile biosafety cabinet for up to 12 h. In some aspects, dried plates with DM can be stored at room temperature in the dark for up to 1 month prior to use. Likewise, the decellularized extracellular matrix can be air-dried by any known standard techniques. In one embodiment, the decellularized extracellular matrix can be concentrated or dehydrated and later reconstituted or rehydrated, respectively, before use. The method can include drying the tissue culture substrate coated with DM before removal of the DM. Drying can occur, e.g., at room temperature for up to 12 hours in a biosafety cabinet. In other embodiments, drying is via lyophilization. If desired, the dried DM can be stored. In some embodiments, storage is up to 1 month, 2 months, 3 months, 4 months, 5 months, 6 months, or more.

In certain embodiments, the decellularized extracellular matrix is cryopreserved. General techniques for cryopreservation of cells are well-known in the art and are generally applicable to a DM (see, e.g., Doyle et al., (eds), 1995, Cell & Tissue Culture: Laboratory Procedures, John Wiley & Sons, Chichester; and Ho and Wang (eds), 1991, Animal Cell Bioreactors, Butterworth-Heinemann, Boston, each of which is incorporated herein by reference).

DM Separation and Preparation for Transfer to a Support.

As described above, in some aspects a DM is prepared attached (e.g. dried) to a substrate such as a tissue culture substrate. In some aspects, DM can be separated from a substrate. Separation can be performed via, e.g., treatment with an acidic solvent and/or mechanical removal (e.g., scraping) of the DM from the tissue culture substrate or lifting the DM from thermoresponsive polymers by reducing the temperature. For example, separating the DM from the tissue culture substrate can be done by treatment with 0.02 N acetic acid and scraping the ECM from the tissue culture substrate using a tissue culture scraper. As a further example, DM coated plates can be physically scraped, e.g., with a sterile plastic scraper. In some aspects, the scraping can be performed in the presence of acetic acid. In some aspects, the scraping can be performed in the presence of 0.02 N acetic acid. In some aspects, the scraping can be performed in the presence of less than 0.01, 0.01, 0.02, 0.03, 0.04, 0.05, 0.06, 0.07, 0.08, 0.09, 0.1 N or greater of acetic acid. In some aspects, cells and their ECM cultured on a thermoresponsive plate allows for the lifting of intact ECM from the dish while not necessarily promoting homogenization.

In some aspects, the separated DM is collected. In some aspects, the separated DM can be collected in an acidic solvent. In some aspects, the separated DM can be collected in acetic acid, e.g., at a concentration of acid described above. In some aspects, the separated DM can be transferred, e.g., to microcentrifuge tubes or a vessel. In some aspects, the separated and collected DM can be transferred, e.g., to microcentrifuge tubes or a vessel.

In some aspects, the methods described herein can include a step for dissociation, e.g., breaking up the ECM in the solution. Dissociating can be performed using, e.g., sonication and/or mechanical homogenization (for example, a mortar and pestle) and/or enzymatic treatment. In some aspects, the separated DM can be sonicated, e.g., with 2 second pulses 10-15 times to mechanically homogenize DM contents. In some aspects, a homogenizer is used for dissociation.

In yet another embodiment, the decellularized extracellular matrix is lyophilized. The lyophilized DM can be in the form of an implant which has pores. Characteristics of the pore structure can be controlled by process parameters.

In yet another embodiment, the decellularized extracellular matrix is formed as a gel. In some aspects, the proteins are temporarily and reversibly denatured. In yet another embodiment, the decellularized extracellular matrix is precipitated or co-precipitated with other proteins or biologics.

DM can be characterized using methods known in the art. In some aspects, DM can have a protein content of about less than 10, 10, 11, 12, 13, 14, 15, 16, 17, 18, 19, 20, 21, 22, 23, 24, 25, 26, 27, 28, 29, 30, $\mu g/cm^2$ or greater (e.g., 10-20 $\mu g/cm^2$). In some aspects, DM can have 95, 96, 97, 98, or 99% less DNA as compared to a non-decellularized ECM control sample. In some aspects, DM can express type 1 collagen, fibronectin, biglycan, and/or decorin. In some aspects, DM is fibrous. In some aspects, DM includes proteins and/or polysaccharides. Other characterizations of DM are described in the Examples section below.

Accordingly, described herein are methods for producing a composition comprising a decellularized extracellular matrix (DM) produced in tissue culture. The method includes the steps of a) growing a population of cells on a tissue culture substrate under conditions sufficient to form an extracellular matrix (ECM); b) removing the cells from the tissue culture substrate to form tissue culture substrate coated with DM; c) separating the DM from the tissue culture substrate into a solvent to form a solution comprising the ECM; and d) dissociating the DM in the solution, thereby producing a composition comprising the decellularized ECM. For example, to generate osteogenic (bone-inducing) DMs, MSCs are seeded at high density (greater than or equal to 50,000 cells/sq. cm) and maintained in ambient oxygen (21% $O_2$) in alpha modified Eagle's medium supplemented with 50 µg/ml ascorbate-2-phosphate for 15 days. Next, wells are rinsed with PBS and treated with 0.5% Triton X-100 in 20 mM $NH_4OH$ in PBS for 5 min at 37° C. Wells are rinsed with PBS and treated with DNAse (200 units/mL PBS) for 1 h at 37° C. Following additional PBS rinsing, plates are allowed to dry within a sterile biosafety cabinet for up to 12 h. Matrix-coated plates are stored at room temperature in the dark for up to 1 month prior to use. To solubilize the DM, wells are incubated in 0.02N acetic acid, scraped into a container, e.g., a test tube, and dissociated via sonication and/or mechanical homogenization. After determination of protein concentration, the DM suspension is resuspended to a known concentration, sterilely pipeted on the 3D polymeric biomaterial of interest, and then allowed to dry in the biosafety cabinet. DM-coated scaffolds are then ready for seeding with cells or implantation. Similar DMs can be generated to promote the formation of other tissues including capillaries, muscle, cornea, liver, and epithelium.

Supports, Transfer, and Uses of DM.

In some aspects, DM can be transferred, e.g., to a support. Thus, the methods are useful for coating supports (e.g., biomaterials) with DM. Supports can be, e.g., solid or gelatinous. In particular, the methods are useful for DM coating of 3D materials where nutrient and oxygen access are potential problems for cell growth. The methods can be used for fabrication of implants to guide tissue formation or to produce substrates for the study of cellular behavior, e.g., tissue culture substrates. This invention has the ability to accelerate tissue formation, improve cellular viability upon implantation, enhance biomaterial integration once implanted, and provide a platform to better model cellular behavior in vivo.

Also provided are methods for repairing, regenerating or strengthening cells, tissues or organs. In some aspects, a decellularized extracellular matrix is combined with a support. In particular, included herein are methods for formulating the decellularized extracellular matrix as part of one or more supports such as pharmaceutical compositions, implants, tissue regeneration scaffolds, and medical devices. Although decellularized extracellular matrix of cells is described in detail, it is not necessary that the decellularized extracellular matrix be of cells. For example, the decellularized extracellular matrix can be of tissue. Accordingly, although some of the uses of the decellularized extracellular matrix can be described as a use for a decellularized extracellular matrix of cells, decellularized extracellular matrix of non-cells, e.g., a tissue can alternatively be used.

In certain embodiments, the decellularized extracellular matrix can be used to treat defective, diseased, damaged or ischemic tissues or organs which include, but are not limited to, head, neck, eye, mouth, throat, esophagus, chest, bone, ligament, cartilage, tendons, lung, colon, rectum, stomach, prostate, pancreas, breast, ovaries, fallopian tubes, uterus, cervix, testicles or other reproductive organs, hair follicles, skin, diaphragm, thyroid, blood, muscles, bone marrow, heart, lymph nodes, blood vessels, large intestine, small intestine, kidney, liver, pancreas, brain, spinal cord, and the central nervous system.

In particular, the decellularized extracellular matrix can be used to treat diseases that can benefit from improved angiogenesis, cell proliferation and tissue regeneration. Such diseases or conditions include, but are not limited to, burns, ulcer, trauma, wound, bone fracture, diabetes, psoriasis, arthritis, asthma, cystitis, inflammation, infection, ischemia, restenosis, stricture, atherosclerosis, occlusion, stroke, infarct, aneurysm, abdominal aortic aneurysm, uterine fibroid, urinary incontinence, vascular disorders, hemophilia, cancer, and organ failure (e.g., heart, kidney, lung, liver, intestine, etc.).

In some aspects, DM can be used to regenerate or replace at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, at least 10%, at least 5%, or at least 1% of defective, diseased, damaged or ischemic cells from the affected tissue or organ. The methods described herein are provided for an animal, including but not limited to mammals such as a non-primate (e.g., cows, pigs, horses, chickens, cats, dogs, rats, etc.), and a primate (e.g. monkey such as a cynomolgous monkey and, e.g., a human). In one embodiment, the subject is a human.

Pharmaceutical Compositions

The DM produced by the method of the invention can be applied to a support. In one aspect, the support is a pharmaceutical composition. The decellularized extracellular matrix of cells can be formulated into pharmaceutical compositions that are suitable for administration to a subject. Such compositions comprise a prophylactically or therapeutically effective amount of the decellularized extracellular matrix as disclosed herein, and a pharmaceutically acceptable carrier. In some aspects, a pharmaceutical composition includes an alginate hydrogel.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a carrier that can be used when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Other examples of suitable pharmaceutical vehicles are described in "Remington: the Science and Practice of Pharmacy", 20th ed., by Mack Publishing Co. 2000.

Generally, the ingredients of compositions are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed from an infusion bottle containing sterile pharmaceutical grade water or saline. Where the composition is administered by injection, an ampule of sterile water for injection or saline can be provided so that the ingredients can be mixed prior to administration.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known and can be used to administer the compositions, e.g., encapsulation in microbeads, liposomes, microparticles, microcapsules, receptor-mediated endocytosis (see, e.g., Wu and Wu, 1987, J. Biol. Chem. 262:4429-4432), etc. Methods of administering a prophylactic or therapeutic amount of the compositions include, but are not limited to, parenteral administration (e.g., intradermal, intramuscular, intracoronary, intraperitoneal, intravenous and subcutaneous), epidural, and mucosal (e.g., intranasal, inhaled, and oral routes). The composition comprising decellularized extracellular matrix of cells can be administered by any convenient route, for example, by infusion or bolus injection, by absorption through epithelial or mucocutaneous linings (e.g., oral mucosa, rectal and intestinal mucosa, etc.) and can be administered together with other biologically active agents or cells such as MSCs. Administration can be systemic or local.

In another embodiment, the decellularized extracellular matrix can be delivered in a controlled release or sustained release system. In one embodiment, a pump can be used to achieve controlled or sustained release (see Langer, 1990, Science 249:1527-1533; Sefton, 1987, CRC Crit. Ref Biomed. Eng. 14:20; Buchwald et al., 1980, Surgery 88:507; Saudek et al., 1989, N. Engl. J. Med. 321:574). Any technique known to one of skill in the art can be used to produce sustained release formulations comprising the decellularized extracellular matrix of the invention. See, e.g., U.S. Pat. No. 4,526,938; International Publication Nos. WO 91/05548 and WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760, each of which is incorporated herein by reference in its entirety. In another embodiment, the decellularized extracellular matrix is configured to be controllably released. For example, the decellularized extracellular matrix can be configured to be resorbed by the body of the patient at a predetermined rate. Accordingly, the body of the patient will receive the therapeutic benefits of the decellularized extracellular matrix at the predetermined rate.

In another embodiment, polymeric materials can be used to achieve controlled or sustained release of the decellularized extracellular matrix material (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. Nos. 5,679,377; 5,916,597; 5,912,015; 5,989,463; and 5,128,326; International Publication Nos.

WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glucosides) (PLGA), and polyorthoesters. In some aspects, the polymer used is PLG. In one embodiment, the polymer used in a sustained release formulation is inert, free of leachable impurities, stable during storage, sterile, and biodegradable. In yet another embodiment, a controlled or sustained release system can be placed in proximity to the target, thus requiring only a fraction of the systemic dose (see, e.g., Goodson, 1984, in Medical Applications of Controlled Release, supra, vol. 2, pp. 115-138).

The amount of the pharmaceutical composition which will be effective in the treatment of a particular disorder or condition will depend on the nature of the disorder or condition, and can be determined by standard clinical techniques. In addition, in vitro assays and animal models can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses can be extrapolated from dose-response curves derived from in vitro or animal model test systems.

Implants

In other aspects, the support includes an implant. Also included in the invention are methods for making and implanting an implant comprising decellularized extracellular matrix. The implants can be, without limitation: (1) vascular implants, such as carotid artery replacement, and general vein and artery replacement in the body; (2) heart valves and patches; (3) burn dressings and coverings; (4) muscle, tooth and bone implants; (5) pericardium and membranes; (6) myocardial patch; (7) urethral sling; and (8) fiber for filling aneurysms.

In one embodiment, the implant is a tubular member. The decellularized extracellular matrix is processed into tubular or cylindrical form. The tubular member can be used, for example, to create an esophagus, a vein, an artery, or any other tubular body member. The tubular member can be implanted or placed into a damaged area of a body of a patient. The decellularized extracellular matrix will be resorbed as native or host tissue (tissue produced by the body of the patient) forms. In some cases, the host tissue is functional, vascularized, and morphologically similar to the normal tissue.

In one embodiment of the tubular member, an elastomeric biocompatible polymer is applied to the tubular member. For example, the elastomeric biocompatible polymer can be applied to the tubular member via a spray, glue or other adhesive, radio frequency welding, staples, or any other known method. The elastomeric biocompatible polymer gives the tubular member elasticity and strength.

The elastomeric biocompatible polymer can be a nonporous material or a porous material. For example, the polymer can be a porous material if exchange of fluids and nutrients with the tissues of the patient that surround the implanted tubular member is required. Additionally, the elastomeric biocompatible polymer can be biostable or degradable. For example, a biostable elastomeric biocompatible polymer is used to provide rigidity and elasticity to the tubular member throughout the life of the patient. Examples of the elastomeric biocompatible polymer are silicones (e.g. polysiloxanes and substituted polysiloxanes), polyurethanes, thermoplastic elastomers, ethylene vinyl acetate copolymers, polyolefin elastomers, styrene isobutylene block copolymers, and EPDM rubbers.

In one embodiment, the elastomeric biocompatible polymer is applied to only the outer surface of the tubular member. In another embodiment, the elastomeric biocompatible polymer is applied to only the inner surface of the tubular member. In a further embodiment, the elastomeric biocompatible polymer is applied to both the inner and the outer surfaces of the tubular member.

The implants comprising decellularized extracellular matrix can be implanted in vivo at the site of tissue damage to promote repair, regeneration and/or strengthening. In addition, the materials and methods described herein are useful to promote the in vitro culture and differentiation of cells and tissues.

Biocompatible Materials and Tissue Regeneration Scaffolds

In some aspects, a support is a biocompatible material such as a tissue regeneration scaffold. One aspect provides for the incorporation of the decellularized extracellular matrix into a biocompatible material for implantation into a subject. In one embodiment, the biocompatible material is in the form of a scaffold.

The scaffold can be of natural collagen, decellularized, conditioned extracellular matrix, or synthetic polymer. In certain embodiments, the scaffold serves as a template for cell proliferation and ultimately tissue formation. In a specific embodiment, the scaffold allows the slow release of the decellularized extracellular matrix into the surrounding tissue. As the cells in the surrounding tissue begin to multiply, they fill up the scaffold and grow into three-dimensional tissue. Blood vessels then attach themselves to the newly grown tissue, the scaffold dissolves, and the newly grown tissue eventually blends in with its surrounding.

Medical Device Comprising Decellularized Extracellular Matrix

In some aspects, the support includes a medical device. The decellularized extracellular matrix can be used to form medical devices or prosthetic devices, such as a stents, artificial hearts, screws, staples, or clips, which can be implanted in the subject. In one embodiment, the decellularized extracellular matrix can be incorporated into the base material needed to make the medical or prosthetic device. In another embodiment, the decellularized ECM material can be used to coat or cover the medical or prosthetic device.

The medical and prosthetic devices can be inserted or implanted into the body of a patient.

Method of Forming a Medical Device Using Decellularized Extracellular Matrix

In one embodiment, the decellularized extracellular matrix can be compression molded to form the medical or prosthetic device. Any known method of compression molding can be used. For example, in one embodiment, the decellularized extracellular matrix in a slurry form is poured into a medical or prosthetic device mold. Pressure is then applied to the decellularized extracellular matrix. Once the decellularized extracellular matrix has cured it is removed from the mold. The molded decellularized extracellular matrix can then be inserted or implanted into the body of a patient. In one embodiment, a binder, such as fibrin glue, is mixed or otherwise incorporated with the decellularized matrix. In another embodiment, the decellularized extracellular matrix or the collagen of the matrix is cross-linked, such as via ultra-violet light or extreme dehydration, after the compression of the material. In yet another embodiment, the collagen of the decellularized extracellular matrix is reversibly denatured during the compression stage and is then reversed after the compression stage. For example, the collagen can have a pH of less than 4 during compression and a pH of about 7.4 after compression.

Types of Medical Devices for Coating

Medical devices can be made of any biocompatible material suitable for medical devices in general which include without limitation natural polymers, synthetic polymers, ceramics, and metallics. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys.

Metallic materials can be made into elongated members or wire-like elements and then woven to form a network of metal mesh. Polymer filaments can also be used together with the metallic elongated members or wire-like elements to form a network mesh. If the network is made of metal, the intersection can be welded, twisted, bent, glued, tied (with suture), heat sealed to one another; or connected in any manner known in the art.

The polymer(s) useful for forming the medical device should be ones that are biocompatible and avoid irritation to body tissue. They can be either biostable or bioabsorbable. Suitable polymeric materials include without limitation polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins. Other polymers that are useful as materials for medical devices include without limitation dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(epsilon-caprolactone), poly(beta-hydroxybutyrate), polydioxanone, poly(gamma-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of molecules, such as proteins, nucleic acids, and the like.

Furthermore, although the invention can be practiced by using a single type of polymer to form the medical device, various combinations of polymers can be employed. The appropriate mixture of polymers can be coordinated to produce desired effects when incorporated into a medical device. In certain preferred embodiments, the decellularized extracellular matrix is mixed with a polymer.

The decellularized extracellular matrix can also be used alone or in combination with a polymer described above to form the medical device. The decellularized extracellular matrix can be dried to increase its mechanical strength. The dried decellularized extracellular matrix can then be used as the base material to form a whole or part of the medical device. In some embodiments, the decellularized extracellular matrix constitutes at least 5%, at least 10%, at least 25%, at least 50%, at least 80%, at least 90%, at least 95%, at least 99% by weight or by size of the medical device.

Examples of the medical devices include, but are not limited to, stents, surgical staples, catheters (e.g., central venous catheters and arterial catheters), guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, and extra-corporeal devices such as blood oxygenators, blood filters, hemodialysis units, hemoperfusion units and plasmapheresis units.

Medical devices include those that have a tubular or cylindrical-like portion. The tubular portion of the medical device need not to be completely cylindrical. For instance, the cross-section of the tubular portion can be any shape, such as rectangle, a triangle, etc., not just a circle. Such devices include, without limitation, stents and grafts. A bifurcated stent is also included among the medical devices which can be fabricated by the method of the present invention.

Medical devices which are particularly suitable for the present invention include any kind of stent for medical purposes which is known to the skilled artisan. Suitable stents include, for example, vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

Methods of Coating the Medical Device

In some aspects, the decellularized extracellular matrix, e.g., in combination with a biologically active material, can be applied by any method to a surface of a medical device to form a coating. Examples of suitable application methods are spraying, laminating, pressing, brushing, swabbing, dipping, rolling, electrostatic deposition and all modern chemical ways of immobilization of bio-molecules to surfaces. In some aspects, the decellularized extracellular matrix is applied to a surface of a medical device by spraying, rolling, laminating, and pressing. In one embodiment, more than one coating method can be used to make a medical device. In certain embodiments, the decellularized extracellular matrix is placed into a carrier in order to apply it to the device surface. Non-limiting examples of carriers include SIBS, PLGA, PGA, collagen (all types), etc.

Furthermore, before applying the coating composition, the surface of the medical device is optionally subjected to a pre-treatment, such as roughening, oxidizing, sputtering, plasma-deposition or priming in embodiments where the surface to be coated does not comprise depressions. Sputtering is a deposition of atoms on the surface by removing the atom from the cathode by positive ion bombardment through a gas discharge. Also, exposing the surface of the device to a primer is a possible method of pre-treatment.

Coating compositions suitable for applying coating materials to the devices can include a polymeric material and a biologically active material dispersed or dissolved in a solvent suitable for the medical device, which are known to the skilled artisan. The solvents used to prepare coating compositions include ones which can dissolve the polymeric material into solution or suspend the polymeric material and do not alter or adversely impact the therapeutic properties of the biologically active material employed. For example, useful solvents for silicone include tetrahydrofuran (THF), chloroform, toluene, acetone, isooctane, 1,1,1-trichloroethane, dichloromethane, and mixture thereof.

The polymeric material should be a material that is biocompatible and avoids irritation to body tissue. In some aspects, the polymeric materials used in the coating composition are selected from the following: polyurethanes, silicones (e.g., polysiloxanes and substituted polysiloxanes), and polyesters. Also preferable as a polymeric material is styrene-isobutylene-styrene (SIBS). Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, and combinations of the foregoing.

More preferably for medical devices which undergo mechanical challenges, e.g. expansion and contraction, the polymeric materials can be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating composition is capable of undergoing deformation under the yield point when the device is subjected to forces, stress or mechanical challenge.

In certain embodiments, the medical device is covered with one coating layer. In certain other embodiments, the medical device is covered with more than one coating layer. In some embodiments, the medical device is covered with different coating layers. For example, the coating can comprise a first layer and a second layer that contain different materials. Alternatively, the first layer and the second layer can contain an identical material having different concentrations. In one embodiment, either the first layer or the second layer can be free of biologically active material.

It must be noted that, as used in the specification and the appended claims, the singular forms "a," "an" and "the" include plural referents unless the context clearly dictates otherwise.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Coating Biomaterials with Decellularized ECM

Mesenchymal stem cells (MSCs) secrete an extracellular matrix (ECM) onto their culture surface which can be retained following detergent-based decellularization. It has been previously demonstrated the bioactive nature of this residual decellularized matrix (DM) through its capacity to modulate the attachment, proliferation, and osteogenic differentiation of secondary progenitor cell populations cultured upon it. While such residual DMs have been fairly simple to manufacture and test in 2D, mass transport issues limit the ability of cells to deposit homogenous ECM coatings throughout porous 3D biomaterial constructs, such as those commonly utilized in skeletal tissue engineering. Here it is shown that DMs produced in large quantity in 2D retain their biological properties following removal, mechanical homogenization, and application to a new surface, thus providing a method of coating more complex material structures with a homogenous layer of bioactive MSC-deposited ECM.

Human MSCs were cultured on tissue culture plastic (TCP) for 2 weeks and then decellularized with 0.5% Triton X-100. The residual ECM was then scraped from the surface with a sterile scraper into 0.02N acetic acid. The resulting EM solution was broken down into smaller pieces via sonication. The DM was then transferred at different concentrations to new TCP (tDM) and allowed to adhere. Amido black protein quantification was used to measure and confirm protein levels on coated tDM.

Naïve populations of human MSCs were cultured on tDM-coated TCP to assess their osteoinductive properties.

Figure 2:
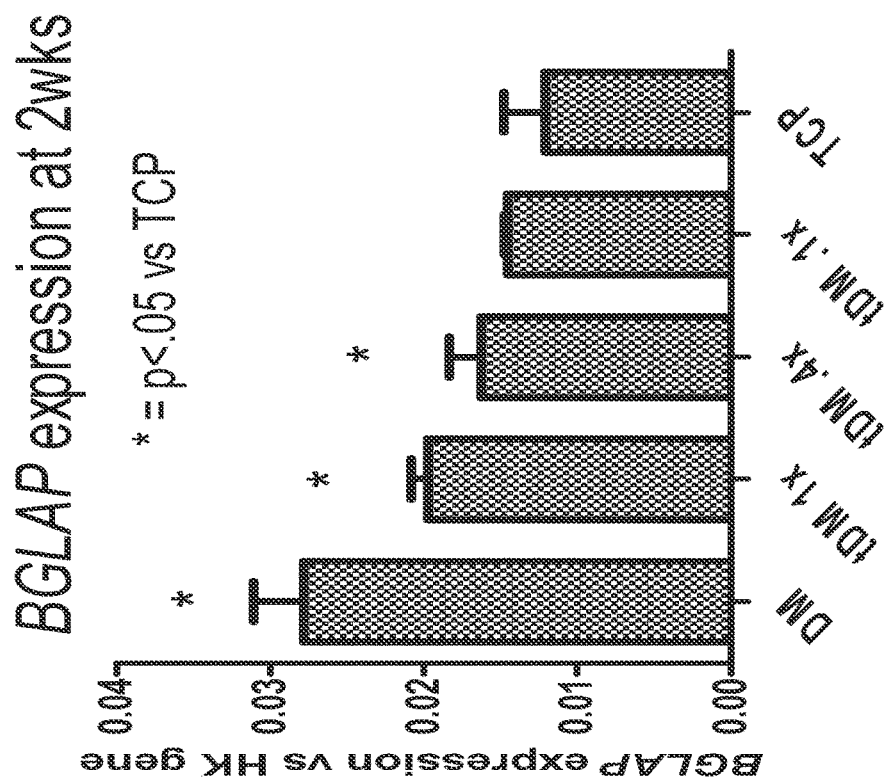
FIG. 2 shows qPCR results for osteocalcin (BGLAP) expression from hMSCs cultured on tDMs.

As shown in FIGS. 1 and 2, qPCR results confirmed a significant and dose dependent increase in osterix (SP7) and osteocalcin (BGLAP) expression from hMSCs cultured on tDMs. Expression levels were significantly lower than those found on traditional DMs.

Figure 3:
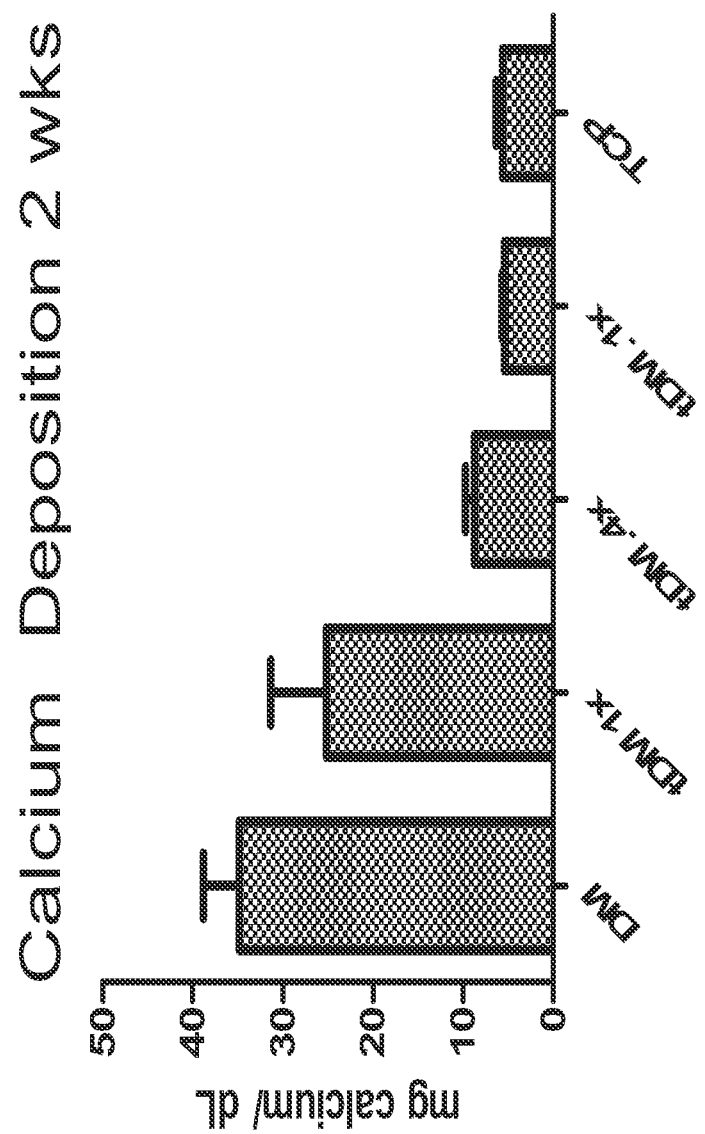
FIG. 3 shows calcium quantification from hMSCs cultured on tDMs at 2 weeks.
Figure 4:
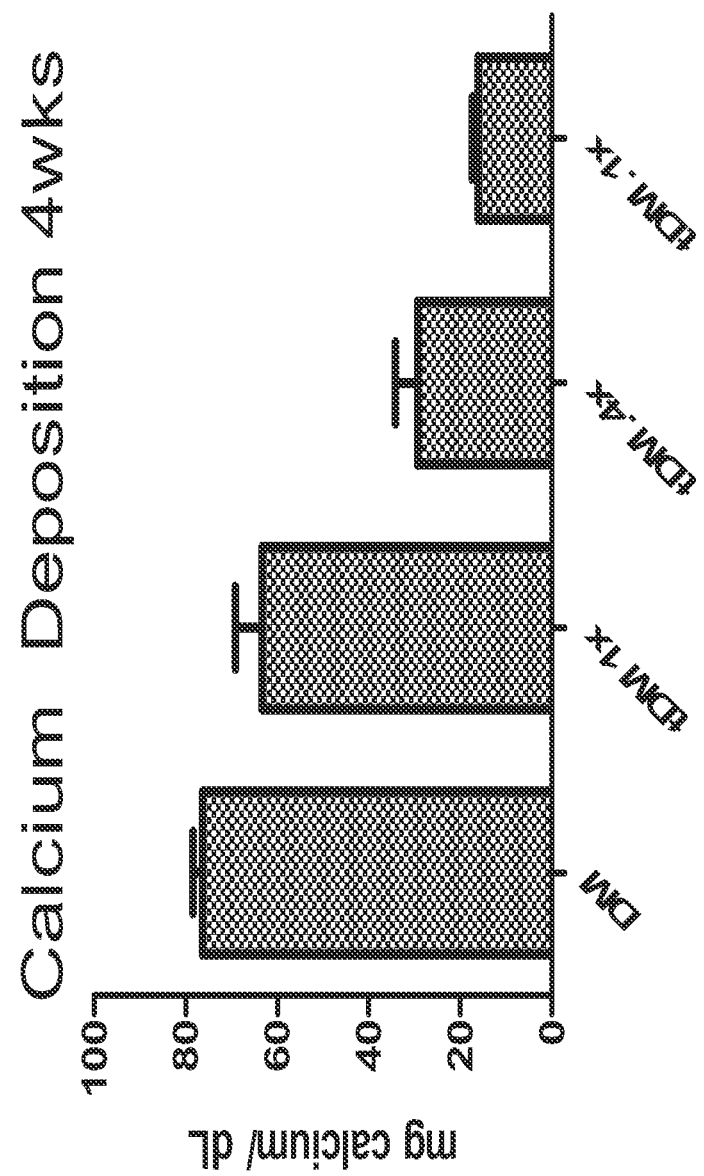
FIG. 4 shows calcium quantification from hMSCs cultured on tDMs at 2 weeks.

As shown in the FIGS. 3 and 4, calcium quantification revealed a significant and dose dependent increase in mineral deposition from hMSCs cultured on tDMs. Mineralization levels were similar to those from hMSCs cultured on traditional DMs.

The preliminary results demonstrate that naïve hMSCs cultured on tDM-coated TCP display significantly accelerated calcium deposition and osteogenic gene expression when compared to cells cultured on TCP alone. The efficacy of tDMs to drive MSC osteogenesis was somewhat muted in comparison to the original DMs. There was a dose dependent osteogenic response from the naïve MSCs cultured on tDMs of differing concentration. These results demonstrate an example of a bioactive biomaterial constructs for skeletal tissue engineering which have the ability to better interface with host tissue and ultimately drive cell behavior.

Decellularized matrices retain the capacity to drive hMSC osteogenic differentiation following removal from one surface and deposition on another. tDM coatings were also observed to influence hMSCs in a dose dependent manner. These results provide a novel approach toward the design of more bioactive materials for use in the field of skeletal tissue engineering.

Example 2

Coating Gelatin Microbeads with Decellularized ECM (DM)

As an alternative to autograft bone, there is an increasing demand for osteoconductive and osteoinductive materials that can be delivered in a minimally invasive manner. The transplantation of osteogenic cells in alginate hydrogels can promote bone and cartilage formation in vivo (see ref 1). Although highly cytocompatible, these hydrogels require appropriate cues (e.g., adhesion peptides and extracellular cues) to direct bone formation. It has been demonstrated that an engineered cell-secreted extracellular matrix (ECM) deposited by human mesenchymal stem cells (hMSCs) markedly increased the osteogenic differentiation of naïve hMSC (see ref 2). Here it is shown that presentation of a decellularized ECM (DM) on micron-sized substrata suspended in alginate gels retained the injectability of such materials while presenting physical and chemical cues to stimulate osteogenic differentiation. Moreover, the successful use of microcarrier beads in these hydrogels represents a new approach to promote cell attachment and instruct neighboring cells, potentially obviating the need for chemically bonding adhesive peptides to the polymer backbone.

Materials and Methods: An osteogenic DM was generated by culturing hMSCs on tissue culture plastic in alpha-MEM with 50 μg/ml ascorbate-2-phosphate for 15 days, followed by a decellularization protocol as previously described (see ref 2, the method is incorporated by reference). The cell-secreted DM was collected in 0.02N acetic acid and used to coat pre-swelled gelatin microbeads (Cytodex®) at a concentration of 15 μg protein/mg bead. The presence of DM on the beads was visualized with scanning electron microscopy (SEM). hMSCs ($5 \times 10^6$) were mixed with 1 ml of 2% (w/v) alginate (MVG, Pronova) containing 15 mg of DM-coated beads and CaSO4 as a cross-linker. The mix was allowed to gel for 1 h between two glass plates, and a biopsy punch was used to generate punchouts of 8 mm diameter and 2 mm thickness. Control groups included alginate gels loaded with uncoated or heat-inactivated DM-coated beads. Gels were cultured in osteogenic media for up to 4 weeks. Cell morphology was observed by calcein stain at 24 and 48 h. Stiffness of acellular gels was measured by compressive testing. Osteogenic differentiation of naïve MSCs was analyzed using biochemical assays for alkaline phosphatase, cell proliferation, calcium deposition, and qPCR.

Figure 5:
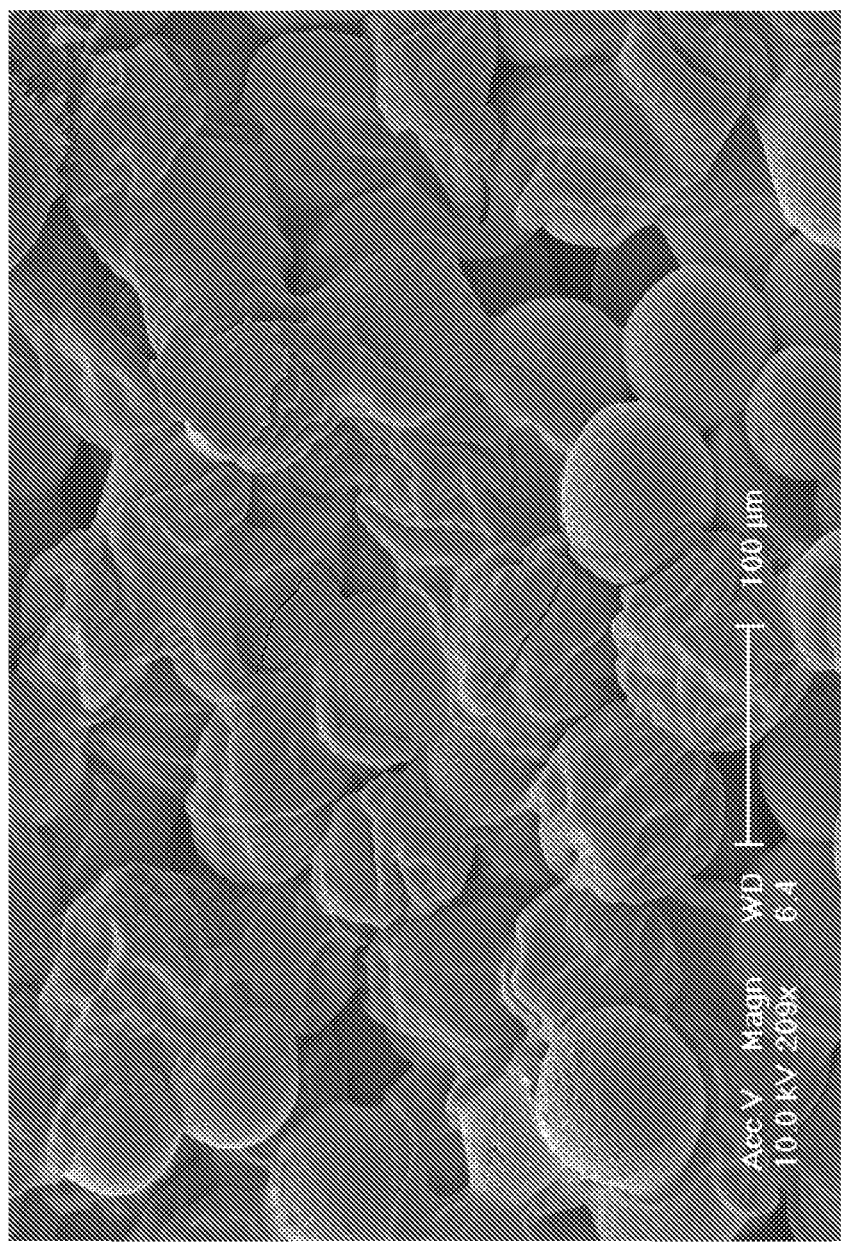
FIG. 5 shows an SEM image of ECM protein coating on cytodex beads.
Figure 6:
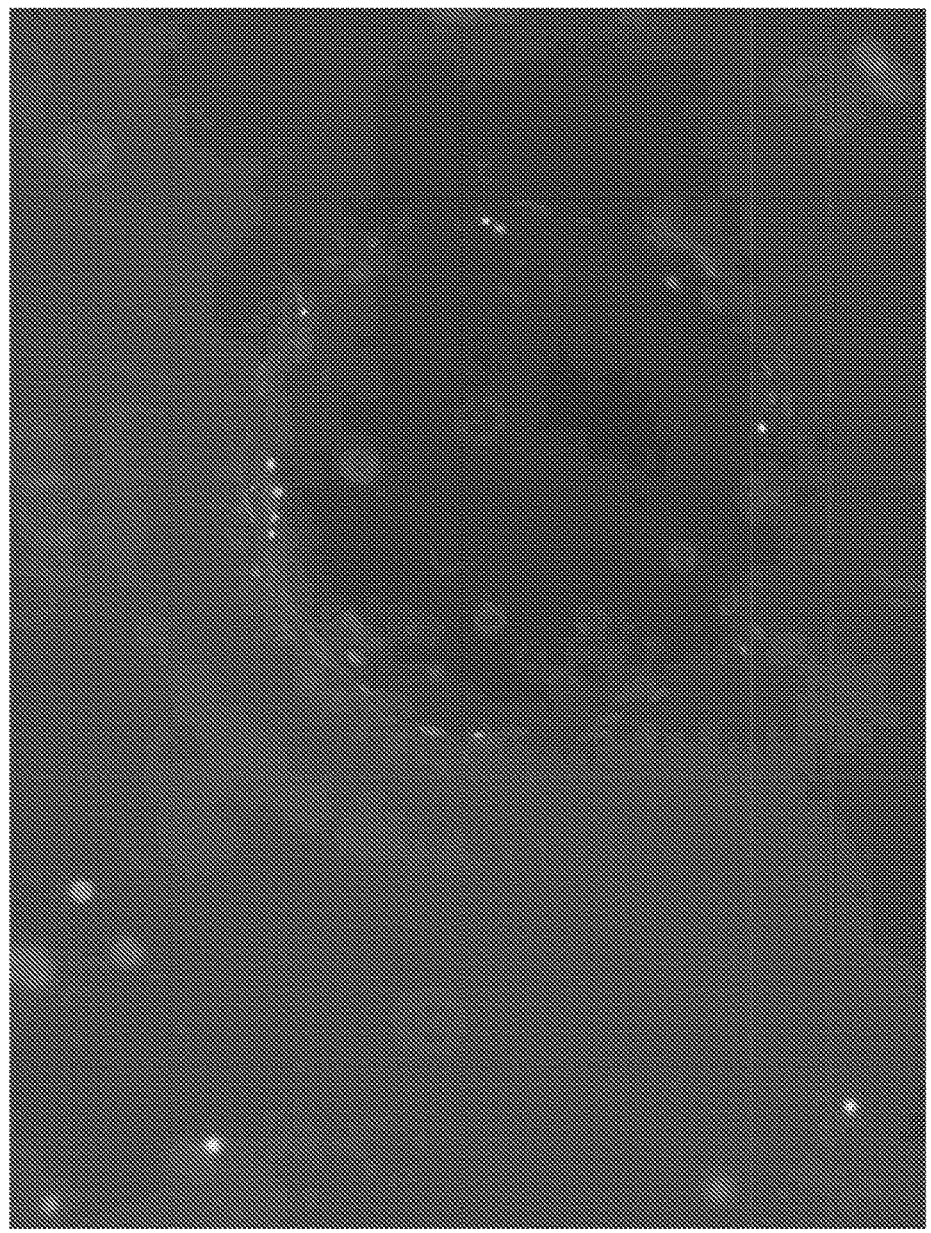
FIG. 6 shows a calcein stain showing hMSC attachment to cytodex bead in alginate gel after 48 h (100×). Scale bar represents 50 μm.

Results: A substantial matrix deposition was detected on gelatin beads under SEM (FIG. 5). Calcein stain demonstrated attachment and spreading of cells to the DM-coated beads after 48 h (FIG. 6), while cells not in contact with the bead retained a circular morphology. Stark differences were detected in cell migration and cell proliferation on gels with DM-coated beads. This cell response also mediated the differentiation of naïve hMSCs towards osteogenic lineage.

Conclusion: The results demonstrate that DM-coated microbeads suspended in alginate hydrogels can instruct cell phenotype. The DM-coated microbeads can be used in an injectable system for treating bone defects.

Example 3

Engineering Cell-Secreted Matrices for Directing Osteogenic Differentiation

Materials and Methods
Cell Culture

Human bone marrow-derived MSCs (hMSCs, Lonza, Walkersville, Md.) were expanded without further characterization in alpha minimum essential medium (α-MEM, Invitrogen, Carlsbad, Calif.) supplemented with 10% fetal bovine serum (JR Scientific, Woodland, Calif.) and 1% penicillin and streptomycin (Mediatech, Manassas, Va.). Cells were cultured under standard conditions and utilized at passages 3-5. Medium was further supplemented with 50 μg/mL ascorbate-2-phosphate (A2P) for one passage prior to experimental use to prime cells for enhanced matrix deposition.[10] For studies examining the role of oxygen tension, the oxygen microenvironment was controlled as previously described using airtight chambers (Billups-Rothenberg, Del Mar, Calif.). See Decaris, M. L., C. I. Lee, M. C. Yoder, A. F. Tarantal, and J. K. Leach. Influence of the oxygen microenvironment on the proangiogenic potential of human endothelial colony forming cells. Angiogenesis. 2009.

Design of Experiments Model

A Box-Behnken experimental design was created with Design-Expert 8 software (Stat-Ease, Minneapolis, Minn.) to analyze the contribution of three continuous variables (seeding density, culture duration, oxygen tension) and one discrete variable (media supplementation) towards the ability of hMSC-secreted matrices to direct hMSC osteogenic differentiation. Continuous variables were examined at low, medium and high levels with a centrally repeated condition. Linear, quadratic, and two-factor interactions of each variable were assessed.

Preparation of Decellularized ECMs (DMs)

hMSCs were cultured on 12-well plates under DOE-prescribed conditions with media changes performed every 3 d. Cells were seeded at densities from 2e4 to 8e4 cells/cm² and allowed to attach overnight. Plates were then cultured for 3 to 15 d at oxygen tensions ranging from 5% to 21% in either supplemented media (SM: α-MEM+50 μg/mL A2P) or osteogenic media (OM: α-MEM+10 mM β-glycerophosphate, 50 μg/mL A2P, 10 nM dexamethasone). Wells were then decellularized in a manner similar to that previously described.[9] Briefly, wells were rinsed with PBS and treated with 0.5% Triton X-100 (Sigma, St Louis, Mo.) in 20 mM NH$_4$OH in PBS for 5 min at 37° C. Wells were rinsed with PBS and treated with DNAse (Sigma, 200 units/mL PBS) for 1 h at 37° C. Following additional PBS rinsing, plates were allowed to dry within a sterile biosafety cabinet for up to 12 h. Matrix-coated plates were stored at room temperature in the dark for up to 1 month prior to use. Plates coated with fibronectin (Sigma, 0.5 ml of 25 μg/ml solution for 2 h) and untreated TCP served as control substrates.

Characterization of Decellularized Matrices

Decellularization of 12-well plates was assessed via uptake of calcein AM (AnaSpec, Fremont, Calif.) and DNA quantification. Briefly, 1 mL of calcein solution (3 μg/mL in α-MEM) was added to cell layers both pre- and post-decellularization for 15 min at 37° C. Calcein fluorescence was quantified using a microplate reader (BioTek, Winooski, Vt.) at 485/530 nm and imaged using a Nikon Eclipse TE2000-U fluorescent microscope. DNA content was quantified using the Quant-iT PicoGreen dsDNA Assay Kit (Invitrogen, Carlsbad, Calif.) and microplate reader as described.[24]

The morphology of hMSC-secreted ECMs was characterized by scanning electron microscopy after culture on Thermanox plastic coverslips (Nunc, Rochester, N.Y.) over 2 weeks as described.[39] Cytochemical staining of 12-well plates was performed by fixing cultures and decellularized matrices with 2% formaldehyde followed by rinsing in PBS. Plates were then stained for total protein with 0.1% coomassie brilliant blue in 80% $H_2O$/20% methanol (MP, Solon, Ohio) for 15 min. Cell layers and decellularized matrices were also stained for glycosaminoglycan content. Wells were rinsed with 1% acetic acid followed by incubation for 15 min with 1% Alcian Blue 0.1N HCl (Sigma).

Osteogenic Response of Naïve hMSCs
qPCR Analysis hMSCs were seeded onto decellularized ECM-coated, fibronectin-coated, or uncoated TCP wells in SM at 7500 cells/cm$^2$ and allowed to attach overnight. Culture medium was refreshed with OM the following day, and cells were cultured in standard conditions for 3 to 21 d. Total RNA was collected using the RNeasy Mini kit (Qiagen, Valencia, Calif.) and 250-500 ng of total RNA was then reverse-transcribed with the QuantiTect Reverse Transcription Kit (Qiagen). qPCR was performed using TaqMan1 Universal PCR Master Mix (Applied Biosystems, Foster City, Calif.) on a Mastercycler1 realplex2 (Eppendorf, Westbury, N.Y.); primers and probes for BGLAP (Hs01587814_g1), COL1A1 (Hs01076777_m1), IBSP (Hs00173720_m1), MRPL13 (Hs00204173_m1), RUNX2 (Hs00231692_m1), and SP7 (Hs01866874_s1) were purchased from Applied Biosystems. Amplification conditions were 50° C. for 2 min, 95° C. for 10 min, followed by 40 cycles at 95° C. for 15 s and 60° C. for 1 min. Quantitative PCR results were normalized to RPL13 transcript level to yield ΔCt. Fold change in expression was then calculated using the formula $2^{\Delta Ct}$ and fold changes between experimental groups and control wells calculated to yield ΔΔCt.

Alkaline Phosphatase Activity and Calcium Deposition hMSCs were seeded onto decellularized matrix-coated, fibronectin-coated, and uncoated TCP wells as described above. Intracellular alkaline phosphatase (ALP) activity was quantified and normalized to sample DNA content.[15] Unseeded decellularized matrices were analyzed at each timepoint as a control to distinguish intracellular ALP from ALP deposited and retained within the matrix, and ALP results were normalized to these control values. The distribution of mineralized deposits on the ECMs was analyzed qualitatively by alizarin red staining, while calcium deposition at 0, 1, 3, and 5 weeks was analyzed quantitatively as previously described.[15,24]

Cell Proliferation, Viability, and Attachment

To assess the contribution of distinct ECMs toward cellular proliferation and viability, hMSCs were seeded onto decellularized matrix-coated, fibronectin-coated, and uncoated TCP wells in SM at 4000 cells/cm$^2$, allowed to attach overnight, and cultured in OM as described above. Cell proliferation was measured by quantifying DNA concentration in each well at 1, 4, and 7 days. Cell viability was quantified by measuring metabolic activity with a 10% solution of alamarBlue (AbD Serotec, Raleigh, N.C.) for 3 h at 1, 4, and 7 days.[24] In addition, cell viability was examined under stressful conditions. Briefly, hMSCs were seeded onto each experimental surface at 50,000 cells/cm$^2$, allowed to attach overnight, and cultured in hypoxia chambers (1% $O_2$) for 24 h with serum-free media. Cell viability was assayed via calcein uptake. To characterize the ability of cells to attach to each substrate, hMSCs were seeded at 50,000 cells/cm$^2$ in SM and allowed to attach to culture surfaces for 1 or 4 h. Wells were then rinsed with PBS and cell retention was quantified by calcein uptake.

Statistical Analysis

Data are presented as mean±standard error unless otherwise stated. Statistical analysis was performed using paired Student's t-tests and one-way ANOVA where applicable. Statistical analysis of DOE experiments was performed by Design-Expert 8 software (Stat-Ease). P values less than 0.05 were considered statistically significant.

Results
Design of Experiments Model

A DOE-based approach was utilized to examine the effect of culture conditions when producing hMSC-secreted decellularized matrices (DMs) to direct the osteogenic potential of naïve hMSCs. Four distinct culture variables (Table 1) were input into a Box-Behnken experimental design, resulting in 13 unique culture environments for creating distinct DMs. The osteogenic and proliferative responses of naïve hMSC to these DMs were determined by qPCR and DNA quantification and compared to that of hMSCs cultured on TCP alone following 7 days in OM. Each response model was found to be significant (p<0.05) and the linear, quadratic, and two-factor interactions of each variable were assessed (Table 2).

Figure 7:
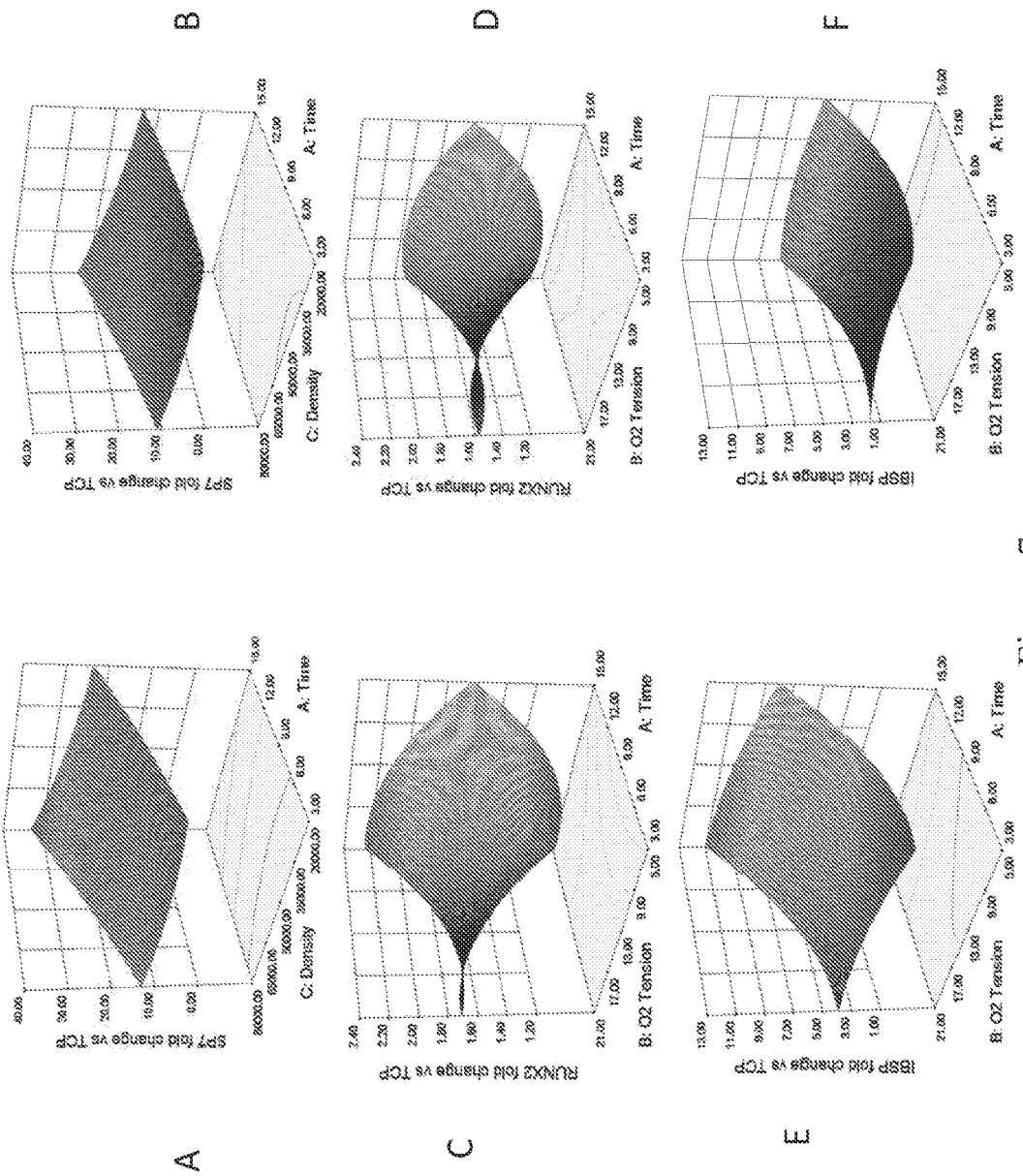
FIG. 7. DMs engineered using extended culture duration, higher seeding densities, ambient oxygen tension and A2P supplemented media appeared most effective at driving naïve hMSC osteogenesis, as determined by 3D surface model graphs exhibiting the correlation between culture conditions during matrix deposition and the resulting response of naïve hMSCs. (A) SP7 (osterix) expression in SM (21% $O_2$), (B) SP7 expression in OM (21% $O_2$), (C) RUNX2 expression in SM, (D) RUNX2 expression in OM, (E) IBSP expression in SM, and (F) IBSP expression in OM at 7 days. Data are fold change over expression in hMSCs on tissue culture plastic (TCP).

DOE predictions of the naïve hMSC response to DMs engineered using different culture conditions were generated based on experimental results (FIG. 7). mRNA expression of osterix (SP7), a zinc finger-containing transcription factor required for osteoblast differentiation and bone formation[35], increased 8- to 35-fold in naïve hMSCs cultured on DMs after 7 days compared with cells cultured on TCP alone (FIGS. 7A, B). SP7 expression was significantly higher on DMs with extended culture durations and deposited in SM (FIG. 7A) rather than OM (FIG. 7B). mRNA expression of RUNX2, another key transcription factor associated with osteoblast differentiation[31], underwent a more modest 1- to 2-fold increase on DMs over TCP (FIG. 7C,D). RUNX2 expression was modulated in both a linear and quadratic fashion by the culture duration and oxygen tension under which DMs were deposited, with extended culture duration and higher oxygen tension each yielding increased RUNX2 expression by hMSCs. Expression of bone sialoprotein (IBSP) mRNA, generating a protein component of native bone ECM that enhances matrix mineralization[18], increased 2- to 10-fold in naïve hMSCs cultured on DMs compared with TCP, with increases in IBSP correlating with increased DM culture duration (FIG. 7E,F). Similar to SP7, IBSP was also present at significantly higher levels in naïve hMSCs cultured on DMs deposited in SM (FIG. 7E) compared with those deposited in OM (FIG. 7F). Finally, hMSC proliferation increased significantly when cultured on DMs deposited over extended time periods and in OM (data not shown). Culture conditions not specifically noted in FIGS. 7A-H are constant at their median value.

Results from the DOE-based experiments indicated that hMSC-secreted matrices deposited over longer durations (15 days) with higher initial seeding densities (8e4 cells/cm$^2$) under higher oxygen tensions (21% $O_2$) and in SM produce the most effective osteogenic substrates after decellularization. As verification of each of these findings would prove cumbersome and to further explore the efficacy of this model, we performed in-depth analyses of two distinct DMs predicted to be most effective (DM1) and somewhat less effective (DM2) at instructing the osteogenic differentiation of naïve hMSCs. DM1 was deposited over 15 days in 21% $O_2$, while DM2 was deposited over 6 days in 5% $O_2$. Both DM1 and DM2 were produced using initial seeding densities of 8e4 cells/$cm^2$ and cultured in SM.

Characterization of Decellularized Matrices (DMs)

Figure 8:
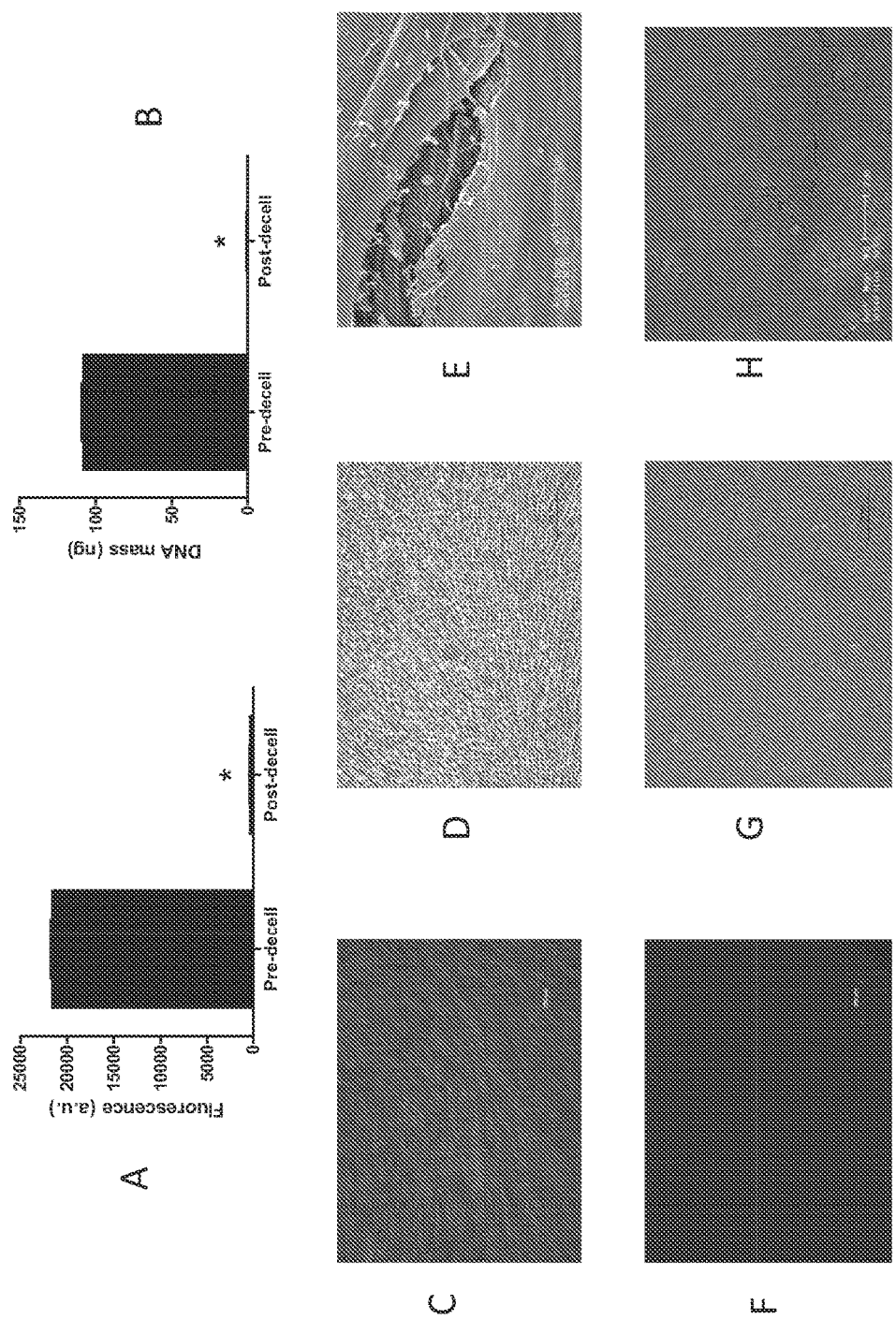
FIG. 8. Quantitative analysis of the decellularization of DM1 utilizing (A) calcein uptake (n=3) and (B) DNA quantification (n=6). Fluorescent microscopy images of calcein uptake pre-(C) and post-decellularization (F). Bright field images (100× magnification) of cell layers pre-(D) and post-decellularization (G). SEM images of cell layers pre-(E) and post-decellularization (H) at 8172× magnification. Scale bars represent 250 μm (C,D,F,G) and 2 μm (E,H). *p<0.0001 vs. pre-decell layers (A,B).

Decellularization of confluent hMSC layers (DM1) was confirmed by quantification of residual calcein uptake and DNA present within 12-well plates upon application of our decellularization protocol. Calcein uptake was virtually eliminated upon decellularization (FIG. 8A), with a 98.6% reduction in fluorescence observed in decellularized wells. Fluorescent microscopy images of calcein-treated wells before (FIG. 8C) and after decellularization (FIG. 8F) confirmed an apparent reduction in viable cells. Quantification of soluble DNA present within DM1-coated wells treated with cell lysis buffer also revealed a 99.9% reduction upon decellularization (FIG. 8B). Bright field and scanning electron microscopy were used to image DM1 hMSC cell layers before (FIG. 8D,E) and after decellularization (FIG. 8G,H), respectively. These techniques revealed a visible residual substrate composed in part of both proteins and glycosaminoglycans, as determined by staining with coomassie brilliant blue and Alcian blue (data not shown).

qPCR

Figure 9:
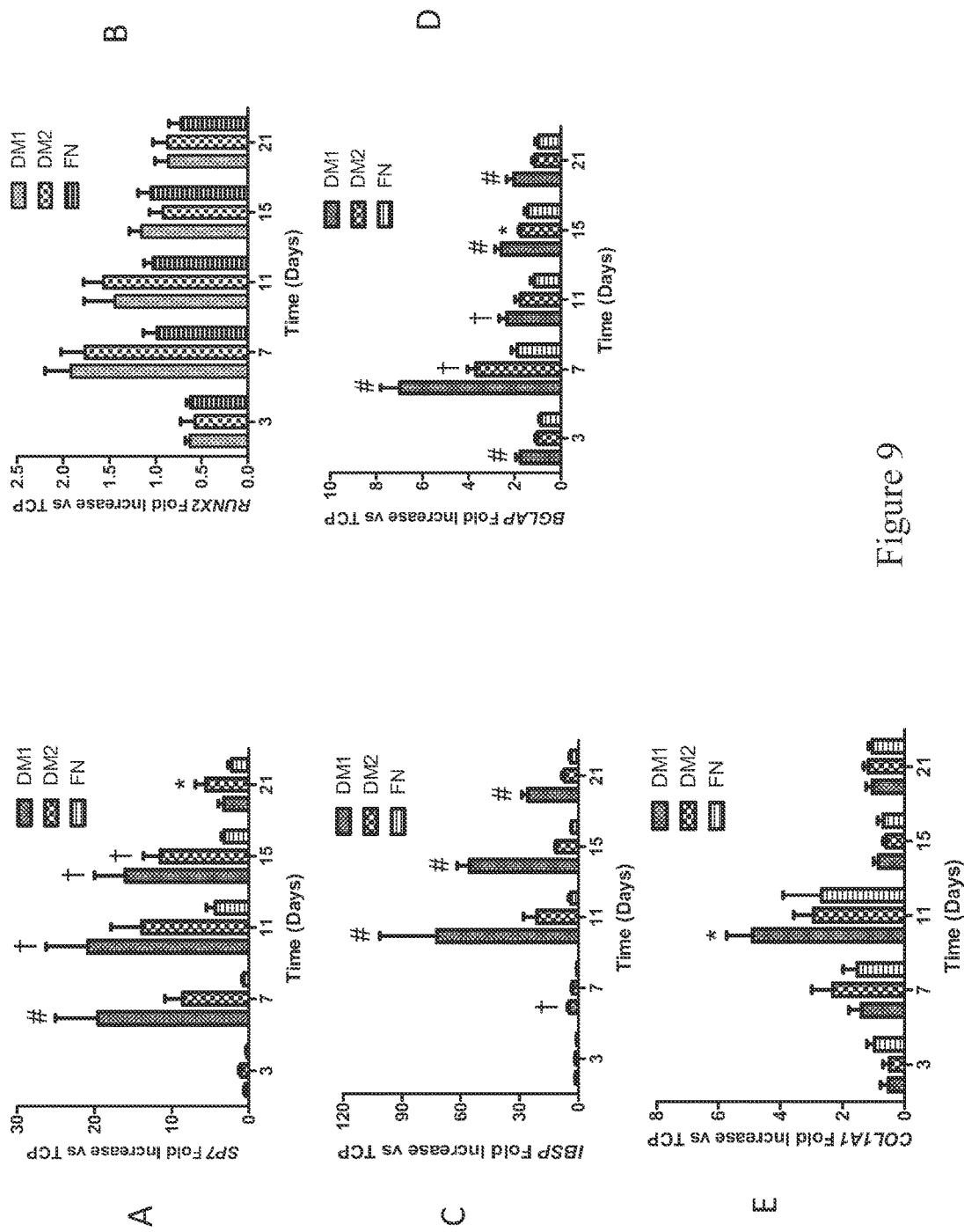
FIG. 9. DM1 enhanced expression of several ostegenic marker genes in hMSCs compared to DM2 or control substrates when probed by qPCR in hMSCs cultured on each substrate for 3 to 21 days: (A) SP7, (B) IBSP, (C) RUNX2, (D) BGLAP (osteocalcin), and (E) COL1A1. Data were normalized to MRPL13 transcript level and reported as fold change in mRNA expression vs. TCP controls. #p<0.05 vs. all groups, †p<0.05 vs. FN and TCP, *p<0.05 vs. TCP only (n=3).

We analyzed gene expression of five markers related to osteogenic differentiation (osterix, Runx2), as well as bone mineralization and ECM deposition (bone sialoprotein, osteocalcin, collagen 1a) over 21 days in hMSCs cultured on DM1, DM2, fibronectin, and TCP. Osterix expression from hMSCs cultured on DM1 was significantly higher than all other groups at 7 days, with a roughly 20-fold increase over hMSCs cultured on TCP, and a 2-fold increase over hMSCs cultured on DM2 (FIG. 9A). Both DM1 and DM2 were effective at stimulating osterix expression over the control surfaces at days 7, 11, and 15. Similar to prior DOE experimental results obtained during initial application, increases in RUNX2 expression resulting from hMSC culture on DM1 and DM2 were more muted. A roughly 2-fold increase was observed for cells on DM1 and DM2 over control groups at 7 days, with RUNX2 expression returning to those present in hMSCs cultured on TCP by 15 days (FIG. 9B).

Bone sialoprotein (IBSP) mRNA expression in hMSCs cultured on DM1 was significantly higher than all other groups from day 11 through 21, peaking with a roughly 75-fold increase over TCP controls at 11 days (FIG. 9C). hMSCs cultured on DM2 also showed a trend for increased IBSP expression over control groups from day 7 through 21. mRNA expression of osteocalcin (BGLAP), a common biochemical marker of bone formation[27], exhibited a significant increase in hMSCs cultured on DM1-coated wells over all other groups at days 3, 7, 15, and 21 (FIG. 9D). This expression peaked with a roughly 7-fold increase over TCP and 2-fold increase over DM2 at 7 days. Finally, collagen 1a expression, an essential building block of the major organic component of native bone ECM, was significantly increased in hMSCs cultured on DM1 compared with all other groups at 11 days (FIG. 9E).

Alkaline Phosphatase Activity and Calcium Deposition

Figure 10:
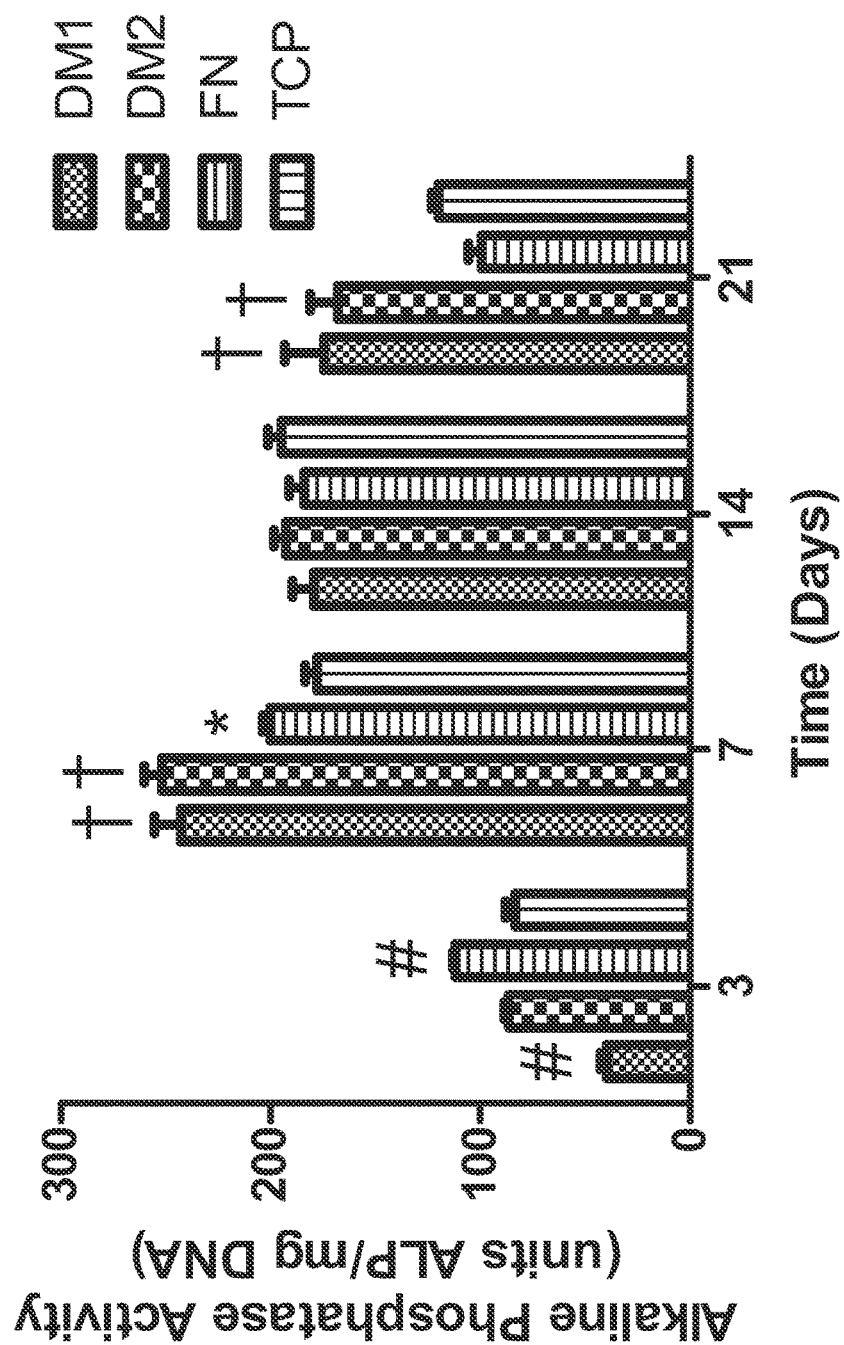
FIG. 10. Alkaline phosphatase activity from hMSCs cultured on each substrate for up to 21 days. #p<0.05 vs. all groups, †p<0.05 vs. FN and TCP, *p<0.05 vs. TCP only (n=4-6).

Quantification of intracellular ALP activity in hMSCs cultured on DM1, DM2, fibronectin and TCP in OM over 21 days revealed a significant increase within cells cultured on DM1 and DM2 at days 7 and 21 compared to controls (FIG. 10). No discernable differences in ALP levels were detectable between cells cultured on DM1 and DM2 coated plates with the exception of a reduction in ALP on DM1 coated plates on day 3.

Figure 11:
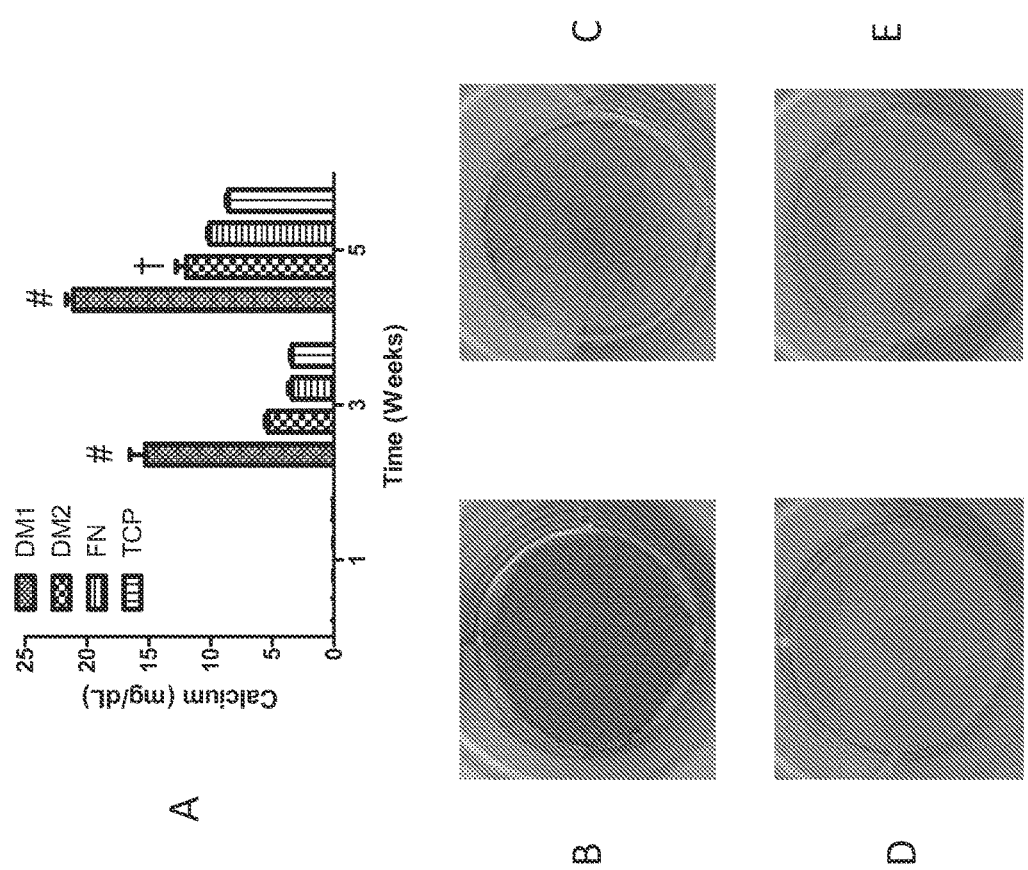
FIG. 11. hMSCs cultured on DM1 exhibited increased calcium deposition compared to cells on DM2 or control substrates. (A) Calcium deposited from hMSCs cultured on each substrate for 1, 3, and 5 weeks. Alizarin red staining of fixed hMSC layers cultured for 3 weeks on (B) DM1, (C) DM2, (D) FN, and (E) TCP. #p<0.05 vs. all groups, †p<0.05 vs. FN and TCP (n=3-4).

Calcium deposition from hMSCs cultured on each substrate in OM was assayed both quantitatively and qualitatively over five weeks. Quantitative analysis revealed a significant increase in calcium deposition from hMSCs cultured on DM1 over all other groups at weeks 3 and 5, with a roughly 4-fold increase over control groups at week 3 (FIG. 11A). hMSCs cultured on DM2 also showed a significant increase in calcium deposition at week 5. No appreciable calcium deposition was noted after one week of hMSC culture, nor was any detectable calcium present in DM1 or DM2 prior to hMSC seeding. Qualitative analysis of wells via alizarin red staining also revealed a significant increase in calcium deposition by hMSCs cultured on DN1 (FIG. 11B) over all other groups (FIG. 11C-E) by 3 weeks.

Cell Proliferation, Viability, and Attachment

Figure 12:
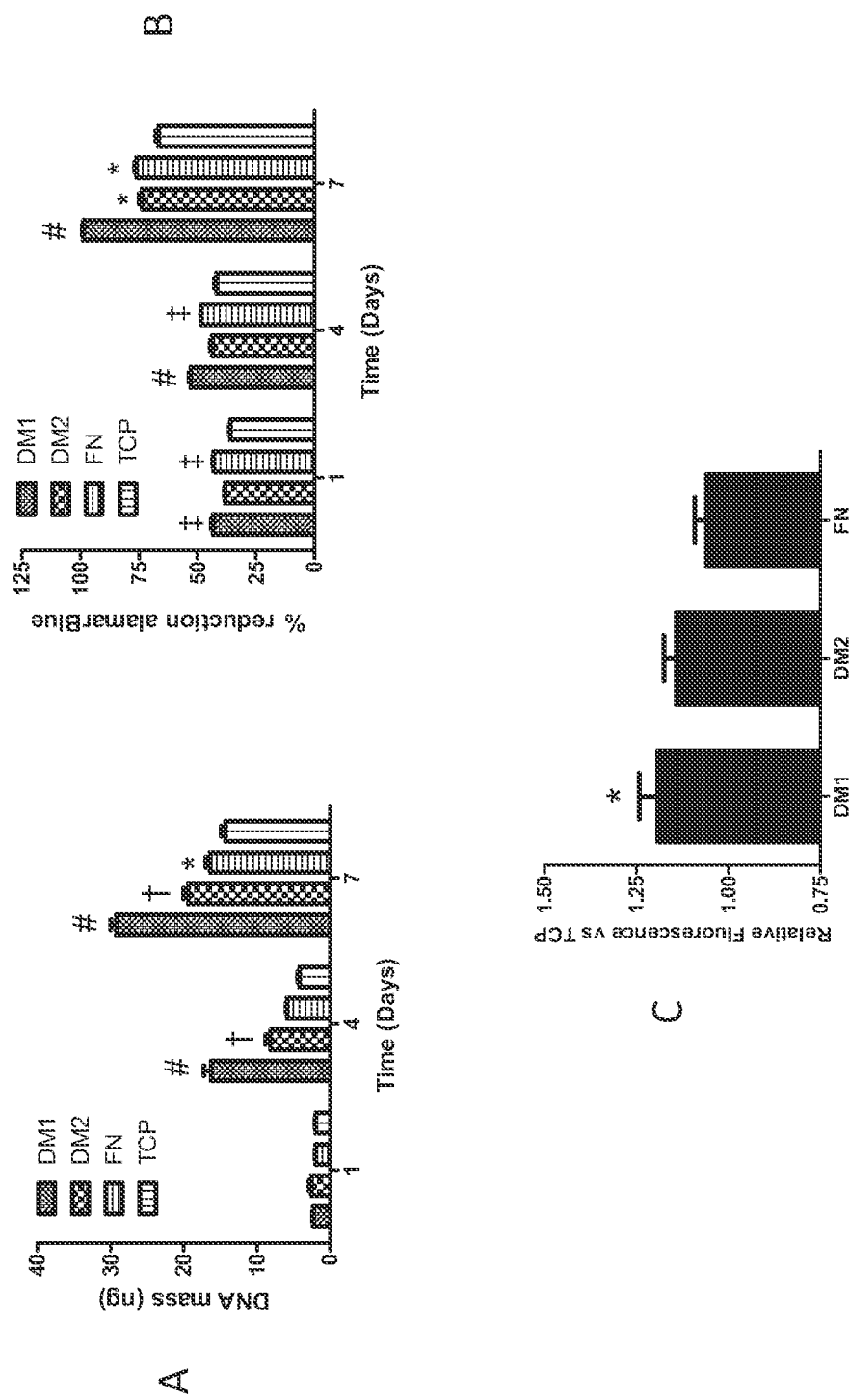
FIG. 12. hMSC proliferation and viability are enhanced when cultured on DM1 compared to culture on DM2 or control substrates. (A) Total DNA on each substrate at 1, 4, and 7 days post-seeding. (B) AlamarBlue reduction by hMSCs cultured on each substrate at 1, 4, and 7 days. (C) Calcein uptake by hMSCs seeded on each substrate and under environmental stress for 24 h. #p<0.05 vs. all groups, ‡p<0.05 vs. DM2 and TCP, †p<0.05 vs. FN and TCP, *p<0.05 vs. TCP only (n=4-6).

We detected a significant increase in the proliferative potential of hMSCs cultured on DM1 over all other groups at days 4 and 7 (FIG. 12A). hMSCs cultured on DM2-coated wells also proliferated faster than cells cultured on control surfaces. Furthermore, we observed differences in cell viability and metabolism of hMSCs cultured on the four surfaces. We detected a significant increase in alamarBlue reduction, an indicator of cell metabolism, from hMSCs cultured on DM1-coated wells over cells cultured on DM2-coated wells and TCP at all timepoints (FIG. 12B). hMSCs cultured on DM2-coated wells also showed a slight but significant increase in alamarBlue reduction at days 1 and 7 in comparison to hMSCs cultured on TCP alone. The ability of each of the four substrates to influence cell viability under harsh environmental conditions, such as those faced upon implantation in vivo, was also examined by total calcein uptake within wells following 24 hours in a serum free and hypoxic environment. We observed significantly greater calcein uptake by hMSCs cultured on DM1-coated wells compared to cells cultured in control TCP wells (FIG. 12C).

Figure 13:
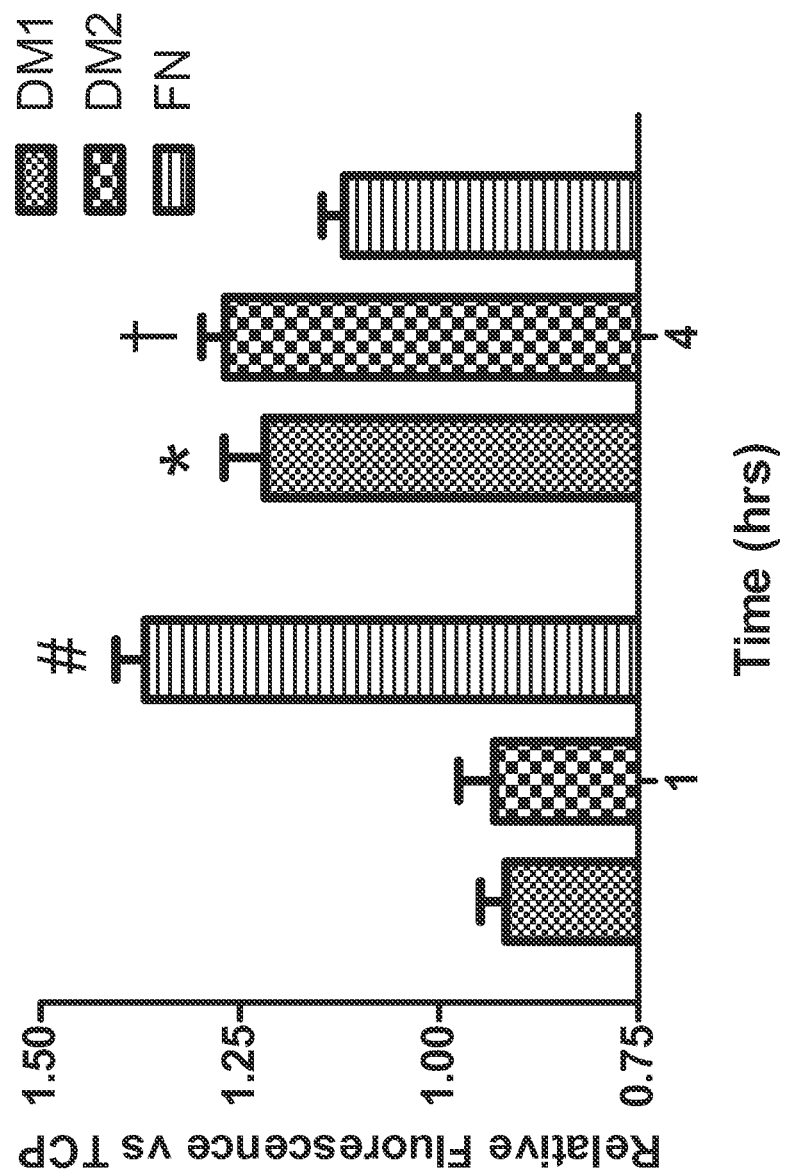
FIG. 13. Calcein uptake by hMSCs seeded on each substrate at 1 and 4 hours post-seeding. #p<0.05 vs. all groups, †p<0.05 vs. FN and TCP, *p<0.05 vs. TCP only (n=4).

The capacity of hMSCs to attach to DM1, DM2, fibronectin, and TCP substrates was assayed by calcein uptake within the wells at 1 and 4 hours post-seeding. After 1 hour, only fibronectin-coated wells exhibited a significant increase in calcein uptake. However, we detected significant increases in calcein uptake 4 hours post-seeding for cells on both DM1- and DM2-coated wells compared with TCP wells, and calcein uptake in DM2-coated wells was increased over fibronectin-coated wells (FIG. 13).

CONCLUSIONS

We employed a Design of Experiments (DOE) multivariable analysis approach to determine the effects and interactions of four variables (culture duration, cell seeding density, oxygen tension, and media supplementation) on the capacity of DMs to direct the osteogenic differentiation of human mesenchymal stem cells (hMSCs). DOE analysis revealed that matrices created with extended culture duration, ascorbate-2-phosphate supplementation, and in ambient oxygen tension exhibited significant correlations with enhanced hMSC differentiation. We validated the DOE model results using DMs predicted to have superior (DM1) or lesser (DM2) osteogenic potential for naïve hMSCs. Compared to cells on DM2, hMSCs cultured on DM1 expressed 2-fold higher osterix levels and deposited 3-fold more calcium over 3 weeks. Cells on DM1 coatings also exhibited greater proliferation and viability compared to DM2-coated substrates. This study demonstrates that DOE-based analysis is a powerful tool for optimizing engineered systems by identifying significant variables that have the greatest contribution to the target output.

REFERENCES FOR EXAMPLE 3

1. Aulin, C., F. Foroughi, R. Brown, and J. Hilborn. Extracellular matrix-polymer hybrid materials produced in a pulsed-flow bioreactor system. J Tissue Eng Regen Med. 3:188-195, 2009.
2. Badylak, S. F., D. O. Freytes, and T. W. Gilbert. Extracellular matrix as a biological scaffold material: Structure and function. Acta biomaterialia. 5:1-13, 2009.
3. Badylak, S. F., and T. W. Gilbert. Immune response to biologic scaffold materials. Semin Immunol. 20:109-116, 2008.
4. Bancroft, G. N., V. I. Sikavitsas, J. van den Dolder, T. L. Sheffield, C. G. Ambrose, J. A. Jansen, and A. G. Mikos. Fluid flow increases mineralized matrix deposition in 3D perfusion culture of marrow stromal osteoblasts in a dose-dependent manner. Proc Natl Acad Sci USA. 99:12600-12605, 2002.
5. Bennett, K. P., C. Bergeron, E. Acar, R. F. Klees, S. L. Vandenberg, B. Yener, and G. E. Plopper. Proteomics reveals multiple routes to the osteogenic phenotype in mesenchymal stem cells. BMC Genomics. 8:380, 2007.
6. Caplan, A. I., and J. E. Dennis. Mesenchymal stem cells as trophic mediators. Journal of cellular biochemistry. 98:1076-1084, 2006.
7. Chen, W. L., M. Likhitpanichkul, A. Ho, and C. A. Simmons. Integration of statistical modeling and high-content microscopy to systematically investigate cell-substrate interactions. Biomaterials. 31:2489-2497.
8. Chen, X. D. Extracellular matrix provides an optimal niche for the maintenance and propagation of mesenchymal stem cells. Birth Defects Res C Embryo Today. 90:45-54.
9. Chen, X. D., V. Dusevich, J. Q. Feng, S. C. Manolagas, and R. L. Jilka. Extracellular matrix made by bone marrow cells facilitates expansion of marrow-derived mesenchymal progenitor cells and prevents their differentiation into osteoblasts. J Bone Miner Res. 22:1943-1956, 2007.
10. Choi, K. M., Y. K. Seo, H. H. Yoon, K. Y. Song, S. Y. Kwon, H. S. Lee, and J. K. Park. Effect of ascorbic acid on bone marrow-derived mesenchymal stem cell proliferation and differentiation. Journal of bioscience and bioengineering. 105:586-594, 2008.
11. Cool, S. M., and V. Nurcombe. Substrate induction of osteogenesis from marrow-derived mesenchymal precursors. Stem Cells Dev. 14:632-642, 2005.
12. Dahl, S. L., J. Koh, V. Prabhakar, and L. E. Niklason. Decellularized native and engineered arterial scaffolds for transplantation. Cell transplantation. 12:659-666, 2003.
13. Datta, N., H. L. Holtorf, V. I. Sikavitsas, J. A. Jansen, and A. G. Mikos. Effect of bone extracellular matrix synthesized in vitro on the osteoblastic differentiation of marrow stromal cells. Biomaterials. 26:971-977, 2005.
14. Datta, N., Q. P. Pham, U. Sharma, V. I. Sikavitsas, J. A. Jansen, and A. G. Mikos. In vitro generated extracellular matrix and fluid shear stress synergistically enhance 3D osteoblastic differentiation. Proc Natl Acad Sci USA. 103:2488-2493, 2006.
15. Davis, H. E., R. R. Rao, J. He, and J. K. Leach. Biomimetic scaffolds fabricated from apatite-coated polymer microspheres. Journal of biomedical materials research. 90:1021-1031, 2009.
16. Decaris, M. L., C. I. Lee, M. C. Yoder, A. F. Tarantal, and J. K. Leach. Influence of the oxygen microenvironment on the proangiogenic potential of human endothelial colony forming cells. Angiogenesis. 2009.
17. Dennis, J. E., S. E. Haynesworth, R. G. Young, and A. I. Caplan. Osteogenesis in marrow-derived mesenchymal cell porous ceramic composites transplanted subcutaneously: effect of fibronectin and laminin on cell retention and rate of osteogenic expression. Cell transplantation. 1:23-32, 1992.
18. Gordon, J. A., C. E. Tye, A. V. Sampaio, T. M. Underhill, G. K. Hunter, and H. A. Goldberg. Bone sialoprotein expression enhances osteoblast differentiation and matrix mineralization in vitro. Bone. 41:462-473, 2007.
19. Grayson, W. L., S. Bhumiratana, C. Cannizzaro, P. H. Chao, D. P. Lennon, A. I. Caplan, and G. Vunjak-Novakovic. Effects of initial seeding density and fluid perfusion rate on formation of tissue-engineered bone. Tissue engineering. 14:1809-1820, 2008.
20. Grayson, W. L., F. Zhao, B. Bunnell, and T. Ma. Hypoxia enhances proliferation and tissue formation of human mesenchymal stem cells. Biochem Biophys Res Commun. 358:948-953, 2007.
21. Griffiths, L. G., L. H. Choe, K. F. Reardon, S. W. Dow, and E. Christopher Orton. Immunoproteomic identification of bovine pericardium xenoantigens. Biomaterials. 29:3514-3520, 2008.
22. Grunert, M., C. Dombrowski, M. Sadasivam, K. Manton, S. M. Cool, and V. Nurcombe. Isolation of a native osteoblast matrix with a specific affinity for BMP2. J Mol. Histol. 38:393-404, 2007.
23. Guilak, F., D. M. Cohen, B. T. Estes, J. M. Gimble, W. Liedtke, and C. S. Chen. Control of stem cell fate by physical interactions with the extracellular matrix. Cell stem cell. 5:17-26, 2009.
24. He, J., D. C. Genetos, C. E. Yellowley, and J. K. Leach. Oxygen tension differentially influences osteogenic differentiation of human adipose stem cells in 2D and 3D cultures. Journal of cellular biochemistry. 110:87-96.
25. Hidalgo-Bastida, L. A., and S. H. Cartmell. Mesenchymal stem cells, osteoblasts and extracellular matrix proteins: enhancing cell adhesion and differentiation for bone tissue engineering. Tissue Eng Part B Rev. 16:405-412.
26. Hoshiba, T., N. Kawazoe, T. Tateishi, and G. Chen. Development of stepwise osteogenesis-mimicking matrices for the regulation of mesenchymal stem cell functions. The Journal of biological chemistry. 284:31164-31173, 2009.
27. Jaiswal, N., S. E. Haynesworth, A. I. Caplan, and S. P. Bruder. Osteogenic differentiation of purified, culture-expanded human mesenchymal stem cells in vitro. Journal of cellular biochemistry. 64:295-312, 1997.
28. Kim, S. H., and G. M. Lee. Development of serum-free medium supplemented with hydrolysates for the production of therapeutic antibodies in CHO cell cultures using design of experiments. Applied microbiology and biotechnology. 83:639-648, 2009.
29. Kundu, A. K., and A. J. Putnam. Vitronectin and collagen I differentially regulate osteogenesis in mesenchymal stem cells. Biochem Biophys Res Commun. 347:347-357, 2006.
30. Lecanda, F., L. V. Avioli, and S. L. Cheng. Regulation of bone matrix protein expression and induction of differentiation of human osteoblasts and human bone marrow stromal cells by bone morphogenetic protein-2. Journal of cellular biochemistry. 67:386-396, 1997.
31. Lian, J. B., A. Javed, S. K. Zaidi, C. Lengner, M. Montecino, A. J. van Wijnen, J. L. Stein, and G. S. Stein. Regulatory controls for osteoblast growth and differentiation: role of Runx/Cbfa/AML factors. Critical reviews in eukaryotic gene expression. 14:1-41, 2004.
32. Liao, J., X. Guo, D. Nelson, F. K. Kasper, and A. G. Mikos. Modulation of osteogenic properties of biodegradable polymer/extracellular matrix scaffolds generated with a flow perfusion bioreactor. Acta biomaterialia. 6:2386-2393.
33. Mauney, J. R., D. L. Kaplan, and V. Volloch. Matrix-mediated retention of osteogenic differentiation potential by human adult bone marrow stromal cells during ex vivo expansion. Biomaterials. 25:3233-3243, 2004.
34. Mauney, J. R., C. Kirker-Head, L. Abrahamson, G. Gronowicz, V. Volloch, and D. L. Kaplan. Matrix-mediated retention of in vitro osteogenic differentiation potential and in vivo bone-forming capacity by human adult bone marrow-derived mesenchymal stem cells during ex vivo expansion. Journal of biomedical materials research. 79:464-475, 2006.
35. Nakashima, K., X. Zhou, G. Kunkel, Z. Zhang, J. M. Deng, R. R. Behringer, and B. de Crombrugghe. The novel zinc finger-containing transcription factor osterix is required for osteoblast differentiation and bone formation. Cell. 108:17-29, 2002.
36. Ogura, N., M. Kawada, W. J. Chang, Q. Zhang, S. Y. Lee, T. Kondoh, and Y. Abiko. Differentiation of the human mesenchymal stem cells derived from bone marrow and enhancement of cell attachment by fibronectin. Journal of oral science. 46:207-213, 2004.
37. Petrie, T. A., J. E. Raynor, D. W. Dumbauld, T. T. Lee, S. Jagtap, K. L. Templeman, D. M. Collard, and A. J. Garcia. Multivalent integrin-specific ligands enhance tissue healing and biomaterial integration. Science translational medicine. 2:45ra60.
38. Pham, Q. P., F. K. Kasper, L. Scott Baggett, R. M. Raphael, J. A. Jansen, and A. G. Mikos. The influence of an in vitro generated bone-like extracellular matrix on osteoblastic gene expression of marrow stromal cells. Biomaterials. 29:2729-2739, 2008.
39. Rao, R. R., J. He, and J. K. Leach. Biomineralized composite substrates increase gene expression with nonviral delivery. Journal of biomedical materials research. 94:344-354.
40. Shah, M., and K. Pathak. Development and statistical optimization of solid lipid nanoparticles of simvastatin by using 2(3) full-factorial design. AAPS PharmSciTech. 11:489-496.
41. Singelyn, J. M., J. A. DeQuach, S. B. Seif-Naraghi, R. B. Littlefield, P. J. Schup-Magoffin, and K. L. Christman. Naturally derived myocardial matrix as an injectable scaffold for cardiac tissue engineering. Biomaterials. 30:5409-5416, 2009.
42. Zahed, M. A., H. A. Aziz, M. H. Is a, L. Mohajeri, and S. Mohajeri. Optimal conditions for bioremediation of oily seawater. Bioresource technology.
43. Zhang, Y., Y. He, S. Bharadwaj, N. Hammam, K. Carnagey, R. Myers, A. Atala, and M. Van Dyke. Tissue-specific extracellular matrix coatings for the promotion of cell proliferation and maintenance of cell phenotype. Biomaterials. 30:4021-4028, 2009.

Example 4

Transferable Cell-Secreted Extracellular Matrices Enhance Osteogenic Differentiation Materials and Methods Cell Culture Human bone marrow-derived MSCs (hMSCs, Lonza, Walkersville, Md.) were expanded without further characterization in minimum essential alpha medium (α-MEM w/L-glutamine, w/o ribo/deoxyribonucleosides; Cat. #12000-022, Invitrogen, Carlsbad, Calif.) supplemented with 10% fetal bovine serum (FBS, JR Scientific, Woodland, Calif.) and 1% penicillin and streptomycin (P/S, Mediatech, Manassas, Va.). Cells were cultured under standard conditions and utilized at passages 4-6. Medium was further supplemented with 50 µg/mL ascorbate-2-phosphate (A2P) for one passage prior to experimental use to prime cells for enhanced matrix deposition.[18]

Preparation of Decellularized Matrices (DMs)

hMSCs were seeded on 6 or 12-well plates at 50,000 cells/cm$^2$ and cultured in supplemented media (SM: α-MEM, 10% FBS, 1% P/S, 50 µg/mL A2P) for 15 d under standard culture conditions with media changes performed every 3 d. Wells were decellularized as previously described.[10] Briefly, wells were rinsed with PBS and treated with 0.5% Triton X-100 (Sigma, St. Louis, Mo.) in 20 mM NH$_4$OH in PBS for 5 min at 37° C. Wells were rinsed with PBS and treated with DNAse (Sigma, 150 units/mL PBS) for 1 h at 37° C., and rinsed in PBS again. Plates were allowed to dry within a sterile biosafety cabinet for up to 12 h. DM-coated plates were stored at room temperature in the dark for up to 1 month prior to use. DM-coated plates were rinsed twice with PBS before further examination or seeding.

Transferring Decellularized Matrices 6-well DM-coated plates were scraped in the presence of 0.02 N acetic acid (50 µl), transferred to microcentrifuge tubes, and sonicated (Sonics & Materials Vibra-Cell VCX130PB) on ice with 2 s pulses 10-15 times to mechanically homogenize DM contents. After sonication, the mixture appeared cloudy with very small chunks of DM content dispersed in solution. DM contents from sufficient culture areas were then pipetted into standard TCP plates at concentrations similar to that of original DMs (1×) as determined by Amido black protein quantification [19], or diluted with 0.02 N acetic acid to 40% (0.4×) or 10% (0.1×) to analyze the dose dependent response of naïve hMSCs to tDM concentration. tDM-coated plates were dried in a sterile biosafety cabinet for up to 12 h and stored at room temperature in the dark for up to 1 month prior to use. tDM-coated plates were rinsed twice with PBS before further examination or seeding.

Characterization of Matrix Composition

To determine the effect of decellularization and transfer of DMs on composition, immunocytochemistry was performed on DM-coated surfaces using a mouse specific HRP/DAB detection IHC kit (Abcam) in conjunction with primary antibodies (Santa Cruz) for type 1 collagen (sc-80769, 1:50), fibronectin (sc-71114, 1:50), biglycan (sc-100857, 1:50), decorin (sc-73896, 1:50), and α-tubulin (sc-32293, 1:50) incubated overnight at 4° C. Total protein content was visualized by incubation in 0.2% Coomassie brilliant blue dissolved in 20% methanol, 0.05% acetic acid, and 79.5% water (MP, Solon, Ohio) for 15 min. To analyze hMSC layers prior to decellularization, samples were fixed in 2% formaldehyde for 15 min then stored at 4° C. in PBS prior to staining Quantification of Osteogenic Potential: qPCR, Alkaline Phosphatase, and Calcium hMSCs (Lonza) were seeded on DM-coated, tDM-coated, or uncoated TCP wells in SM at 7,500 cells/cm$^2$ and allowed to attach overnight. Culture medium was refreshed with osteogenic media (OM: α-MEM, 10% FBS, 1% P/S+10 mM β-glycerophosphate, 50 μg/mL A2P, 10 nM dexamethasone) the following day, and cells were cultured in standard conditions for up to 14 d. Total RNA was collected using the RNeasy Mini kit (Qiagen, Valencia, Calif.) and 400 ng of total RNA was then reverse-transcribed with the QuantiTect Reverse Transcription Kit (Qiagen). qPCR was performed using TaqMan1 Universal PCR Master Mix (Applied Biosystems, Foster City, Calif.) on a Mastercycler1 realplex2 (Eppendorf, Westbury, N.Y.); primers and probes for BGLAP (Hs01587814_g1), IBSP (Hs00173720_m1), MRPL13 (Hs00204173_m1), RUNX2 (Hs00231692_m1), and SP7 (Hs01866874_s1) were purchased from Applied Biosystems. Amplification conditions were 50° C. for 2 min, 95° C. for 10 min, followed by 40 cycles at 95° C. for 15 s and 60° C. for 1 min. Quantitative PCR results were normalized to RPL13 transcript level to yield ΔCt. Fold change in expression was then calculated using the formula $2^{\Delta Ct}$ and fold changes between experimental groups and control wells calculated to yield ΔΔCt.[20]

Intracellular alkaline phosphatase (ALP) activity was quantified from hMSCs seeded on DM-coated, tDM-coated, and uncoated TCP wells at 4,000 cells/cm$^2$ using a PNPP colorimetric assay at 405 nm as described.[21] ALP activity was normalized to sample DNA content determined using the Quant-iT PicoGreen dsDNA kit (Invitrogen). The distribution of mineralized deposits resulting from hMSC culture on DMs, tDMs and TCP was analyzed for up to 4 weeks both qualitatively using Alizarin Red staining and quantitatively with an OCOP colorimetric assay as described.[21, 22]

pERK Expression hMSCs were seeded on DM-coated, tDM-coated, and uncoated TCP at 7,500 cells/cm$^2$ as described above. Cell lysates were collected following PBS rinse with 4× sample buffer (20% glycerol, 4% SDS, 0.05% bromophenol blue, 160 mM Tris-HCl, and 200 mM DTT). Protein concentration was determined using the Amido Black method. 10 μg of protein per sample was resolved in 4-12% Tris-HCl acrylamide gels (Invitrogen) and transferred onto 0.2 mm nitrocellulose. Blots were blocked in 5% nonfat milk in Tris-buffered saline with 0.05% Tween-20 (TBST) for 1 h and probed with primary antibodies for Erk1 (Santa Cruz, sc-94, 1:500) and phospho-p44/42 MAPK (ERK1/2) (Cell Signaling, 4377s, 1:500) overnight at 4° C. Membranes were washed, probed with horseradish peroxidase-conjugated secondary antibodies at 1:1000 (Cell Signaling) and reactive bands were visualized using enhanced chemiluminescence and X-ray film.

Integrin Mediated Cell Attachment hMSCs were serum-starved (0.5% FBS) overnight and pre-treated for 30 min with antibodies (10 μg/mL) specific to integrin $\alpha_v\beta_3$ (Abcam, ab78289)[23], integrin $\alpha_2\beta_1$ (Santa Cruz, sc-59955), integrin $\alpha_5\beta_1$ (Millipore, MAB1969)[24] or a non-specific isotype control antibody (Abcam, ab81032). Cells were then seeded at 30,000 cells/cm$^2$ on tDM-coated or uncoated 24-well TCP plates in FBS-containing osteogenic media. After 45 min, wells were rinsed vigorously with PBS and the remaining adherent cells quantified by uptake of calcein AM. Cells were incubated in 3 μg/mL calcein AM (Invitrogen) in media, followed by media exchange and quantification of fluorescence using a plate reader (Synergy HTTR, Biotek, Wisnooski, Vt.).

Statistical Analysis

Data are presented as mean±standard deviation unless otherwise stated. Statistical analysis was performed using paired Student's t-tests and one-way ANOVA followed by Student Newman-Keuls posthoc test where applicable. P values less than 0.05 were considered statistically significant.

Results

Characterization of Transferred Decellularized Matrices (tDMs)

Figure 14:
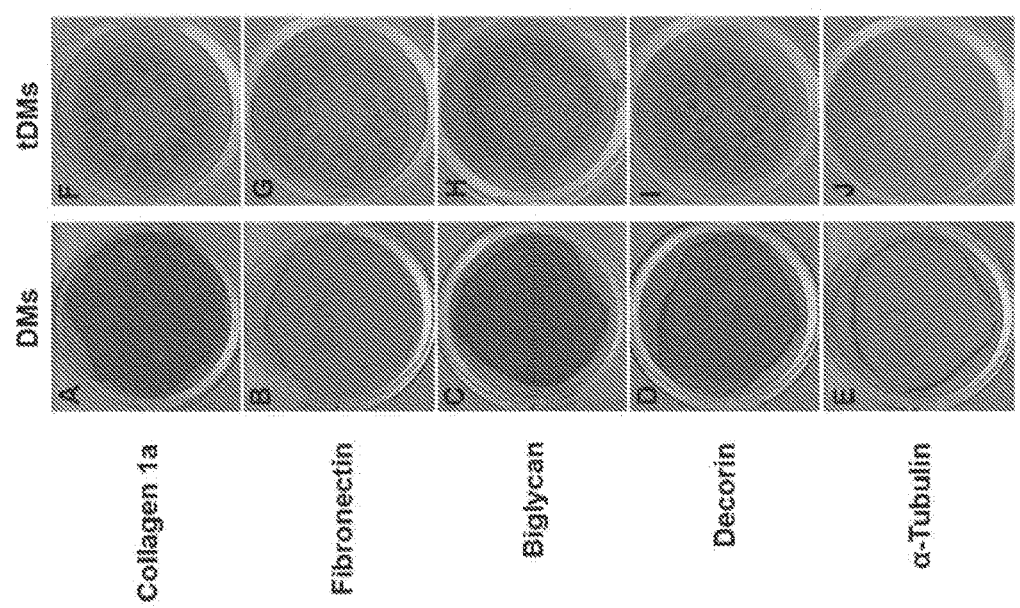
FIG. 14. Characterization of DM composition using immunocytochemistry before (A-E) and after (F-J) transfer. (A, F) Type 1 collagen, (B, G) fibronectin, (C, H) biglycan, (D, I) decorin, and (E, J) α-tubulin.

After quantification of protein content within DMs (15.2±3.0 μg/cm$^2$, n=3), 1×tDMs were created by coating TCP with 16.8±2.4 μg protein/cm$^2$ of surface area. 0.4× and 0.1× layers were generated by diluting the total protein from 1× layers in acetic acid accordingly. Many components of the ECM secreted by hMSCs in culture play vital roles in bone cell regulation. Type 1 collagen plays a major structural role in bone tissue, while fibronectin is critical in bone cell adhesion [25], and both proteins were evident before and after transfer following immunocytochemistry (FIG. 14A, B, F, G). Biglycan and decorin, proteoglycans known to play pivotal roles in growth factor signaling, osteoblast differentiation, and matrix mineralization [26, 27], were present and retained within DMs following transfer (FIG. 14C, D, H, I). As a control, DMs were also stained for the presence of α-tubulin, a marker of intracellular proteins that should be removed by the decellularization process. While α-tubulin was present in great abundance prior to decellularization (data not shown), both DMs and tDMs exhibited greatly reduced amounts (FIG. 14E, J). This is in good agreement with our previous report of decellularization efficiency using identical decellularization protocols and quantification of calcein uptake and residual DNA content. [10] Differences in staining intensity following DM transfer are due to the transfer process itself, as the homogeneous DM layer is broken down but not fully solubilized prior to transfer to maximize the preservation of ECM activity.

Quantification of Osteogenic Potential

Figure 15:
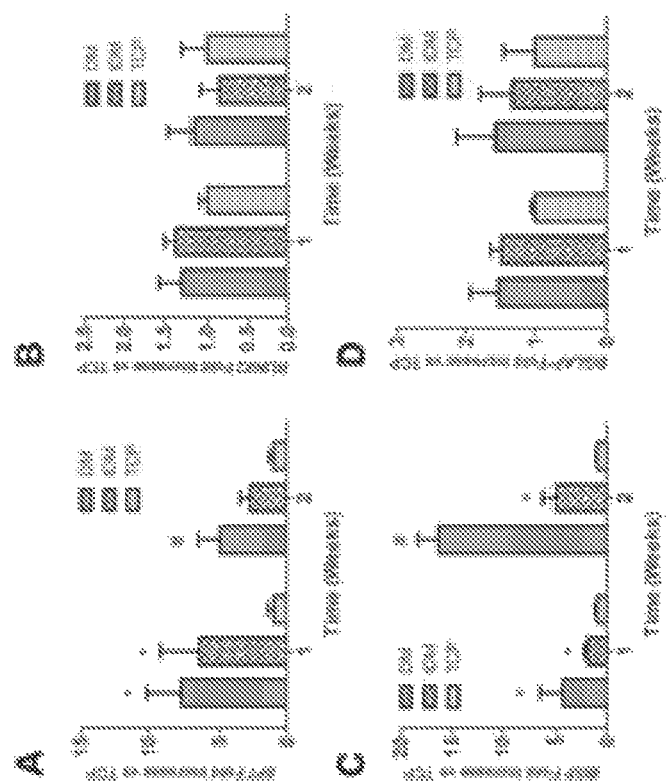
FIG. 15. Quantitative PCR results for genes monitored in hMSCs cultured on DMs, tDMs and TCP and differentiated for one or two weeks: (A) SP7, (B) RUNX2, (C) IBSP, (D) BGLAP. Data were normalized to MRPL13 transcript level and reported as fold change in mRNA expression compared to TCP controls. #p<0.05 vs. all groups; *p<0.05 vs. TCP (n=4).

The expression of osteogenic transcription factors RUNX2 and osterix (SP7) were compared within cells cultured on DMs, tDMs and TCP as markers of hMSC osteogenic differentiation. SP7 expression was approximately 7-fold higher in cells cultured on both DMs and tDMs compared to cells cultured on TCP after 1 week (FIG. 15A). However, SP7 expression remained significantly higher only in hMSCs cultured on DMs after 2 weeks. RUNX2 expression levels trended slightly higher in cells cultured on both DM- and tDM-coated wells compared to TCP at 1 week (FIG. 15B).

Osteocalcin (BGLAP) and bone sialoprotein (IBSP) expression were analyzed due to their role in bone formation and mineralization, as well as our previous observation of significantly higher expression of these markers in hMSCs cultured on DMs compared to TCP.[10] We observed significant increases in IBSP expression in hMSCs cultured on both DMs and tDMs compared to cells cultured on TCP at both time points (FIG. 15C). Similar to SP7 expression, IBSP expression was statistically similar in hMSCs at 1 week, but cells on DM-coated wells exhibited significantly higher levels after 2 weeks compared to hMSCs on tDMs or TCP. BGLAP expression trended slightly higher in hMSCs cultured on DMs and tDMs compared to TCP (FIG. 15D).

Figure 16:
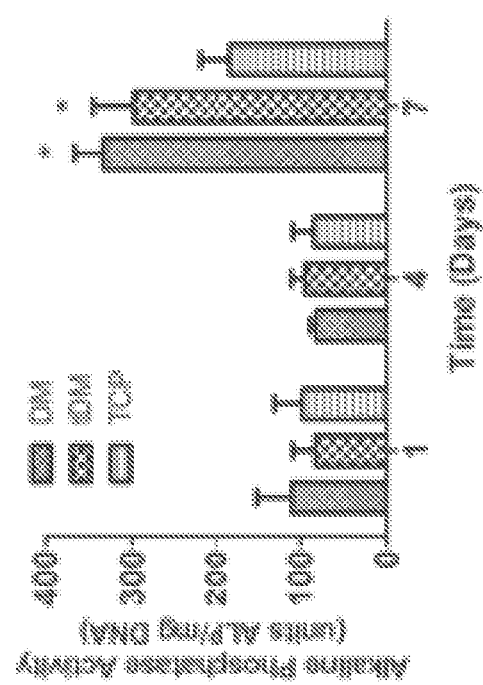
FIG. 16. Intracellular alkaline phosphatase activity from hMSCs cultured on DMs, tDMs and TCP. *p<0.05 vs. TCP (n=4).

We detected similar and significantly higher ALP activity in hMSCs cultured on DMs and tDMs after 7 days compared to cells cultured on TCP (FIG. 16). We did not observe increases in ALP activity at 1 and 4 days, and no significant differences were noted between cells cultured on DMs and tDMs at any time point.

Figure 17:
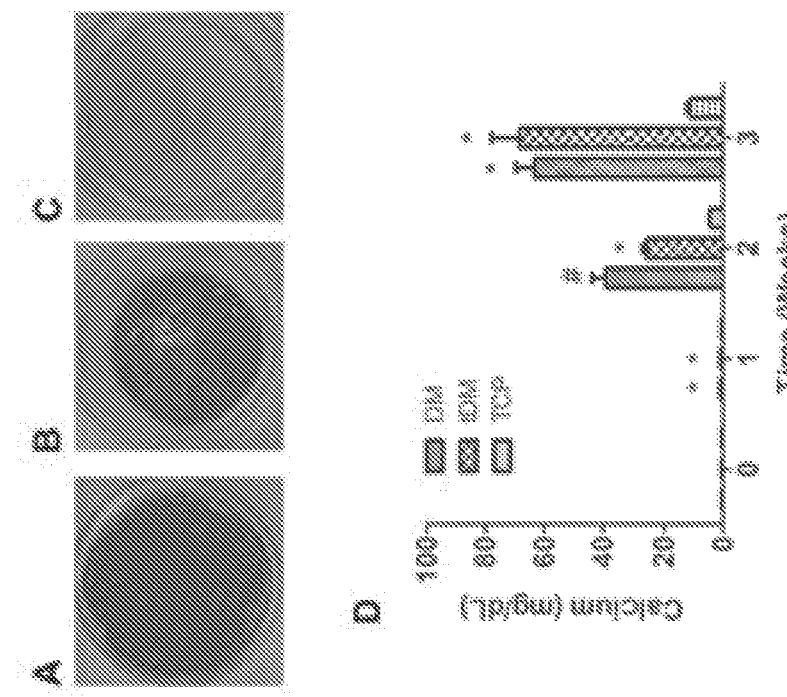
FIG. 17. Alizarin red staining of fixed hMSC layers cultured for 3 weeks on (A) DM, (B) tDM, and (C) TCP. (D) Quantitative analysis of calcium deposited by hMSCs cultured on DMs, tDMs and TCP. #p<0.05 vs. all groups; *p<0.05 vs. TCP (n=4).

Following Alizarin red staining of cells cultured on each matrix, we observed little appreciable calcium deposition at 0 and 1 week. However, more intense staining was apparent on both surfaces after 2 and 3 weeks in culture (FIG. 17A, B). hMSCs cultured on TCP displayed only light staining even after 3 weeks in culture (FIG. 17C). Quantitative analysis of calcium content on each well was consistent with 6 to 9-fold increases in calcium deposits present in DM and tDM-coated wells compared to cells on TCP wells after 2 and 3 weeks (FIG. 17D). Cells cultured on DM- and tDM-coated wells produced similar levels of calcium at each time point with the exception of 2 weeks, when cells on DM-coated wells exhibited significantly greater levels. No appreciable levels of calcium were detected in DMs or tDMs prior to reseeding with hMSCs.

Dose Dependence of hMSCs to tDM

Figure 18:
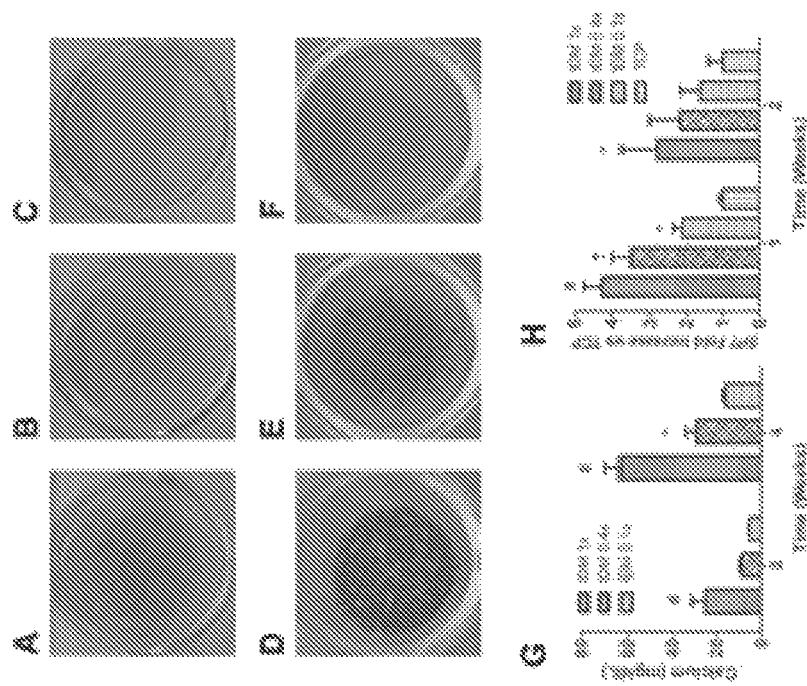
FIG. 18. Analysis of hMSCs cultured on tDMs deposited at different concentrations. tDMs stained with Coomassie brilliant blue at (A) 1×, (B) 0.4× and (C) 0.1× concentration. Alizarin red staining of hMSCs cultured on tDM at (D) 1×, (E) 0.4×, and (F) 0.1× at 2 weeks. (G) Calcium deposited by hMSCs cultured on each substrate. (H)SP7 expression in hMSCs cultured on each substrate. #p<0.05 vs. all groups; †p<0.05 vs. 0.1× tDM and TCP; *p<0.05 vs. TCP (n=4).

Cells were cultured on tDMs at three distinct concentrations to assess its effect on osteogenic differentiation and mineral deposition of hMSCs. The gradient of protein concentration within the transferred coatings (1×, 0.4×, and 0.1×) was visualized using a Coomassie brilliant blue stain (FIG. 18A-C). Calcium deposition by hMSCs cultured on tDMs directly correlated with tDM surface concentration, as determined both qualitatively by Alizarin red staining at 2 weeks (FIG. 18D-F), and with quantitative analysis carried out at 2 and 4 weeks (FIG. 18G). SP7 expression in reseeded hMSCs also directly correlated with tDM surface protein concentrations, as increasing protein concentrations translated into significantly increased levels of gene expression at 1 week (FIG. 18H).

Integrin-mediated Cellular Attachment to tDMs

Figure 19:
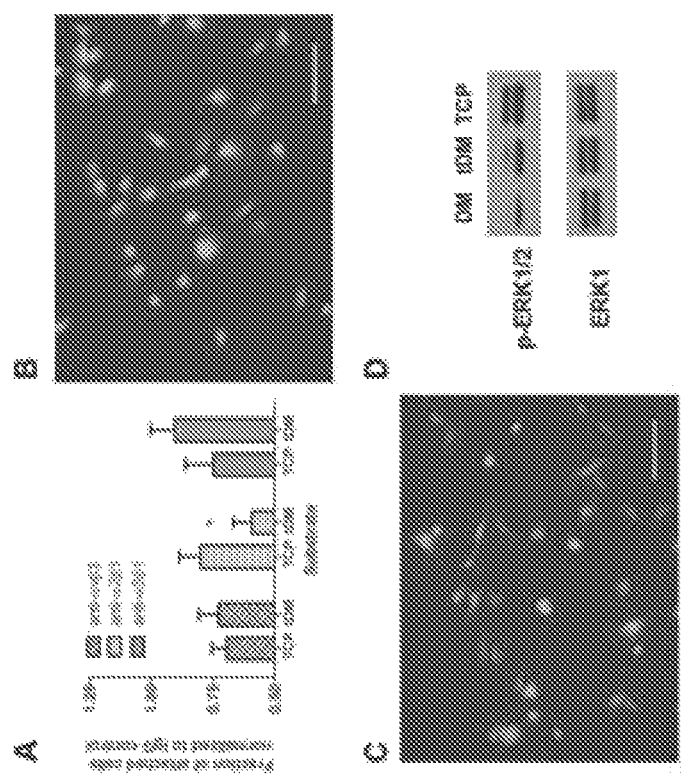
FIG. 19. hMSC attachment, morphology and activation of intracellular signaling pathways. (A) Reduction in hMSC adhesion to tDMs and TCP was analyzed in the presence of antibodies blocking integrins for $\alpha_v\beta_3$, $\alpha_2\beta_1$, and $\alpha_5\beta_1$; *p<0.05 vs. TCP (n=3). Fluorescent microscopy of calcein-treated hMSCs bound to (B) TCP and (C) tDM at 1 h (200×; scale bar=100 μm). (D) ERK1/2 phosphorylation in hMSCs cultured on DMs, tDMs and TCP at 1 week.

The adhesion of MSC to underlying surfaces and the subsequent activation of osteogenic intracellular signaling pathways are mediated by cell surface integrins [3, 28]. We analyzed the contribution of three integrins, $\alpha_2\beta_1$, $\alpha_v\beta_3$, and $\alpha_5\beta_1$ for their role in mediating hMSC attachment to tDMs and TCP. Cells incubated with antibodies to $\alpha_v\beta_3$ and $\alpha_5\beta_1$ prior to seeding exhibited reduced adhesion to TCP (30.5% and 25.0%, respectively) compared to tDMs (27.1% and 9.6%, respectively) (FIG. 19A). However, cells incubated with an antibody to $\alpha_2\beta_1$ exhibited a significant reduction in attachment to tDMs (40.7%) compared to TCP (19.9%), suggesting the importance of $\alpha_2\beta_1$-mediated binding for cells cultured on tDMs. Calcein-stained hMSCs cultured on TCP for 1 h exhibited a flat morphology (FIG. 19B), while hMSCs on tDMs possessed a more elongated, spindle-like morphology (FIG. 19C).

ERK Phosphorylation

ERK1/2 phosphorylation was measured in hMSCs cultured on DMs, tDMs, and TCP after 7 days due to its role in regulating hMSC osteogenic differentiation [29] and to further characterize DM efficacy. We observed reduced ERK1/2 phosphorylation within hMSCs cultured on both DMs and tDMs compared to cells cultured on TCP (FIG. 19D). Cells on DM-coated wells appeared to have slightly less phosphorylation than those on tDM-coated wells.

CONCLUSIONS

Transferred decellularized matrices (tDMs) were created by culturing human mesenchymal stem cells (hMSCs) on tissue culture plastic (TCP) under a controlled microenvironment to deposit a highly osteogenic DM, followed by collection, mechanical homogenization, and transfer to a secondary culture surface. We then investigated its capacity to accelerate naïve hMSC osteogenic differentiation by quantifying gene expression, intracellular alkaline phosphatase production, and calcium deposition when cultured on DMs or tDMs. All markers were significantly higher in hMSCs seeded on DMs or tDMs compared to cells on TCP. The osteogenic response of naïve hMSCs to tDMs was dose dependent. We observed a reduction in ERK phosphorylation in hMSCs, as well as a possible role of the cell surface integrin $\alpha_2\beta_1$, when probing the mode of efficacy for tDMs. This study demonstrates that cell-derived matrix coatings can be deposited and effectively transferred while retaining the ability to instruct cell phenotype, thus offering a new approach toward the development of hybrid biomaterials that mimic the complex interactions between cells and the extracellular matrix.

REFERENCES FOR EXAMPLE 4

1. Hynes R O. The extracellular matrix: not just pretty fibrils. Science 2009 27; 326:1216-1219.
2. Schultz G S, Wysocki A. Interactions between extracellular matrix and growth factors in wound healing. Wound Repair Regen 2009; 17:153-162.
3. Hidalgo-Bastida L A, Cartmell S H. Mesenchymal stem cells, osteoblasts and extracellular matrix proteins: enhancing cell adhesion and differentiation for bone tissue engineering. Tissue Eng Part B Rev 2010; 16:405-412.
4. Shekaran A, Garcia A J. Extracellular matrix-mimetic adhesive biomaterials for bone repair. J Biomed Mater Res A 2011; 96:261-272.
5. Lutolf M P, Hubbell J A. Synthetic biomaterials as instructive extracellular microenvironments for morphogenesis in tissue engineering. Nat Biotechnol 2005; 23:47-55.
6. Gilbert T W, Sellaro T L, Badylak S F. Decellularization of tissues and organs. Biomaterials 2006; 27:3675-3683.
7. Badylak S F, Freytes D O, Gilbert T W. Extracellular matrix as a biological scaffold material: Structure and function. Acta Biomater 2009; 5:1-13.
8. Datta N, Holtorf H L, Sikavitsas V I, Jansen J A, Mikos A G. Effect of bone extracellular matrix synthesized in vitro on the osteoblastic differentiation of marrow stromal cells. Biomaterials 2005; 26:971-977.
9. Hoshiba T, Lu H, Kawazoe N, Chen G. Decellularized matrices for tissue engineering. Expert Opin Biol Ther 2010; 10:1717-1728.
10. Decaris M L, Leach J K. Design of experiments approach to engineer cell-secreted matrices for directing osteogenic differentiation. Ann Biomed Eng 2011; 39:1174-1185.
11. Panetta N J, Gupta D M, Quarto N, Longaker M T. Mesenchymal cells for skeletal tissue engineering. Panminerva Med 2009; 51:25-41.
12. Pittenger M F, Mackay A M, Beck S C, Jaiswal R K, Douglas R, Mosca J D, et al. Multilineage potential of adult human mesenchymal stem cells. Science 1999; 284:143-147.
13. Pham Q P, Kasper F K, Scott Baggett L, Raphael R M, Jansen J A, Mikos A G. The influence of an in vitro generated bone-like extracellular matrix on osteoblastic gene expression of marrow stromal cells. Biomaterials 2008; 29:2729-2739.

14. Hoshiba T, Kawazoe N, Tateishi T, Chen G. Development of stepwise osteogenesis-mimicking matrices for the regulation of mesenchymal stem cell functions. J Biol Chem 2009; 284:31164-31173.
15. Chen X D. Extracellular matrix provides an optimal niche for the maintenance and propagation of mesenchymal stem cells. Birth Defects Res C Embryo Today 2010; 90:45-54.
16. Davis H E, Leach J K. Designing bioactive delivery systems for tissue regeneration. Ann Biomed Eng 2011; 39:1-13.
17. Bancroft G N, Sikavitsas V I, van den Dolder J, Sheffield T L, Ambrose C G, Jansen J A, et al. Fluid flow increases mineralized matrix deposition in 3D perfusion culture of marrow stromal osteoblasts in a dose-dependent manner. Proc Natl Acad Sci USA 2002; 99:12600-12605.
18. Choi K M, Seo Y K, Yoon H H, Song K Y, Kwon S Y, Lee H S, et al. Effect of ascorbic acid on bone marrow-derived mesenchymal stem cell proliferation and differentiation. J Biosci Bioeng 2008; 105:586-594.
19. Sheffield J B, Graff D, Li H P. A solid-phase method for the quantitation of protein in the presence of sodium dodecyl sulfate and other interfering substances. Anal Biochem 1987; 166:49-54.
20. Schmittgen T D, Livak K J. Analyzing real-time PCR data by the comparative C(T) method. Nat Protoc 2008; 3:1101-1108.
21. He J, Genetos D C, Yellowley C E, Leach J K. Oxygen tension differentially influences osteogenic differentiation of human adipose stem cells in 2D and 3D cultures. J Cell Biochem 2010; 110:87-96.
22. Davis H E, Rao R R, He J, Leach J K. Biomimetic scaffolds fabricated from apatite-coated polymer microspheres. J Biomed Mater Res A 2009; 90:1021-1031.
23. Mi Z, Bhattacharya S D, Kim V M, Guo H, Talbot L J, Kuo P C. Osteopontin promotes CCL5-mesenchymal stromal cell-mediated breast cancer metastasis. Carcinogenesis 2011; 32:477-87.
24. Rahman S, Aitken A, Flynn G, Formstone C, Savidge G F. Modulation of RGD sequence motifs regulates disintegrin recognition of alphaIIb beta3 and alpha5 beta1 integrin complexes. Replacement of elegantin alanine-50 with proline, N-terminal to the RGD sequence, diminishes recognition of the alpha5 beta1 complex with restoration induced by Mn2+ cation. Biochem J 1998; 335:247-57.
25. Allori A C, Sailon A M, Warren S M. Biological basis of bone formation, remodeling, and repair-part II: extracellular matrix. Tissue Eng Part B Rev 2008; 14:275-283.
26. Mochida Y, Parisuthiman D, Pornprasertsuk-Damrongsri S, Atsawasuwan P, Sricholpech M, Boskey A L, et al. Decorin modulates collagen matrix assembly and mineralization. Matrix Biol 2009; 28:44-52.
27. Parisuthiman D, Mochida Y, Duarte W R, Yamauchi M. Biglycan modulates osteoblast differentiation and matrix mineralization. J Bone Miner Res 2005; 20:1878-1886.
28. Kundu A K, Khatiwala C B, Putnam A J. Extracellular matrix remodeling, integrin expression, and downstream signaling pathways influence the osteogenic differentiation of mesenchymal stem cells on poly(lactide-co-glycolide) substrates. Tissue Eng Part A 2009; 15:273-283.
29. Jaiswal R K, Jaiswal N, Bruder S P, Mbalaviele G, Marshak D R, Pittenger M F. Adult human mesenchymal stem cell differentiation to the osteogenic or adipogenic lineage is regulated by mitogen-activated protein kinase. J Biol Chem 2000; 275:9645-9652.
30. Sun Y, Li W, Lu Z, Chen R, Ling J, Ran Q, et al. Rescuing replication and osteogenesis of aged mesenchymal stem cells by exposure to a young extracellular matrix. FASEB J 2011; 25:1474-1485.
31. Liao J, Guo X, Grande-Allen K J, Kasper F K, Mikos A G. Bioactive polymer/extracellular matrix scaffolds fabricated with a flow perfusion bioreactor for cartilage tissue engineering. Biomaterials 2010; 31:8911-8920.
32. Liao J, Guo X, Nelson D, Kasper F K, Mikos A G. Modulation of osteogenic properties of biodegradable polymer/extracellular matrix scaffolds generated with a flow perfusion bioreactor. Acta Biomater 2010; 6:2386-2393.
33. Lu H, Hoshiba T, Kawazoe N, Chen G. Autologous extracellular matrix scaffolds for tissue engineering. Biomaterials 2011; 32:2489-2499.
34. Porter B, Zauel R, Stockman H, Guldberg R, Fyhrie D. 3-D computational modeling of media flow through scaffolds in a perfusion bioreactor. J Biomech 2005; 38:543-549.
35. Bhat A, Boyadjiev S A, Senders C W, Leach J K. Differential growth factor adsorption to calvarial osteoblast-secreted extracellular matrices instructs osteoblastic behavior. PLoS One 2011.
36. Grunert M, Dombrowski C, Sadasivam M, Manton K, Cool S M, Nurcombe V. Isolation of a native osteoblast matrix with a specific affinity for BMP2. J Mol Histol 2007; 38:393-404.
37. Manton K J, Leong D F, Cool S M, Nurcombe V. Disruption of heparan and chondroitin sulfate signaling enhances mesenchymal stem cell-derived osteogenic differentiation via bone morphogenetic protein signaling pathways. Stem Cells 2007; 25:2845-2854.
38. Singelyn J M, DeQuach J A, Seif-Naraghi S B, Littlefield R B, Schup-Magoffin P J, Christman K L. Naturally derived myocardial matrix as an injectable scaffold for cardiac tissue engineering. Biomaterials 2009; 30:5409-5416.
39. Lund A W, Stegemann J P, Plopper G E. Inhibition of ERK promotes collagen gel compaction and fibrillogenesis to amplify the osteogenesis of human mesenchymal stem cells in three-dimensional collagen I culture. Stem Cells Dev 2009; 18:331-341.
40. Im D D, Kruger E A, Huang W R, Sayer G, Rudkin G H, Yamaguchi D T, et al. Extracellular-signal-related kinase 1/2 is responsible for inhibition of osteogenesis in three-dimensional cultured MC3T3-E1 cells. Tissue Eng Part A 2010; 16:3485-3494.
41. Thibault R A, Scott Baggett L, Mikos A G, Kasper F K. Osteogenic differentiation of mesenchymal stem cells on pregenerated extracellular matrix scaffolds in the absence of osteogenic cell culture supplements. Tissue Eng Part A 2010; 16:431-440.

Example 5

Cell-Derived Matrix Coatings for Polymeric Scaffolds

Materials and Methods
Scaffold Preparation
Scaffold preparation was carried out using a gas foaming/particulate leaching method as described.(23) Briefly, microspheres composed of PLG (85:15 DLG 7E; Lakeshore Biomaterials, Birmingham, Ala.) were prepared using a double-emulsion process. Lyophilized PLG microspheres were mixed with NaCl particles (250-425 µm in diameter) and compressed into solid disks (final dimensions: 8.5 mm diameter and 1.5 mm thickness) in a custom-made stainless steel die using a Carver press (Fred S. Carver, Wabash, Ind.) for 1 min. Compressed disks were then exposed to high pressure $CO_2$ gas (5.5 MPa) for 16 h followed by rapid pressure release. NaCl particles were leached from scaffolds by submersion in distilled $H_2O$ for 24 h. Scaffolds were functionalized with 0.1 N NaOH for 1 min and placed in a sealed 50 mL Steriflip (Millipore) conical tube with 95% EtOH under gentle vacuum for 30 min for sterilization. Scaffolds were then rinsed twice under vacuum with sterile PBS and used immediately.

Cell Culture

Human bone marrow-derived MSCs (MSCs, Lonza, Walkersville, Md.) were expanded in minimum essential alpha medium (α-MEM w/L-glutamine, w/o ribo/deoxyribonucleosides; Cat. #12000-022, Invitrogen, Carlsbad, Calif.) supplemented with 10% fetal bovine serum (FBS, JR Scientific, Woodland, Calif.) and 1% penicillin and streptomycin (P/S, Mediatech, Manassas, Va.). Cells were cultured under standard conditions and utilized at passages 4-6. Supplemented medium (SM) containing 50 μg/mL ascorbate-2-phosphate was utilized on all cells for one passage prior to experimental use to prime cells for enhanced matrix deposition.(24) Osteogenically pre-conditioned cells were cultured in full osteogenic medium (OM) further supplemented with 10 mM β-glycerophosphate and 10 nM dexamethasone for 5 d prior to use.

Preparation of Decellularized Matrices (DMs)

DMs were prepared as previously described.(18) Briefly, MSCs were seeded on 6-well plates at 50,000 cells/$cm^2$ and cultured in supplemented media (SM: α-MEM, 10% FBS, 1% P/S, 50 μg/mL A2P) for 15 d under standard culture conditions with media changes performed every 3 d. Wells were then rinsed with PBS and treated with 0.5% Triton X-100 (Sigma, St. Louis, Mo.) in 20 mM $NH_4OH$ in PBS for 5 min at 37° C. Following an additional PBS rinse, wells were treated with DNAse (Sigma, 150 units/mL PBS) for 1 h at 37° C. and again rinsed in PBS. Plates were then allowed to dry in a sterile biosafety cabinet for up to 12 h and stored at room temperature in the dark for up to 1 month prior to use.

Transfer of DMs to 3-D Scaffolds

Homogenized DM solutions were prepared similarly to that previously described.(21) Briefly, 6-well DM-coated plates were scraped in the presence of sterile 0.02 N acetic acid (50 μl per well), DM contents transferred to microcentrifuge tubes, and sonicated (Sonics & Materials Vibra-Cell VCX130PB) on ice with 2-3 s pulses 10-15 times to mechanically homogenize DM contents. DM contents were brought to a final concentration of 500 μg per ml prior to seeding.

Sterilized scaffolds were placed on sterile gauze to remove excess PBS and transferred to the surface of a Steritop (Millipore) vacuum filter attached to a 500 mL glass bottle. 50 μL of DM solution (acetic acid only for sham-coated scaffolds) was then added drop wise to the surface of each scaffold via micropipettor, followed by the application of a gentle vacuum to the bottom of the scaffolds to ensure absorption of the DM solution. When they appeared dry (approx. 15-30 mins), scaffolds were inverted and an equal volume of DM solution was applied to their opposite side. Scaffolds were then allowed to dry overnight under vacuum in a sterile biosafety cabinet. Scaffolds were rinsed in cell culture media (2×30 min) prior to cell seeding.

Cell Seeding tDM and sham-coated scaffolds were seeded with either naïve MSCs or osteogenically pre-conditioned MSCs. MSCs ($7.5 \times 10^5$ cells per scaffold) were reconstituted in a volume of 35 μL of media and applied drop wise to the scaffold surface. Scaffolds were placed in standard cell culture incubators (37° C., 5% $CO_2$) for 3 h to allow cell attachment. Scaffolds were then transferred to 12-well plates containing 2 mL of their respective mediums (SM for naïve cells; OM for osteogenically pre-conditioned cells) per well and placed on an XYZ shaker (Stovall) overnight. Scaffolds intended for implantation in vivo were utilized the following morning. For those scaffolds used for in vitro analysis, media was exchanged for OM the following day and every 3 d thereafter.

Scaffold Characterization

Quantification of tDM protein solutions applied to scaffold surfaces was carried out by BCA protein assay (Thermo; #23227) per manufacturer's instructions. MSC-seeded scaffolds cultured in vitro were collected at various time points and imaged for morphological analysis. Scaffold porosity was analyzed using Archimedes' principle as previously described.(23) Scaffolds were also analyzed by SEM to assess matrix coverage and scaffold surface morphology. Scaffolds were gold sputter coated and imaged at 50 and 2500× using a Hitachi S3500-N.

DNA Quantification

Total DNA present in scaffolds was determined using the Quant-iT PicoGreen dsDNA kit (Invitrogen), Briefly, cell-seeded scaffolds were rinsed in PBS, minced, and placed in passive lysis buffer (Promega). Following a freeze thaw cycle, the lysate was sonicated briefly, separated from the scaffold material via centrifugation, and quantified in comparison to a known standard curve.

Osteogenic Marker Analysis

PCR

Total RNA from scaffolds was collected following 1 or 2 wks in culture. Scaffolds were rinsed 1× in sterile PBS, minced with a sterile scalpel, and placed in 350 μL of RLT buffer (Qiagen, Valencia, Calif.) supplemented with 10 μL/mL β-mercaptoethanol. Total RNA was purified using the RNeasy Mini kit (Qiagen) and 400 ng of total RNA reverse-transcribed with the QuantiTect Reverse Transcription Kit (Qiagen). qPCR was performed using TaqMan1 Universal PCR Master Mix (Applied Biosystems, Foster City, Calif.) on a Mastercycler1 realplex2 (Eppendorf, Westbury, N.Y.); primers and probes for BGLAP (Hs01587814_g1), IBSP (Hs00173720_m1), MRPL13 (Hs00204173_m1), RUNX2 (Hs00231692_m1), SP7 (Hs01866874_s1), and VEGFA (Hs00900055_m1), were purchased from Applied Biosystems. Amplification conditions were 50° C. for 2 min, 95° C. for 10 min, followed by 40 cycles at 95° C. for 15 s and 60° C. for 1 min. Quantitative PCR results were normalized to RPL13 transcript level to yield ΔCt values.

Alkaline Phosphatase and Calcium Quantitation

Intracellular alkaline phosphatase (ALP) from MSCs seeded on tDM and sham-coated scaffolds was quantified using a PNPP colorimetric assay at 405 nm as described.(25) ALP activity was normalized to DNA content determined as described above. Total calcium present on MSC-seeded scaffolds was determined using an OCOP colorometric assay similar to that previously described.(25) Briefly, minced scaffolds were incubated in 0.9 N overnight to solubilize surface calcium deposits. Calcium concentration in solution was then quantified in comparison to a known standard curve.

Ectopic Model of Bone Formation

Treatment of experimental animals was in accordance with University of California, Davis animal care guidelines and all National Institutes of Health animal-handling procedures. 10-week old male nude rats (n=6 per group) were anesthetized and maintained using 2% isoflurane with $O_2$ flow at 2 L/min delivered through a mask. Four pockets were created in the dorsum, and scaffolds were subcutaneously implanted. Scaffolds were collected following euthanization at 2 and 8 wks. Scaffolds were fixed overnight in 10% formalin followed by storage in 70% ethanol at 4° C. Scaffolds were demineralized (8 wk only) overnight prior to histological analysis with CalciClear (National Diagnostics), then bisected, paraffin embedded and sectioned at 5 μm.

Vessel Quantification

Vessel quantification was performed at 2 wks using H&E stained scaffold cross-sections at 100× magnification similar to that previously described.(23) Vessels were enumerated from H&E-stained sections by counting circular structures with well-defined lumens containing erythrocytes. The presence of human cells was determined by immunohistochemistry using antibodies for human nuclear antigen (HNA, MAB1281, Millipore, Billerica, Mass.; 1:20) and a mouse specific HRP/DAB detection kit (Abcam; ab64259).

Micro CT Analysis

Scaffolds removed from animals after 8 wks were assessed for mineralization prior to decalcification for histology. Bone volume fraction (BVF) and bone mineral density (BMD) were determined using microcomputed tomography. Bone tissue in the reconstructed images was determined by thresholding (>85 mg HA/cm$^3$) to partition mineralized tissue from fluid and soft-tissues. Bone volume fraction (BVF) was determined by dividing the number of pixels representing bone tissue (bone volume) by the number of pixels in the cylindrical segment (total volume). The mean density of the bone material or BMD was calculated as the average density (mg HA/cc) of the bone volume fraction.

Statistical Analysis

Results are expressed as mean±standard error of the mean (SEM). Statistical analyses were performed by ANOVA followed by Student-Newman-Keuls post-hoc tests assessing significance to probability values (p)<0.05.

Results

Characterization of tDM-Coated Scaffolds

Figure 20:
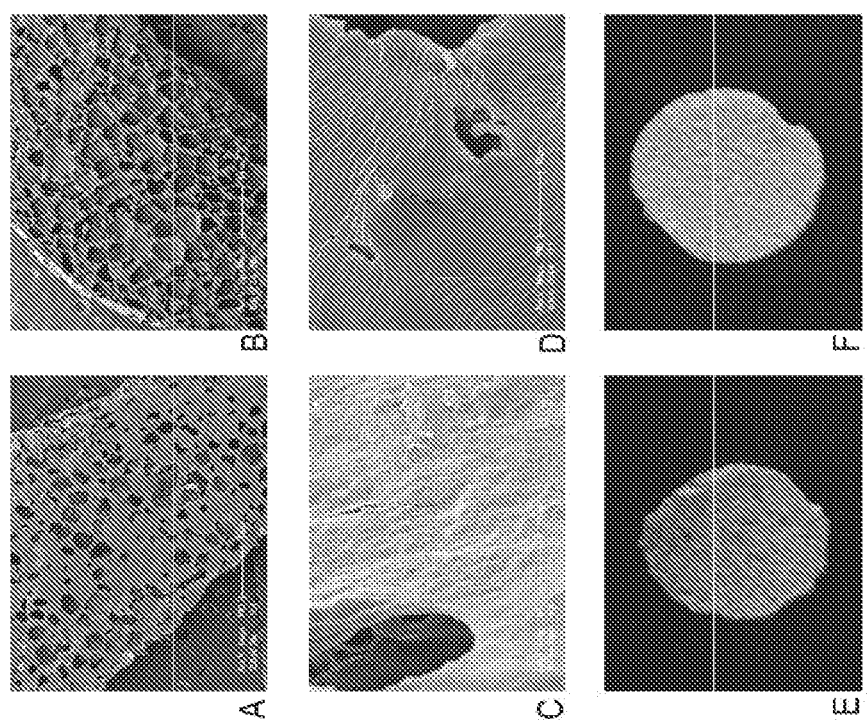
FIG. 20. Characterization of tDM scaffold coating. SEM images of tDM-coated scaffolds at 20× (A) and 2500× (C). SEM images of uncoated scaffolds at 20× (B) and 2500× (D). Image of Coomassie Brilliant Blue stained tDM-coated (E) and uncoated scaffold (F).
Figure 21:
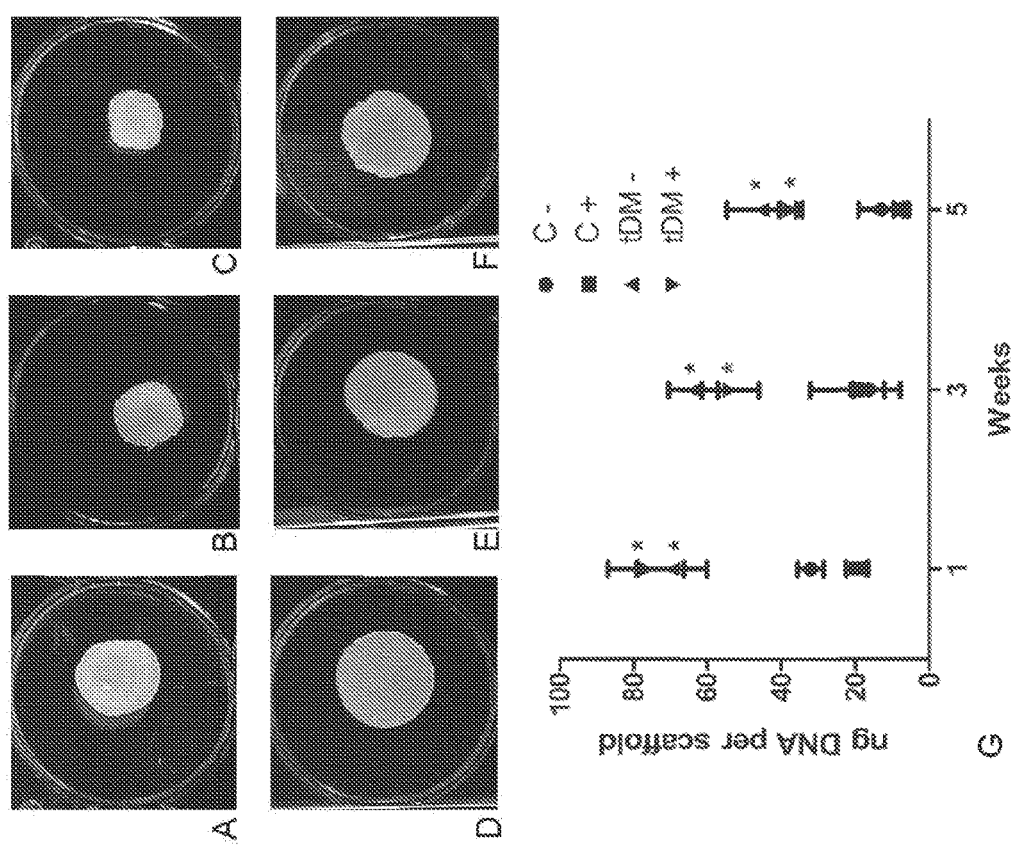
FIG. 21. Analysis of the cellular deformation of tDM-coated scaffolds. Images of naïve MSC-seeded tDM-coated and uncoated scaffolds at 1 (A,D), 3 (B,E), and 5 (C,F) weeks, respectively. (G) DNA quantification from tDM-coated [tDM] and uncoated [C] scaffolds seeded with naïve [−] or osteogenically predifferentiated [+] MSCs. *p<0.05 vs. uncoated scaffolds (C−, C+) (n=4).

Macroporous PLG scaffolds were coated with 52.5±4.8 μg of tDM protein as determined by BCA protein quantification. DM decellularization, as well as the retention of several key proteins and proteoglycans present in bone ECM, has previously been established.(18, 21) tDM-coating of PLG scaffolds was characterized through microscopic and macroscopic analysis. Scanning electron microscopy at 20× magnification revealed a well-distributed coating of DM material over the pores on the scaffold surface (FIG. 20A) when compared to uncoated scaffolds (FIG. 20B). Upon examination at higher magnification (2500×), we detected distinct differences in surface morphology between tDM-coated and uncoated scaffolds. The surfaces of coated scaffolds exhibited a rough topography (FIG. 20C), while control scaffolds were much smoother (FIG. 20D). Coomassie brilliant blue total protein staining of scaffolds demonstrated even distribution of protein throughout the scaffold surface (FIG. 20E), while little to no apparent staining was seen on uncoated scaffolds (FIG. 20F). An analysis of bulk scaffold porosity between tDM-coated and uncoated scaffolds revealed no significant differences (data not shown).

tDM-coated (tDM) and uncoated (C) scaffolds were then seeded with either naïve (−) or osteogenically pre-conditioned (+) MSCs. Cell-seeded scaffolds were monitored for morphological differences at 1, 3, and 5 weeks. Scaffold curling, thought to occur as a result of cell-mediated mechanical forces applied to the scaffold surface, was evident at increasing magnitudes for tDM scaffolds seeded with both cell types (FIG. 21A-C), while non-coated scaffolds displayed little to no curling (FIG. 21D-F). Total DNA quantification performed on each cell/scaffold combination revealed significantly more cells on tDM-coated scaffolds compared to control scaffolds (FIG. 21G).

In Vitro Osteogenic Response to tDM-Coated Scaffolds

Figure 22:
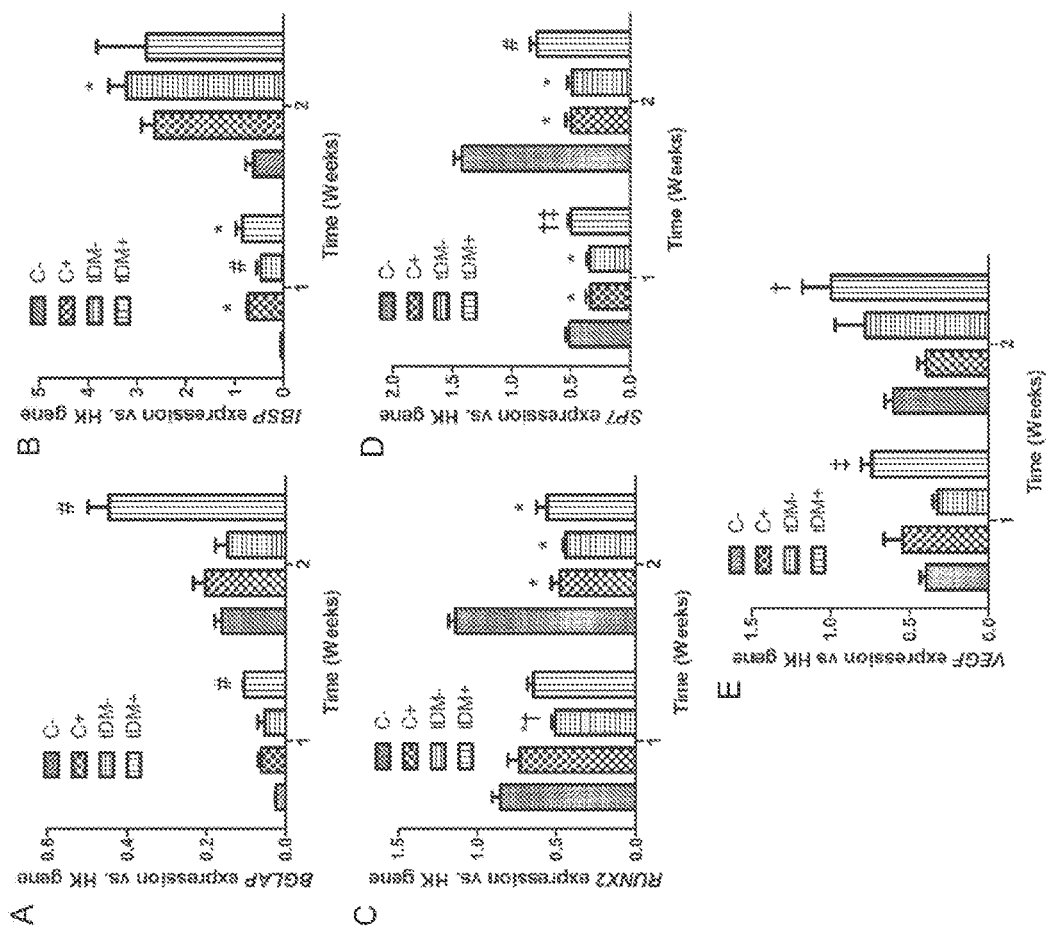
FIG. 22. qPCR analysis of MSC gene expression. tDM-coated [tDM] and uncoated [C] scaffolds seeded with naïve [−] or osteogenically predifferentiated hMSCs [+] were collected after 1 and 2 weeks. *p<0.05 vs. C−; t†p<0.05 vs. C+; ‡p<0.05 vs. tDM−; #p<0.05 vs. all other groups (n=3-6).

Naïve MSCs and osteogenically-preconditioned MSCs were cultured on tDM and uncoated scaffolds and monitored for the expression of several different markers of osteogenic differentiation. qPCR analysis was utilized to assess MSC expression of osteocalcin (BGLAP) and bone sialoprotein (IBSP), two markers of mature osteoblast function. Osteocalcin expression was significantly enhanced in osteogenically predifferentiated MSCs cultured on tDM-coated scaffolds at 1 and 2 weeks (FIG. 22A). MSC bone sialoprotein expression was significantly enhanced by predifferentiation or the presence of a tDM-coating at 1 week, with only the tDM-coating significantly boosting expression after 2 weeks (FIG. 22B). The expression of RUNX2 and SP7 (osterix), two transcription factors related to osteogenic differentiation, was significantly lower in both predifferentiated MSCs and those cultured on tDM-coated scaffolds after 2 weeks (FIG. 22C,D). Finally, MSC expression of vascular endothelial growth factor (VEGF) was assessed under each condition as a marker of the angiogenic potential of MSCs. While the combination of osteogenically pre-differentiated MSCs and control scaffolds resulted in the lowest VEGF expression at 2 weeks, pre-differentiated cells cultured on tDM-coated scaffolds displayed significantly greater VEGF expression (FIG. 22E).

Figure 23:
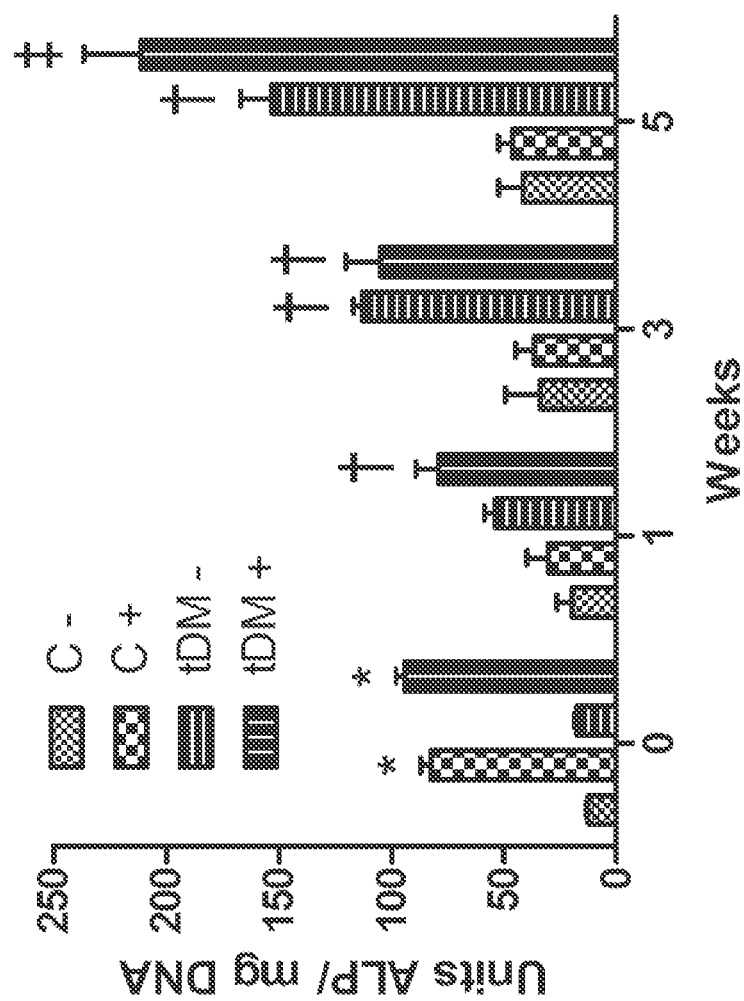
FIG. 23. MSC intracellular alkaline phosphatase quantification. tDM-coated [tDM] and uncoated [C] scaffolds seeded with naïve [−] or osteogenically predifferentiated MSCs [+] were collected at 0, 1, 3 and 5 weeks. *p<0.05 vs. C− and tDM−; †p<0.05 vs. C− and C+; ‡p<0.05 vs. all other groups (n=4).

ALP activity within MSCs seeded on tDM- and uncoated scaffolds also displayed significant differences (FIG. 23). While the pre-conditioning of MSCs in osteogenic medium for 5 days significantly upregulated ALP expression at the time of seeding, both MSC populations cultured on tDM-coated scaffolds had surpassed control-seeded cells in ALP expression by 1 week. MSCs also displayed significantly higher ALP expression when cultured on DM-coated scaffolds compared to control scaffolds at 3 and 5 weeks post seeding.

Figure 24:
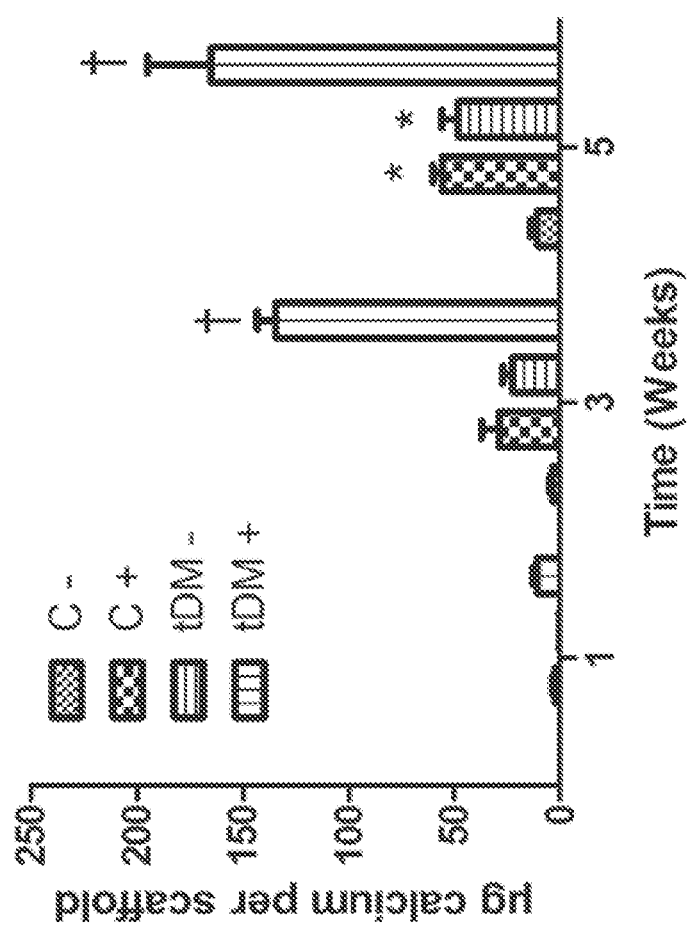
FIG. 24. Quantification of calcium deposition on MSC-seeded scaffolds. tDM-coated [tDM] and uncoated [C] scaffolds seeded with naïve [−] or osteogenically predifferentiated MSCs[+] were collected at 0, 1, 3, and 5 weeks and analyzed for total calcium content. *p<0.05 vs. C−; †p<0.05 vs. all other groups (n=4).

Total calcium deposition from naïve and preconditioned MSCs cultured on tDM-coated and control scaffolds was quantified after 1, 3, and 5 weeks. MSCs preconditioned in osteogenic media and cultured on DM-coated substrates deposited the most calcium over the 5 week culture period, significantly more than all other groups at both 3 and 5 weeks (FIG. 24). In addition, osteogenic preconditioning of MSCs or the culture of MSCs on DM-coated scaffolds alone also resulted in significantly greater calcium deposition compared to naïve MSCs on control scaffolds at week 5.

In Vivo Osteogenic Response to tDM-Coated Scaffolds

Figure 25:
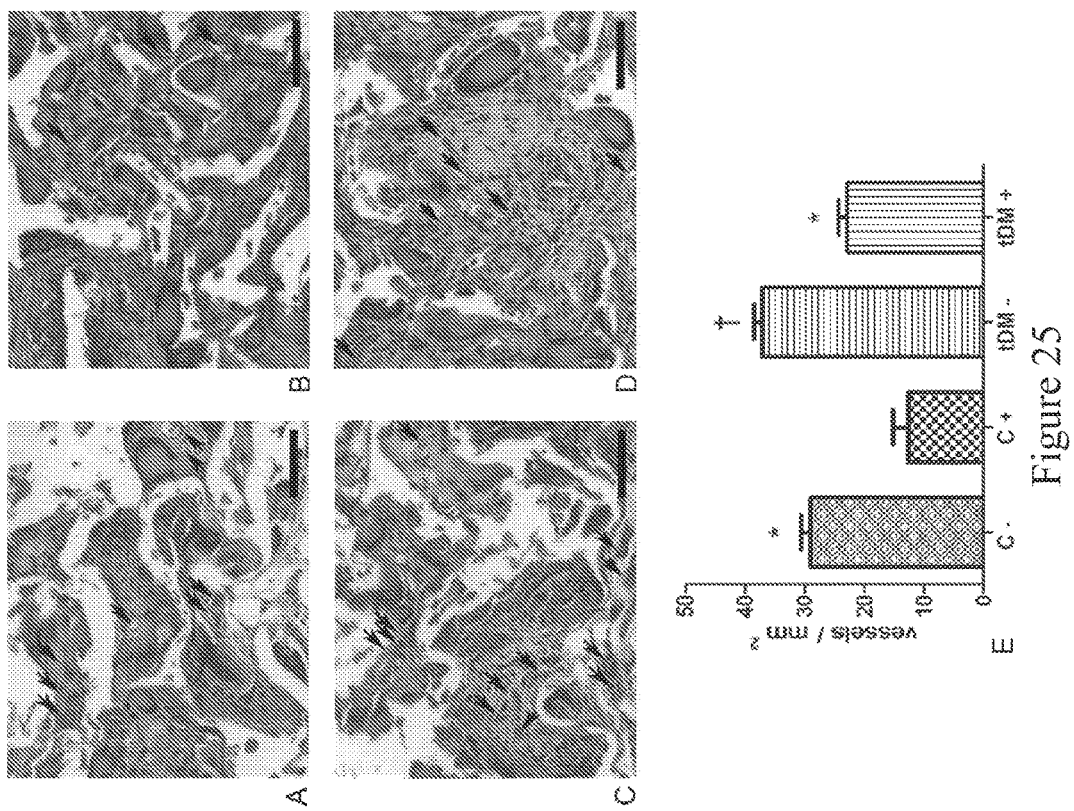
FIG. 25. Vessel quantification in subcutaneously implanted scaffolds. Control scaffolds seeded with naïve (A) or predifferentiated (B) MSCs were compared with tDM-coated scaffolds seeded with the same respective cell types (C, D) at 2 weeks. (E) Quantification of vascular density (vessels/mm$^2$) from random histological sections. Scale bars represent 100 µm; arrows indicative of vessels with defined lumen and erythrocytes; *p<0.05 vs. C+; †p<0.05 vs. all other groups (n=12).

Naïve and preconditioned MSCs seeded onto tDM-coated and control scaffolds were implanted subcutaneously in nude rats to assess the efficacy of the tDM-coating to modulate MSC activity in vivo. Histological sections taken from scaffolds retrieved at 2 weeks revealed significant differences in vessel formation (FIG. 25). Vessel density within the scaffold perimeter was significantly increased in scaffolds coated with tDM compared to uncoated scaffolds, as well as in scaffolds seeded with naïve MSCs compared to predifferentiated MSCs. MSC death or migration from the implant site appeared to have occurred by 2 weeks, as suggested by negative immunohistochemical staining for human nuclear antigen (data not shown).

Figure 26:
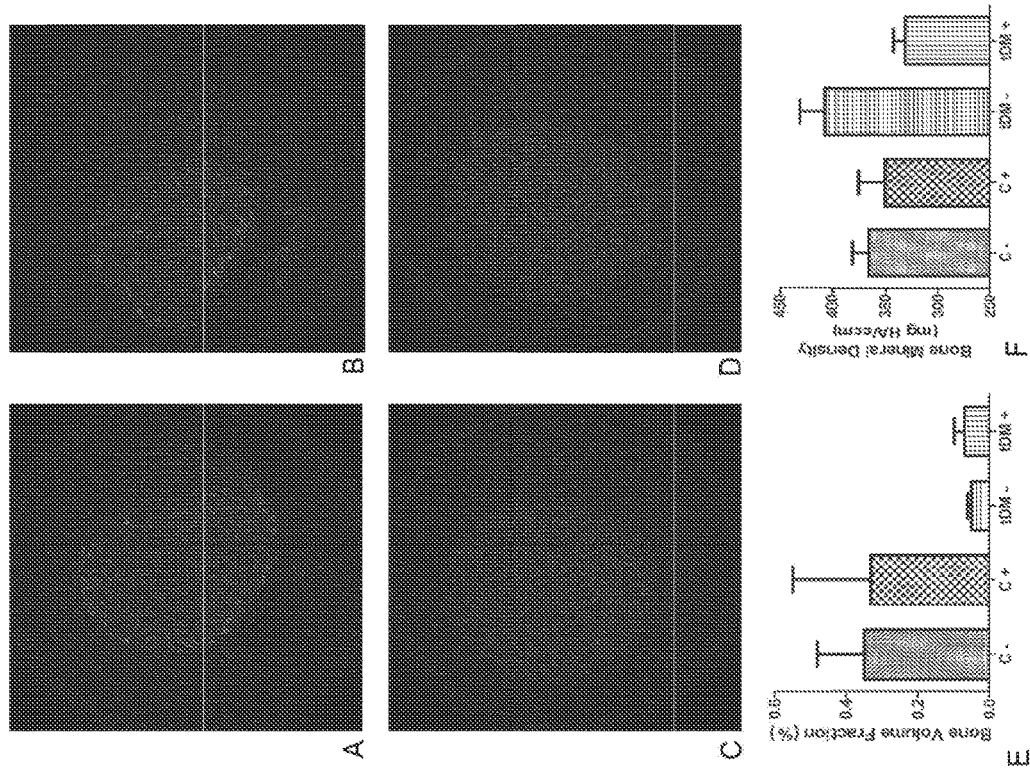
FIG. 26. MicroCT analysis of scaffold mineralization. Image slices from uncoated scaffolds seeded with naïve (A) or predifferentiated (B) MSCs were compared with tDM-coated scaffolds seeded with the same respective cell types (C, D) at 8 weeks. (E) Bone volume fraction (E) and bone mineral density (F) for each scaffold group were also quantified (n=5).

Excised scaffolds analyzed at 8 weeks post implantation revealed no significant differences in scaffold mineralization. MicroCT scans of the scaffolds indicated low levels of mineral formation around the edges of the scaffolds, with a trend for increased mineralization on uncoated scaffolds (FIG. 26A,B) compared to tDM-coated scaffolds (FIG. 26C,D). Quantitative measurements of bone volume fraction also presented a trend for less mineralization in DM coated scaffolds (FIG. 26E). A subsequent analysis of bone mineral density (BMD) for the mineral detected within each group indicated a trend for highest BMD in the naïve MSC seeded tDM-coated scaffolds; however, this result was not significant (p=0.086).

CONCLUSIONS

Biomaterial constructs coated with a cell-derived ECM can instruct cell phenotype. Current techniques used to apply such coatings are time consuming and expensive, as they require convective culture systems and direct contact between matrix-depositing cells and substrate surfaces. This study demonstrates that a cell-derived ECM coating can be collected from a 2-D culture substrate and transferred to a 3-D implantable construct while retaining the capacity to instruct cell phenotype. This technique provides a new tool in advancing the ability of synthetic biomaterials to mimic the properties of native tissue.

REFERENCES FOR EXAMPLE 5

1. Pittenger M F, Mackay A M, Beck S C, Jaiswal R K, Douglas R, Mosca J D, et al. Multilineage potential of adult human mesenchymal stem cells. Science 284, 143, 1999.
2. Panetta N J, Gupta D M, Quarto N, Longaker M T. Mesenchymal cells for skeletal tissue engineering. Panminerva Med 51, 25, 2009.
3. Jaiswal N, Haynesworth S E, Caplan A I, Bruder S P. Osteogenic differentiation of purified, culture-expanded human mesenchymal stem cells in vitro. J Cell Biochem 64, 295, 1997.
4. Jones E, Yang X. Mesenchymal stem cells and bone regeneration: current status. Injury 42, 562, 2011.
5. Caplan A I, Dennis J E. Mesenchymal stem cells as trophic mediators. J Cell Biochem 98, 1076, 2006.
6. Prockop D J, Kota D J, Bazhanov N, Reger R L. Evolving paradigms for repair of tissues by adult stem/progenitor cells (MSCs). J Cell Mol Med 14, 2190, 2010.
7. Chang S C, Chung H Y, Tai C L, Chen P K, Lin T M, Jeng L B. Repair of large cranial defects by hBMP-2 expressing bone marrow stromal cells: comparison between alginate and collagen type I systems. J Biomed Mater Res 94, 433, 2010.
8. Yan M N, Dai K R, Tang T T, Zhu Z A, Lou J R. Reconstruction of peri-implant bone defects using impacted bone allograft and BMP-2 gene-modified bone marrow stromal cells. J Biomed Mater Res 93, 304, 2010.
9. McKay W F, Peckham S M, Badura J M. A comprehensive clinical review of recombinant human bone morphogenetic protein-2 (INFUSE Bone Graft). Int Orthop 31, 729, 2007.
10. Davis H E, Case E M, Miller S L, Genetos D C, Leach J K. Osteogenic response to BMP-2 of hMSCs grown on apatite-coated scaffolds. Biotechnol Bioeng 10, 2727, 2011.
11. Allori A C, Sailon A M, Warren S M. Biological basis of bone formation, remodeling, and repair-part II: extracellular matrix. Tissue Eng Part B Rev 14, 275, 2008.
12. Gentili C, Cancedda R. Cartilage and bone extracellular matrix. Curr Pharm Design 15, 1334, 2009.
13. Hidalgo-Bastida L A, Cartmell S H. Mesenchymal stem cells, osteoblasts and extracellular matrix proteins: enhancing cell adhesion and differentiation for bone tissue engineering. Tissue Eng Part B Rev 16, 405, 2010.
14. Shekaran A, Garcia A J. Extracellular matrix-mimetic adhesive biomaterials for bone repair. J Biomed Mater Res 96, 261, 2010.
15. Sreejalekshmi K G, Nair P D. Biomimeticity in tissue engineering scaffolds through synthetic peptide modifications-altering chemistry for enhanced biological response. J Biomed Mater Res 96, 477, 2011.
16. Chen X D, Dusevich V, Feng J Q, Manolagas S C, Jilka R L. Extracellular matrix made by bone marrow cells facilitates expansion of marrow-derived mesenchymal progenitor cells and prevents their differentiation into osteoblasts. J Bone Miner Res 22, 1943, 2007.
17. Datta N, Holtorf H L, Sikavitsas V I, Jansen J A, Mikos A G. Effect of bone extracellular matrix synthesized in vitro on the osteoblastic differentiation of marrow stromal cells. Biomaterials 26, 971, 2005.
18. Decaris M L, Leach J K. Design of experiments approach to engineer cell-secreted matrices for directing osteogenic differentiation. Ann Biomed Eng 39, 1174, 2011.
19. Liao J, Guo X, Nelson D, Kasper F K, Mikos A G. Modulation of osteogenic properties of biodegradable polymer/extracellular matrix scaffolds generated with a flow perfusion bioreactor. Acta Biomater 6, 2386, 2010.
20. Liao J, Guo X, Grande-Allen K J, Kasper F K, Mikos A G. Bioactive polymer/extracellular matrix scaffolds fabricated with a flow perfusion bioreactor for cartilage tissue engineering. Biomaterials 31, 8911, 2010.
21. Decaris M L, Mojadedi A, Bhat A, Leach J K. Transferable cell-secreted extracellular matrices enhance osteogenic differentiation. Acta Biomater, In Press, 2011.
22. Castano-Izquierdo H, Alvarez-Barreto J, van den Dolder J, Jansen J A, Mikos A G, Sikavitsas V I. Pre-culture period of mesenchymal stem cells in osteogenic media influences their in vivo bone forming potential. J Biomed Mater Res 82, 129, 2007.
23. He J, Genetos D C, Leach J K. Osteogenesis and trophic factor secretion are influenced by the composition of hydroxyapatite/poly(lactide-co-glycolide) composite scaffolds. Tissue Eng Part A 16, 127, 2010.
24. Choi K M, Seo Y K, Yoon H H, Song K Y, Kwon S Y, Lee H S, Park J K. Effect of ascorbic acid on bone marrow-derived mesenchymal stem cell proliferation and differentiation. J Biosci Bioeng 105, 586, 2008.
25. He J, Genetos D C, Yellowley C E, Leach J K. Oxygen tension differentially influences osteogenic differentiation of human adipose stem cells in 2D and 3D cultures. J Cell Biochem 110, 87, 2010.
26. Thibault R A, Scott Baggett L, Mikos A G, Kasper F K. Osteogenic differentiation of mesenchymal stem cells on pregenerated extracellular matrix scaffolds in the absence of osteogenic cell culture supplements. Tissue Eng Part A 16, 431, 2010.
27. Kang Y, Kim S, Khademhosseini A, Yang Y. Creation of bony microenvironment with CaP and cell-derived ECM to enhance human bone-marrow MSC behavior and delivery of BMP-2. Biomaterials 32, 6119, 2011.

28. Nguyen L H, Kudva A K, Guckert N L, Linse K D, Roy K. Unique biomaterial compositions direct bone marrow stem cells into specific chondrocytic phenotypes corresponding to the various zones of articular cartilage. Biomaterials 32, 1327, 2011.
29. Badylak S F, Freytes D O, Gilbert T W. Extracellular matrix as a biological scaffold material: Structure and function. Acta Biomater 5, 1, 2009.
30. Naito H, Dohi Y, Zimmermann W H, Tojo T, Takasawa S, Eschenhagen T, Taniguchi, S. The effect of mesenchymal stem cell osteoblastic differentiation on the mechanical properties of engineered bone-like tissue. Tissue Eng Part A 17, 2321, 2011.
31. Guilak F, Cohen D M, Estes B T, Gimble J M, Liedtke W, Chen C S. Control of stem cell fate by physical interactions with the extracellular matrix. Cell Stem Cell 5, 17, 2009.

Example 6

Alginate Hydrogels Containing Cell-Interactive Beads for Bone Formation

Materials and Methods
Cell Culture

Human bone marrow-derived MSCs (Lonza, Walkersville, Md.) were used without further characterization and cultured in alpha minimum essential medium (MEM, Invitrogen, Carlsbad, Calif.) supplemented with 10% fetal bovine serum (FBS, JR Scientific, Woodland, Calif.) and 1% penicillin and streptomycin (P/S, Mediatech, Manassas, Va.). Cells were used at passages 4-6.

Preparation of Decellularized ECMs and ECM-Coated Microcarrier Beads

We prepared an osteogenic, cell-secreted ECM for transfer to a naïve substrate as previously described (25). Briefly, MSCs were seeded on 12 well plates (80,000 cells/cm$^2$), and cultured in supplemented media (SM: alpha-MEM containing 10% FBS, 1% P/S, and 50 µg/ml ascorbate-2-phosphate) in 21% oxygen. Plates were decellularized based on previously described protocols (25, 26). Wells were rinsed with PBS and treated with 0.5% Triton X-100 and 20 mM NH$_4$OH in PBS (both from Sigma Aldrich, St. Louis, Mo.). The plates were incubated at 37° C. for 5 min, after which the wells were rinsed in PBS and treated with DNAse (Sigma, 200 units/ml in PBS) for 1 h at 37° C. After rinsing, the decellularized ECM was scraped and collected in 50 µl of 0.02 N acetic acid, and total protein was quantified using the amido black method.

Cytodex®3 microcarrier beads (60-87 µm bead size, Sigma) were swelled in PBS for 1 hr and then sterilized overnight in 70% ethanol. The sterilized beads were rinsed 3 times in PBS. ECM was resuspended at a known concentration in acetic acid and added to pre-swelled beads (15 µg protein/mg bead). The acetic acid was allowed to evaporate overnight in a biosafety cabinet, and the resulting ECM-coated beads were mixed with alginate as described below. Heat-inactivated ECM-coated beads were prepared by incubating ECM-coated beads at 70° C. for 15 min just prior to mixing with alginate.

Preparation of Alginate Hydrogels

Four groups of alginate hydrogels were prepared: RGD-modified alginate (RGD), alginate containing uncoated beads (BLK), alginate containing ECM-coated beads (ECM), and alginate containing heat-inactivated ECM-coated beads (HI-ECM). RGD-modified alginate (RGD) was prepared as previously described (11). Briefly, G$_4$RGDSP (Commonwealth Biotechnologies, Richmond, Va.) was covalently coupled to UltraPure MVG sodium alginate (Pronova, Lysaker, Norway) using standard carbodiimide chemistry. The resulting RGD-alginate was sterile filtered and lyophilized for 4 days. Lyophilized alginate was reconstituted in serum-free alpha MEM to obtain a 2.5% (w/v) solution. A final 2% alginate solution was prepared by mixing the 2.5% alginate solution with the cell suspension (5×10$^6$ cells/ml); and 4% (v/v) super saturated CaSO$_4$ ( ) solution using a dual syringe mixing technique. The mix was allowed to gel between two glass plates for 1 h at 37° C. Alginate disks (8 mm diameter, 2 mm thick) were then prepared using a dermal biopsy punch (Acuderm, Ft. Lauderdale, Fla.) and used for subsequent in vitro and in vivo experiments. Unmodified alginate solutions lacking RGD were prepared in an identical manner without the addition of peptide. Microcarrier beads with or without ECM were suspended in unmodified alginate by mixing the alginate solution with pre-swelled gelatin beads (15 mg/ml of alginate), the cell suspension, and CaSO$_4$ as described above.

Characterization of Materials

Pre-swelled beads were analyzed before and after ECM coating to qualitatively assess matrix coverage. The beads were sputter coated with gold and imaged using a Hitachi S3500-N scanning electron microscope. Compressive moduli of acellular gels were determined using an Instron 3345 testing device (Norwood, Mass.). Alginate hydrogels (n=6 per group) were loaded between two flat platens and compressed at 1 mm/min. Compressive moduli were calculated from the linear portion of the force-displacement graph for strain ranging from 0% to 5% (27).

In Vitro Quantification of Osteogenic Potential

To assess cell morphology within each gel formulation, cell-loaded constructs were prepared as described above. After 48 h, gels were rinsed in PBS and incubated in 200 µl of calcein AM (2 µM, Molecular Probes, Oreg.) for 15 min. The calcein solution was aspirated, and cell morphology was observed using fluorescence microscopy (Nikon Eclipse TE2000-U).

MSC-loaded disks were cultured in growth media for 24 hr, after which the media was refreshed with osteogenic media (growth media containing 10 nM dexamethasone, 50 µg/ml ascorbate-2-phosphate, and 10 mM beta-glycerophosphate, all from Sigma). To quantify gene expression in MSCs entrapped in each material, hydrogels were rinsed with PBS and total RNA was collected using the RNeasy Mini kit (Qiagen). 300 ng of total RNA was reverse-transcribed with Superscript II Reverse Transcriptase (Invitrogen). qPCR was performed using the TaqMan1 Universal PCR Master Mix (Applied Biosystems, Carlsbad, Calif.) on a Mastercycler1 Realplex2 (Eppendorf, Hauppauge, N.Y.). Primers and probes for IBSP (Hs00173720_m1), Sp7 (Hs01866874_s1), RUNX2 (Hs00231692_m1), and RPL13 (Hs00204173_m1) were purchased from Applied Biosystems. Amplification conditions were 50° C. for 2 min, 95° C. for 10 min, followed by 40 cycles at 95° C. for 15 s and 60° C. for 1 min. Quantitative gene expression values were normalized to RPL13 and presented as ΔC$_t$ values calculated as fold change in gene expression with respect to expression of the housekeeping gene.

Total DNA present in the alginate disks was determined using the Quant-iT PicoGreen dsDNA kit (Invitrogen). Briefly, disks were rinsed in PBS and placed in passive lysis buffer (Promega, Madison, Wis.). Following one freeze thaw cycle, the lysate was sonicated briefly, centrifuged at 10,000 rpm for 5 min, and the supernatant was quantified for DNA content. Intracellular alkaline phosphatase (ALP) from MSCs encapsulated in alginate gels was quantified using a PNPP colorimetric assay at 405 nm as described (28). ALP activity was normalized to DNA content.

In Vivo Bone Formation

Treatment of experimental animals was in accordance with University of California, Davis animal care guidelines and all National Institutes of Health animal handling procedures. Skeletally mature 10-week old male immunocompetent rats were anesthetized and maintained using a 2% isoflurane/$O_2$ mixture delivered through a mask. Hydrogels (RGD, BLK, ECM, and HI ECM) containing MSCs ($5 \times 10^6$ cells/ml) were prepared as described above. Four pockets were created in the dorsum, and hydrogels (one from each group) were implanted subcutaneously. The incision was closed, and the animals were maintained for 2 or 6 weeks (n=5 per time point). At each time point, animals were euthanized by $CO_2$ inhalation, implants were recovered and fixed in phosphate-buffered formalin for 24 h, and then moved to 70% ethanol for storage prior to processing and analysis. Mineral distribution and bone formation were visualized using plain film radiography.

Explanted hydrogels were paraffin-embedded, processed, and sectioned at 5 μm thickness. Vessel counts were performed from implants collected after two weeks using H&E-stained cross-sections at 100× magnification as previously described (1). The diameter of circular blood vessels within the margins of the entire tissue section (n=3 per condition) was measured using Image J software. Collagen distribution was identified in tissue sections from 6-week implants after Masson's trichrome stain.

Statistical Analysis

Results are expressed as mean±standard deviation. All in vitro experiments were performed in triplicate unless stated otherwise. Statistical analyses were performed by ANOVA followed by Student-Newman-Keuls post-hoc tests assessing significance to probability values (p)<0.05.

Results

Characterization of Alginate Hydrogels

Figure 27:
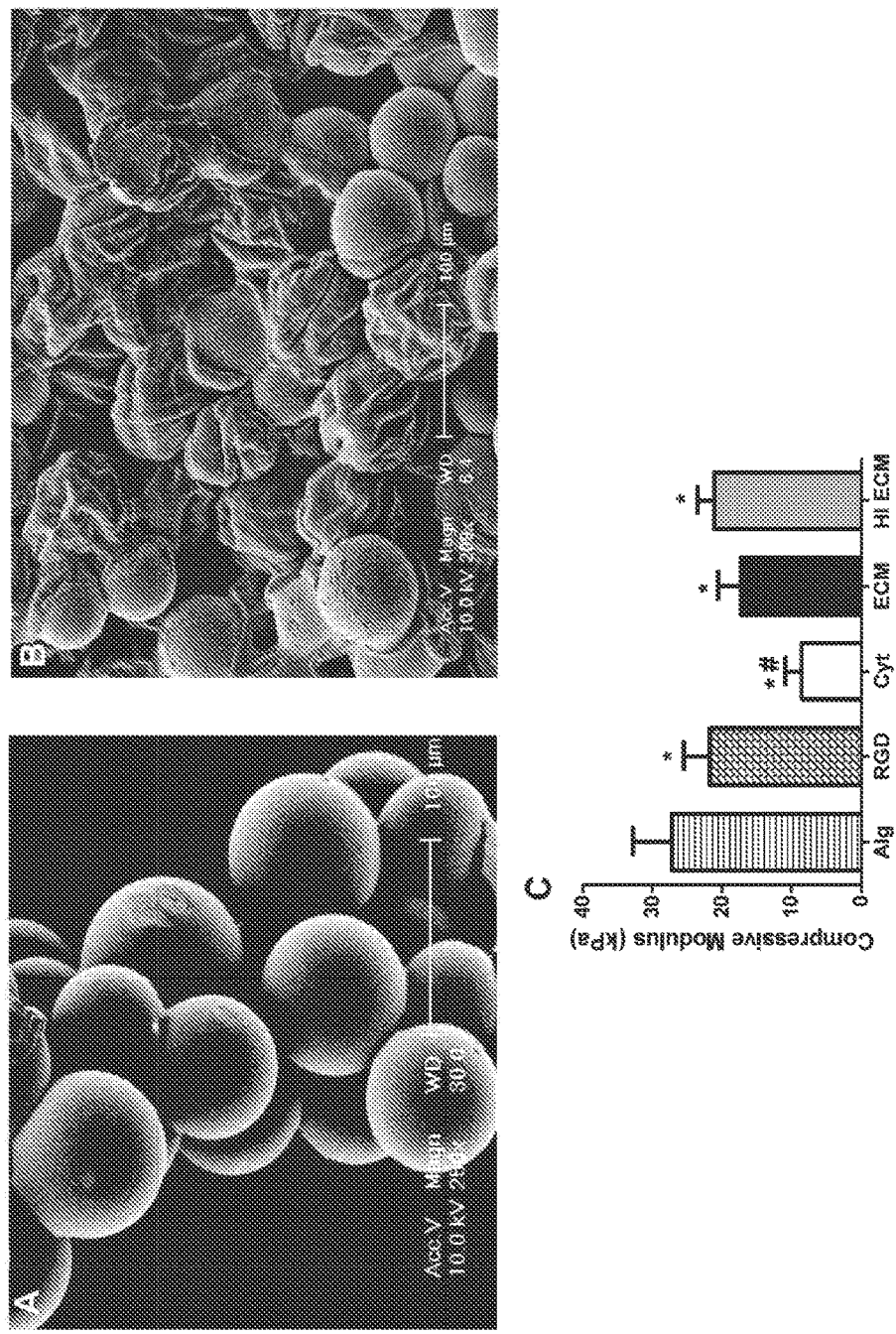
FIG. 27. Scanning electron microscopy of uncoated microcarrier beads (A) and beads coated with ECM (B). Images are at 250× magnification; scale bar represents 100 µm. (C) Compressive moduli of alginate hydrogels. *p<0.05 vs. ALG; #p<0.05 vs. RGD.

Compared to the smooth external appearance of uncoated microcarrier beads (FIG. 27A), heterogeneous aggregates of protein were visible on ECM-coated beads (FIG. 27B). We detected significant reductions in the compressive stiffness of hydrogels after peptide modification with RGD or the addition of microcarrier beads to unmodified alginate hydrogels (FIG. 27C). Compared to RGD-modified gels, the addition of uncoated microcarrier beads (BLK) yielded hydrogels with the lowest stiffness. Hydrogels containing beads coated with ECM (ECM, HI ECM) possessed greater compressive moduli that were similar in magnitude to RGD gels.

Figure 28:
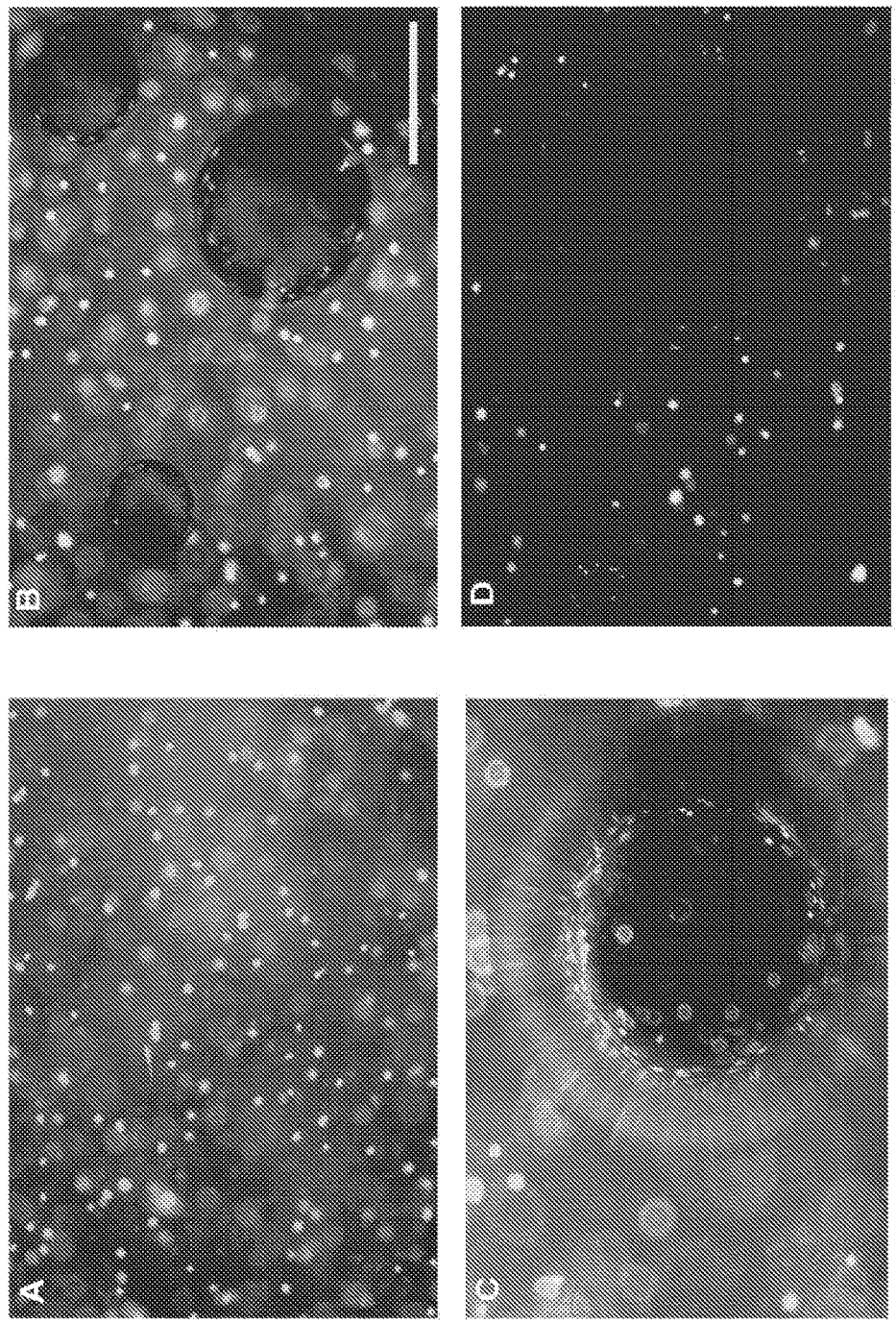
FIG. 28. Cell morphology of MSCs entrapped in alginate gels by fluorescence microscopy: (A) RGD, (B) BLK, (C) ECM, and (D) HI ECM. Images taken at 100× magnification; scale bar represents 100 µm.

MSCs within the gel interacted with microcarrier beads as a function ECM coating (FIG. 28). MSCs in ALG scaffolds demonstrated minimal cell survival and were not examined in further cell-based assays (data not shown). Cells in RGD scaffolds exhibited uniform distribution throughout the gel, but we observed minimal cell spreading after 48 hr (FIG. 28A). The incorporation of microcarrier beads within unmodified alginate (BLK, ECM, HI ECM) facilitated varying levels of cell attachment to the beads. The increase in cell attachment to beads in the ECM hydrogels (FIG. 28C) was apparent compared to cells entrapped in BLK (FIG. 28B) or HI ECM (FIG. 28D)

ECM-Coated Beads Promote MSC Osteogenic Differentiation

Figure 29:
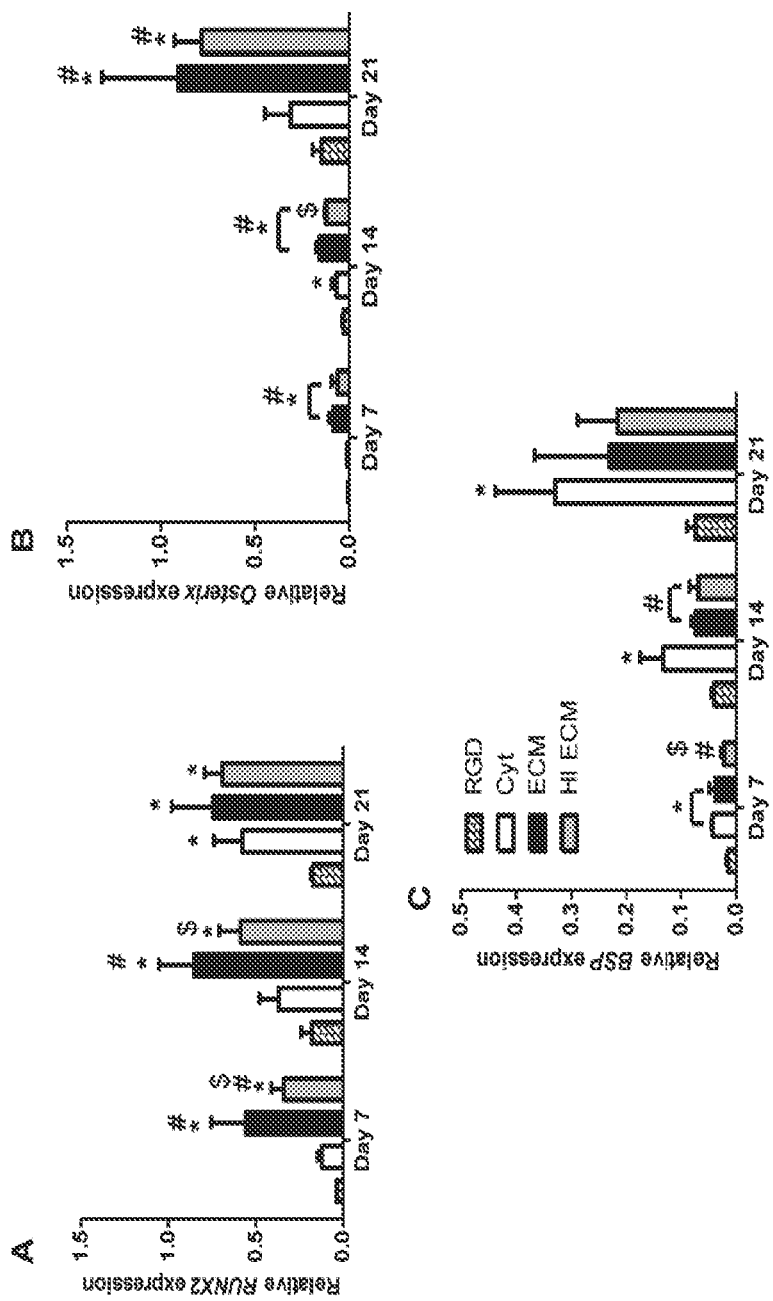
FIG. 29. Quantitative PCR results for genes monitored in MSCs seeded in RGD, BLK, ECM, and HI ECM hydrogels: (A) RUNX2, (B) Osterix, and (C) BSP. Values reflect fold change in target mRNA expression over RPL13. *p<0.05 vs. RGD; #p<0.05 vs. BLK; $p<0.05 vs. ECM.

We examined the expression of osteogenic markers such as RUNX2, Osterix, and BSP to determine if incorporating ECM coated beads in alginate hydrogels enhances osteogenic differentiation of undifferentiated MSCs. MSCs entrapped in ECM consistently exhibited the highest RUNX2 expression compared to cells in RGD, BLK, or HI ECM (FIG. 29A). Expression of RUNX2 increased steadily for all other groups over 21 days, but MSCs in RGD consistently exhibited the lowest expression of RUNX2. We observed similar trends in Osterix expression for MSCs in each scaffold, with cells in ECM or HI ECM possessing significantly higher expression at 21 days compared to the other groups (FIG. 29B). Cells in BLK exhibited the greatest BSP expression at all time points, and gene expression was significantly higher than in cells in RGD at all time points (FIG. 29C).

Figure 30:
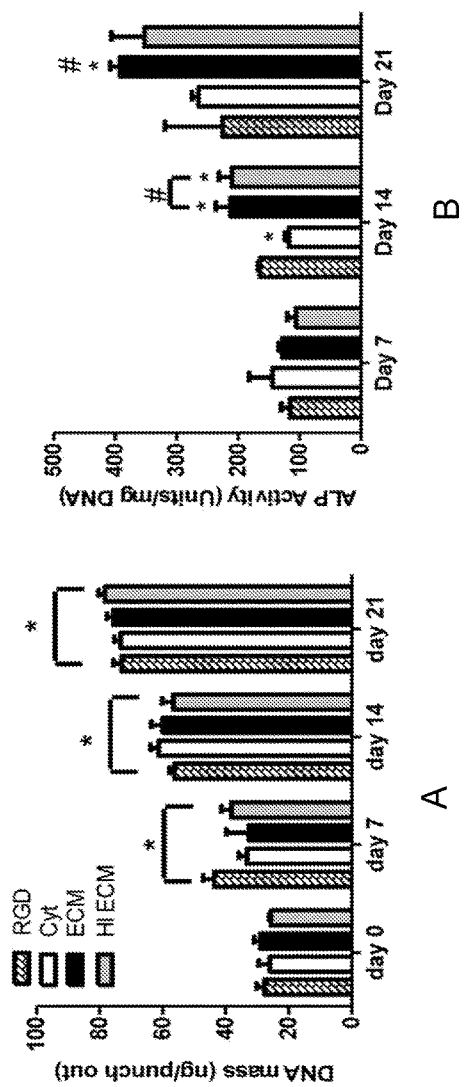
FIG. 30. Quantification of DNA mass (A) and secreted ALP levels (B) in MSCs seeded in RGD, BLK, ECM, and HI ECM hydrogels. *p<0.05 vs. RGD; #p<0.05 vs. BLK.

We observed significant increases in cell proliferation between the different time points, yet we did not detect appreciable differences in DNA mass between the different groups (FIG. 30A). Similar to osteogenic gene expression, we measured increased intracellular ALP activity for MSCs entrapped in all scaffolds (FIG. 30B). No differences in ALP activity were apparent at 7 days, but ALP activity was significantly greater in MSCs entrapped in ECM and HI ECM at 14 days compared to RGD and BLK. By 21 days, ALP activity was significantly greater in MSCs in ECM compared to RGD and BLK.

In Vivo Angiogenic and Osteogenic Response to Alginate Hydrogels

Figure 31:
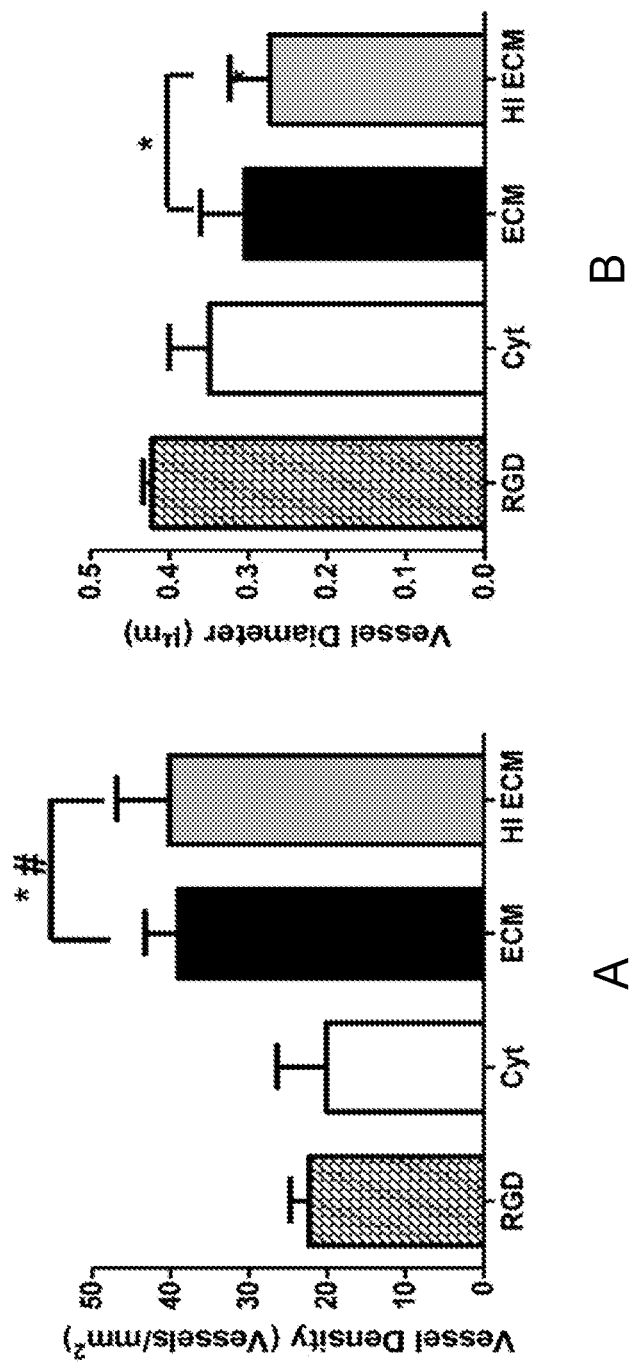
FIG. 31. Quantification of vessel density (A) and vessel diameter (B) in RGD, BLK, ECM and HI ECM hydrogels. *p<0.05 vs. RGD; #p<0.05 vs. BLK.

We next investigated whether implantation of MSCs in hydrogels containing ECM-coated carrier beads would yield detectable differences in neovascularization and bone formation compared to cells implanted in RGD. Upon explanation at two weeks, we detected significant increases in vessel density within ECM and HI ECM groups compared to RGD and BLK groups (FIG. 31A). No differences were apparent between gels containing ECM-coated beads. Despite increases in vessel density, the diameter of vessels invading the scaffolds containing ECM-coated beads was reduced compared to RGD or BLK (FIG. 31B).

Figure 32:
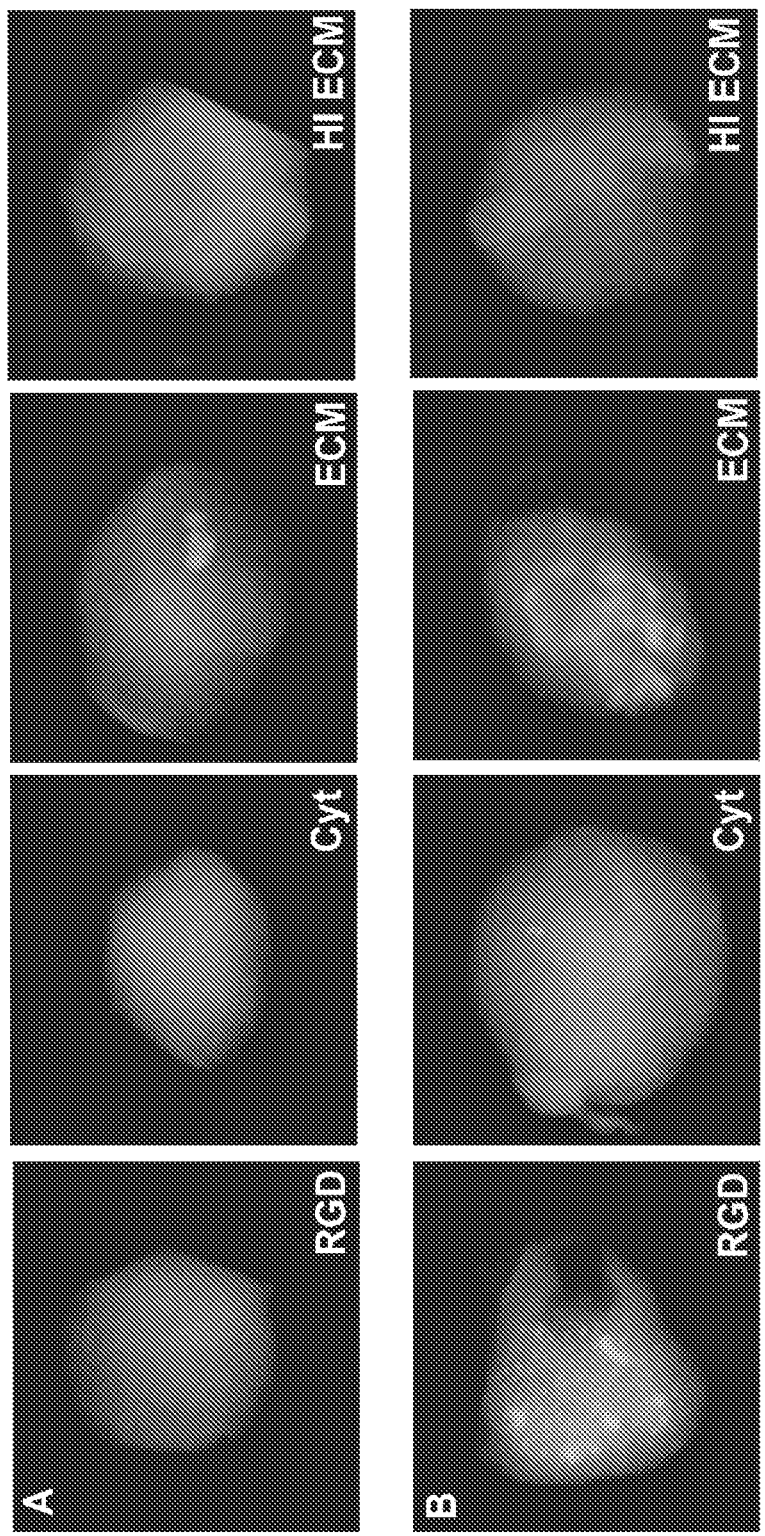
FIG. 32. Representative radiographic images of mineral formation in RGD, BLK, ECM, and HI ECM implants at 2 (A) and 6 weeks (B).
Figure 33:
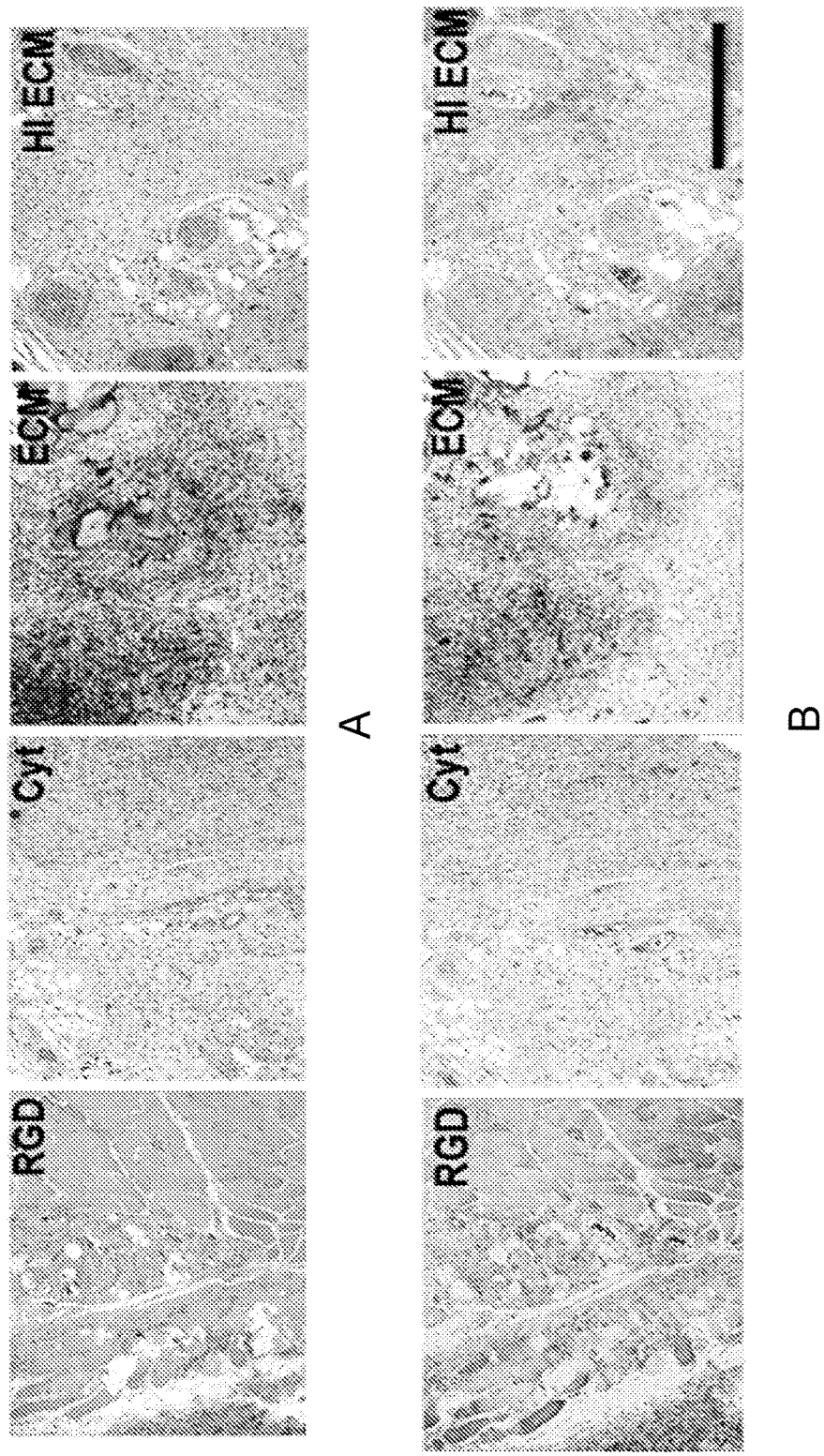
FIG. 33. (A) H&E and (B) Masson's trichrome stained sections of RGD, BLK, ECM, and HI ECM implants at 6 weeks. Images shown at 100×; scale bar represents 100 µm.

Mineralization within each scaffold group was assessed 2 and 6 weeks after implantation using radiography (FIGS. 32A and 32B respectively). ECM scaffolds appeared to contain mineral as early as two weeks after implantation, while no mineral was qualitatively observed in the other three groups. We observed a greater amount of mineral within ECM scaffolds after 6 weeks, and the mineral content appeared comparable to RGD scaffolds. No mineral was visible within BLK or HI ECM scaffolds (FIG. 32B). Consistent with x-ray analysis, histological examination of explants at 6 weeks revealed denser tissues within RGD and ECM scaffolds compared to the BLK and HI ECM groups (FIG. 33). All tissues stained contained substantial collagen (FIG. 33B), with BLK scaffolds exhibiting the least staining ECM gels were also more cellularized compared to the other scaffolds as demonstrated by the numerous cell nuclei within the H&E sections.

CONCLUSIONS

In this example, we showed that presentation of an engineered cell-secreted ECM on microbeads suspended in alginate hydrogels promotes cell adhesion and direct osteogenic differentiation of undifferentiated MSCs without chemical incorporation of cell-adhesive peptides. Human MSCs entrapped in alginate hydrogels loaded with ECM-coated beads (ECM) adhered to the bead, whereas cells remained dispersed in hydrogels containing uncoated beads. MSCs entrapped in ECM gels in vitro exhibited increased alkaline phosphatase activity and similar expression of osteogenic genes compared to hydrogels modified with RGD-containing peptides (RGD). Transplantation of MSCs into an ectopic site revealed significant increases in blood vessel density for ECM hydrogels compared to alginate gels containing uncoated beads or RGD. Furthermore, we observed comparable levels of bone formation at 6 weeks when transplanting cells in ECM and RGD hydrogels. These findings demonstrate that engineered ECMs can be deployed in a minimally invasive manner to direct the formation of bony tissue. This strategy provides an alternative to the engraftment of proteins or peptides onto the polymer backbone of hydrogels for directing cellular behavior.

REFERENCES FOR EXAMPLE 6

1. He J, Genetos D C, Leach J K. Osteogenesis and trophic factor secretion are influenced by the composition of hydroxyapatite/poly(lactide-co-glycolide) composite scaffolds. Tissue Eng Part A. 16:127-37. 2010.
2. Gkioni K, Leeuwenburgh S C, Douglas T E, Mikos A G, Jansen J A. Mineralization of hydrogels for bone regeneration. Tissue Eng Part B Rev. 16:577-85. 2010.
3. Bhat A, Dreifke M B, Kandimalla Y, Gomez C, Ebraheim N A, Jayasuriya A C. Evaluation of cross-linked chitosan microparticles for bone regeneration. J Tissue Eng Regen Med. 4:532-42. 2010.
4. Nguyen M K, Lee D S. Injectable biodegradable hydrogels. Macromol Biosci. 10:563-79. 2010.
5. Lee K Y, Mooney D J. Hydrogels for tissue engineering. Chem. Rev. 101:1869-79. 2001.
6. Diduch D R, Jordan L C, Mierisch C M, Balian G. Marrow stromal cells embedded in alginate for repair of osteochondral defects. Arthroscopy. 16:571-7. 2000.
7. Ruoslahti E, Reed J C. Anchorage dependence, integrins, and apoptosis. Cell. 77:477-8. 1994.
8. Grigoriou V, Shapiro I M, Cavalcanti-Adam E A, Composto R J, Ducheyne P, Adams C S. Apoptosis and survival of osteoblast-like cells are regulated by surface attachment. J Biol. Chem. 280:1733-9. 2005.
9. Hern D L, Hubbell J A. Incorporation of adhesion peptides into nonadhesive hydrogels useful for tissue resurfacing. J Biomed Mater Res. 39:266-76. 1998.
10. Alsberg E, Anderson K W, Albeiruti A, Franceschi R T, Mooney D J. Cell-interactive alginate hydrogels for bone tissue engineering. J Dent Res. 80:2025-9. 2001.
11. Rowley J A, Madlambayan G, Mooney D J. Alginate hydrogels as synthetic extracellular matrix materials. Biomaterials. 20:45-53. 1999.
12. LeBaron R G, Athanasiou K A. Extracellular matrix cell adhesion peptides: functional applications in orthopedic materials. Tissue Eng. 6:85-103. 2000.
13. Pierschbacher M D, Ruoslahti E. Cell attachment activity of fibronectin can be duplicated by small synthetic fragments of the molecule. Nature. 309:30-3. 1984.
14. Ruoslahti E, Pierschbacher M D. New perspectives in cell adhesion: RGD and integrins. Science. 238:491-7. 1987.
15. Rezania A, Healy K E. Biomimetic peptide surfaces that regulate adhesion, spreading, cytoskeletal organization, and mineralization of the matrix deposited by osteoblast-like cells. Biotechnol Progr. 15:19-32. 1999.
16. Sofia S, McCarthy M B, Gronowicz G, Kaplan D L. Functionalized silk-based biomaterials for bone formation. Journal of Biomedical Materials Research. 54:139-48. 2001.
17. Frondoza C, Sohrabi A, Hungerford D. Human chondrocytes proliferate and produce matrix components in microcarrier suspension culture. Biomaterials. 17:879-88. 1996.
18. Malda J, Frondoza CG. Microcarriers in the engineering of cartilage and bone. Trends Biotechnol. 24:299-304. 2006.
19. Lao L H, Tan H P, Wang Y J, Gao C Y. Chitosan modified poly(L-lactide) microspheres as cell microcarriers for cartilage tissue engineering. Colloid Surface B. 66:218-25. 2008.
20. Wu Y N, Yang Z, Hui J H P, Ouyang H W, Lee E H. Cartilaginous ECM component-modification of the micro-bead culture system for chondrogenic differentiation of mesenchymal stem cells. Biomaterials. 28:4056-67. 2007.
21. Zambonin G, Grano M. Biomaterials in orthopaedic surgery: effects of different hydroxyapatites and demineralized bone matrix on proliferation rate and bone matrix synthesis by human osteoblasts. Biomaterials. 16:397-402. 1995.
22. Ohgushi H, Miyake J, Tateishi T. Mesenchymal stem cells and bioceramics: strategies to regenerate the skeleton. Novartis Found Symp. 249:118-27; discussion 27-32, 70-4, 239-41. 2003.
23. Kang Y, Kim S, Khademhosseini A, Yang Y. Creation of bony microenvironment with CaP and cell-derived ECM to enhance human bone-marrow MSC behavior and delivery of BMP-2. Biomaterials. 32:6119-30. 2011.
24. Datta N, Pham Q P, Sharma U, Sikavitsas V I, Jansen J A, Mikos A G. In vitro generated extracellular matrix and fluid shear stress synergistically enhance 3D osteoblastic differentiation. Proc Natl Acad Sci USA. 103:2488-93. 2006.
25. Decaris M L, Mojadedi A, Bhat A, Leach J K. Transferable cell-secreted extracellular matrices enhance osteogenic differentiation. Acta Biomater. 2011.
26. Decaris M L, Leach J K. Design of experiments approach to engineer cell-secreted matrices for directing osteogenic differentiation. Ann Biomed Eng. 39:1174-85. 2011.
27. Davis H E, Miller S L, Case E M, Leach J K. Supplementation of fibrin gels with sodium chloride enhances physical properties and ensuing osteogenic response. Acta Biomater. 7:691-9. 2011.
28. He J, Genetos D C, Yellowley C E, Leach J K. Oxygen tension differentially influences osteogenic differentiation of human adipose stem cells in 2D and 3D cultures. Journal of cellular biochemistry. 110:87-96.
29. Simmons C A, Alsberg E, Hsiong S, Kim W J, Mooney D J. Dual growth factor delivery and controlled scaffold degradation enhance in vivo bone formation by transplanted bone marrow stromal cells. Bone. 35:562-9. 2004.
30. Rowlands A S, George P A, Cooper-White J J. Directing osteogenic and myogenic differentiation of MSCs: interplay of stiffness and adhesive ligand presentation. Am J Physiol Cell Physiol. 295:C1037-44. 2008.
31. Engler A J, Sen S, Sweeney H L, Discher D E. Matrix elasticity directs stem cell lineage specification. Cell. 126:677-89. 2006.
32. Kozawa O, Matsuno H, Uematsu T. Involvement of p70 S6 kinase in bone morphogenetic protein signaling: vascular endothelial growth factor synthesis by bone morphogenetic protein-4 in osteoblasts. J Cell Biochem. 81:430-6. 2001.
33. Kempen D H, Lu L, Heijink A, Hefferan T E, Creemers L B, Maran A, et al. Effect of local sequential VEGF and BMP-2 delivery on ectopic and orthotopic bone regeneration. Biomaterials. 30:2816-25. 2009.
34. Anitua E, Andia I, Ardanza B, Nurden P, Nurden A T. Autologous platelets as a source of proteins for healing and tissue regeneration. Thromb Haemostasis. 91:4-15. 2004.
35. Weltermann A, Wolzt M, Petersmann K, Czerni C, Graselli U, Lechner K, et al. Large amounts of vascular endothelial growth factor at the site of hemostatic plug formation in vivo. Arterioscl Throm Vas. 19:1757-60. 1999.

Example 7

Use of DMs for Biologically Active Material (BAM) Delivery

BAMs of interest will be added to DM supports and introduced in vivo in mammals. As noted above, BAMs include therapeutic agents, such as drugs, and also genetic materials and biological materials.

Cells (e.g., MSCs) will be acquired and DM will be produced as previously described [Decaris, M. L. and J. K. Leach, *Design of experiments approach to engineer cell-secreted matrices for directing osteogenic differentiation.* Ann Biomed Eng, 2011. 39(4): p. 1174-85]. In some experiments, adipose stem cells (ASCs) are used. BAMs will be contacted with DMs. The efficiency of adsorption will be determined, e.g., by measuring fluorescence in the supernatant upon aspiration, and plates will be allowed to dry within a sterile biosafety cabinet for 12 h. Plates will then be scraped in the presence of a small volume of 0.02 N acetic acid, transferred to microcentrifuge tubes, and sonicated on ice with 2 s pulses 10-15 times to mechanically homogenize DM contents. DM contents will be diluted with 0.02 N acetic acid as necessary for contacting supports. Solubilized DMs will then be combined with supports (e.g. scaffolds) formed from, e.g., hydroxyapatite and poly(lactide-co-glycolide) (HA-PLG). Supports can remain undisturbed for 30 min, after which they will be flipped and the process repeated. The quantity of absorbed DM will be determined by Amido black protein quantification, while DM distribution throughout the support will be determined by immunohistochemistry of supports.

Supports will be characterized, e.g., as described above. Supports will be implanted in mammals and characterized, e.g., as described above.

In some experiments, bone repair in a model of diabetes is determined using 5 month-old male Wistar rats injected with streptozotocin as described [Shyng, Y. C., et al., *Healing of tooth extraction sockets in the streptozotocin diabetic rat model: Induction of cartilage by BMP-6.* Growth Factors, 2010. 28(6): p. 447-51.]. Implants from one of the 6 groups described in Table 3 is immediately implanted in the formed defect, and bone formation is characterized. For BAM-adsorbed scaffolds, DM-coated scaffolds without a BAM is implanted in the contralateral side as a control.

Autologous bone inlay will serve as the positive control, while a surgical defect is left untreated on the contralateral side to examine spontaneous repair. Bone formation is observed longitudinally in a consistent subset of animals from each study group over the 12-week experiment using tools within the Center for Molecular and Genomic Imaging to noninvasively monitor angiogenesis (laser Doppler), metabolic activity within the defect (PET), and bone formation (microCT). Other characterizations are performed, e.g., as described above.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Tables

TABLE 1

| DOE Input Variables | Specific Conditions Tested |
| --- | --- |
| A. Culture Duration | 3, 9, 15 days |
| B. Oxygen Tension | 5, 13, 21% $O_2$ |
| C. Cell Density | 2e4, 5e4, 8e4 cells/$cm^2$ |
| D. Media Type | SM, OM |

DOE input variables considered and specific experimental levels tested.

TABLE 2

| DOE Output Response | Significant Input Variables ($p < 0.05$) |
| --- | --- |
| SP7 expression | A, C, D |
| RUNX2 expression | A, B, $A^2$, $B^2$ |
| IBSP expression | A, D, $A^2$ |
| DNA quantification | A, D, $B^2$ |

Naïve hMSC output responses and input variables determined to be of significance.
ABBREVIATIONS
A: culture duration;
B: oxygen tension;
C: cell density;
D: Media Type;
X: linear interaction between output and variable;
$X^2$: quadratic interaction between output and variable

TABLE 3

| PROTEIN | TISSUE ASSESSMENT METHOD | ASSESSMENT TIME (WEEKS) | ENDPOINTS |
| --- | --- | --- | --- |
| 1 | LDPI | 1, 2, 4, 6 | Vascularization |
| 2 | Histology | 2 | |
| 1 + 2 | | | |
| — | PET | 4, 8, 12 | Cell metabolism |
| Neg. Control: HA-PLG scaffold | | | |
| Positive Control: bone inlay | microCT histology | 4, 8, 12 12 | Bone formation |

GENERAL REFERENCES

1. Alsberg, E., et al., (2002) *Engineering growing tissues.* PNAS 99(19): p. 12025-30.
2. Decaris, M. L. and J. K. Leach, (2010) *Design of Experiments Approach to Engineer Cell-Secreted Matrices for Directing Osteogenic Differentiation.* Ann Biomed Eng, 2010.
3. Datta et al. (2007) *In vitro generated extracellular matrix and fluid shear stress synergistically enhance 3D osteoblastic differentiation.* PNAS 103:2488.
4. U.S. Pat. No. 7,326,571 to Freyman.
5. International patent application publication no. WO 97/018842 to Abatangelo.

The invention claimed is:
1. A method for producing a composition comprising a decellularized extracellular matrix (DM) comprising a) obtaining a population of extracellular matrix-free mesenchymal stem cells (MSCs) and growing the MSCs on a tissue culture substrate under conditions sufficient to form an extracellular matrix (ECM);
b) removing the cells from the tissue culture substrate to form a tissue culture substrate coated with DM;
c) separating the DM from the tissue culture substrate into a solvent to form a solution comprising the DM; and
d) dissociating the DM in the solution, thereby producing the composition comprising the DM.

2. The method of claim 1, wherein
step a) comprises obtaining and growing a population of human MSCs derived from bone marrow on a tissue culture substrate comprising tissue culture plastic (TCP) by seeding MSCs at 50,000 cells/cm² and maintaining the MSCs in ambient oxygen at 21% $O_2$ in alpha modified Eagle's medium (MEM) supplemented with 50 µg/ml ascorbate-2-phosphate for 15 days to form an ECM; wherein
step b) comprises removing the cells from the tissue culture substrate by treatment with 0.5% Triton X-100 in 20 mM ammonium hydroxide ($NH_4OH$) in phosphate buffered saline (PBS) for 5 minutes at 37 degrees C. to form a tissue culture substrate coated with DM; wherein
step c) comprises separating the DM from the tissue culture substrate by treatment with 0.02 N acetic acid and scraping the DM from the tissue culture substrate into the 0.02 N acetic acid to form a solution comprising the DM; and wherein
step d) comprises dissociating the DM in the solution by sonication, thereby producing the composition comprising the DM.

3. The method of claim 1, wherein the MSCs are from bone marrow, adipose tissue, muscle, periodontal tissue, or dental pulp.

4. The method of claim 1, wherein the MSCs are human, mouse, rat, dog, cat, rabbit, horse, pig, or nonhuman primate.

5. The method of claim 1, wherein separating the DM from the tissue culture substrate comprises treatment with an acidic solvent and mechanical removal of the DM from the tissue culture substrate or scraping or lifting the DM from thermoresponsive polymers by reducing the temperature.

6. The method of claim 1, wherein separating the DM from the tissue culture substrate comprises treatment with an acidic solvent and scraping the DM from the tissue culture substrate.

7. The method of claim 1, wherein the cells are human MSCs.

8. The method of claim 1, wherein the DM has a protein content of about 10-20 µg/cm², wherein the DM has 99% less DNA as compared to a non-decellularized ECM control sample, and wherein the DM expresses type 1 collagen, fibronectin, biglycan, and, decorin.

9. The method of claim 1, wherein the ECM is osteogenic, chondrogenic, myogenic, adipogenic, keratinogenic, keratogenic, neurogenic, tenogenic, angiogenic, urotheliogenic, hepatogenic, or nephrogenic.

10. The method of claim 9, wherein the ECM is osteogenic.

11. The method of claim 1, further comprising contacting the DM with a biologically active material (BAM), after step d), under conditions sufficient for adsorption of the BAM by the DM.

12. The method of claim 11, wherein the biologically active material is a therapeutic agent, a small molecule, a nucleic acid, or a protein molecule.

13. The method of claim 11, wherein the biologically active material is a protein molecule that is differentially expressed in diabetes patients.

14. The method of claim 1, further comprising contacting the DM with a cross-linking agent after step d).

15. The method of claim 14, wherein the crosslinking agent is 1-Ethyl-3-[3-dimethylaminopropyl]carbodiimide hydrochloride (EDC).

16. A method for producing a composition free of cells comprising a decellularized osteogenic extracellular matrix (oDM) produced in tissue culture, the method comprising
a) growing a population of human MSCs derived from bone marrow on a tissue culture substrate comprising TCP by seeding human MSCs at high density (greater than or equal to 50,000 cells/sq. cm) and maintaining in ambient oxygen (21% $O_2$) in alpha modified Eagle's medium supplemented with 50 µg/ml ascorbate-2-phosphate for 15 days to form an extracellular matrix (ECM);
b) removing the cells from the tissue culture substrate by treatment with 0.5% Triton X-100 in 20 mM $NH_4OH$ in PBS for 5 minutes at 37 degrees C. to form tissue culture substrate coated with oDM;
c) separating the oDM from the tissue culture substrate by treatment with 0.02 N acetic acid and scraping the oDM from the tissue culture substrate into the 0.02 N acetic acid to form a solution comprising the oDM; and
d) dissociating the oDM in the solution by sonication, thereby producing the composition comprising the osteogenic decellularized ECM.

* * * * *